US010562836B2

(12) United States Patent
Shimizu et al.

(10) Patent No.: US 10,562,836 B2
(45) Date of Patent: Feb. 18, 2020

(54) PROCESS FOR PRODUCING ACETIC ACID

(71) Applicant: Daicel Corporation, Osaka-shi, Osaka (JP)

(72) Inventors: Masahiko Shimizu, Himeji (JP); Hiroyuki Miura, Himeji (JP); Yoshihisa Mizutani, Himeji (JP)

(73) Assignee: DAICEL CORPORATION, Osaka-shi (JP)

( * ) Notice: Subject to any disclaimer, the term of this patent is extended or adjusted under 35 U.S.C. 154(b) by 32 days.

(21) Appl. No.: 15/565,604

(22) PCT Filed: May 27, 2016

(86) PCT No.: PCT/JP2016/065822
§ 371 (c)(1),
(2) Date: Oct. 10, 2017

(87) PCT Pub. No.: WO2016/194850
PCT Pub. Date: Dec. 8, 2016

(65) Prior Publication Data
US 2018/0118651 A1 May 3, 2018

(30) Foreign Application Priority Data
Jun. 1, 2015 (JP) .................................. 2015-111750

(51) Int. Cl.
| C07C 51/44 | (2006.01) |
| C07C 51/12 | (2006.01) |
| C07C 53/08 | (2006.01) |
| C07C 19/00 | (2006.01) |
| C07C 17/386 | (2006.01) |
| B01D 3/06 | (2006.01) |
| B01D 3/14 | (2006.01) |
| B01D 3/40 | (2006.01) |
| B01D 5/00 | (2006.01) |
| C07B 61/00 | (2006.01) |
| C07C 19/07 | (2006.01) |

(52) U.S. Cl.
CPC ................. *C07C 51/44* (2013.01); *B01D 3/06* (2013.01); *B01D 3/148* (2013.01); *B01D 3/40* (2013.01); *B01D 5/006* (2013.01); *C07C 17/386* (2013.01); *C07C 19/07* (2013.01); *C07C 51/12* (2013.01); *C07C 53/08* (2013.01); *C07B 61/00* (2013.01)

(58) Field of Classification Search
CPC ........ C07C 51/44; C07C 53/08; C07C 17/386; C07C 51/12; B01D 3/40
See application file for complete search history.

(56) References Cited

U.S. PATENT DOCUMENTS

| 4,241,219 A * | 12/1980 | Wan ...................... C07C 51/12 560/232 |
| 5,625,095 A | 4/1997 | Miura et al. |
| 9,505,695 B2 * | 11/2016 | Scates ..................... B01D 3/34 |
| 2002/0098123 A1 | 7/2002 | Matsumoto et al. |
| 2013/0303800 A1 | 11/2013 | Shimizu |

FOREIGN PATENT DOCUMENTS

| EP | 2 628 720 A1 | 8/2013 | |
| JP | 8-67650 A | 3/1996 | |
| JP | 2001-96102 A | 4/2001 | |
| JP | 2003-518053 A | 6/2003 | |
| WO | WO 01/46109 A1 | 6/2001 | |
| WO | WO-0146109 A1 * | 6/2001 | ............ C07C 17/38 |
| WO | WO 2014/031407 A1 | 2/2014 | |

OTHER PUBLICATIONS

English translation of International Preliminary Report on Patentability and Written Opinion dated Dec. 14, 2017, in PCT International Application No. PCT/JP2016/065822.
International Search Report for PCT/JP2016/065822 (PCT/ISA/210) dated Aug. 30, 2016.
Written Opinion of the International Searching Authority for PCT/JP2016/065822 (PCT/ISA/237) dated Aug. 30, 2016.
Extended European Search Report dated Feb. 22, 2018, in European Patent Application No. 16803285.2.

* cited by examiner

*Primary Examiner* — Paul A Zucker
(74) *Attorney, Agent, or Firm* — Birch, Stewart, Kolasch & Birch, LLP

(57) ABSTRACT

A process for producing acetic acid while efficiently separating permanganate reducing compounds (PRC's) and methyl iodide is provided. PRC's are separated or removed from a mixed composition (3A) containing PRC's and methyl iodide by distilling the mixed composition in a distillation step (5) to form an overhead stream (5A), a side-cut stream (5B), and a lower stream (5C). In a distillation column of the distillation step (5), an extractant (e.g., water) extracting PRC's preferentially to methyl iodide is added to a concentration zone in which PRC's and methyl iodide are concentrated, and an extraction mixture falling from the concentration zone is withdrawn as the side-cut stream (5B).

14 Claims, 5 Drawing Sheets

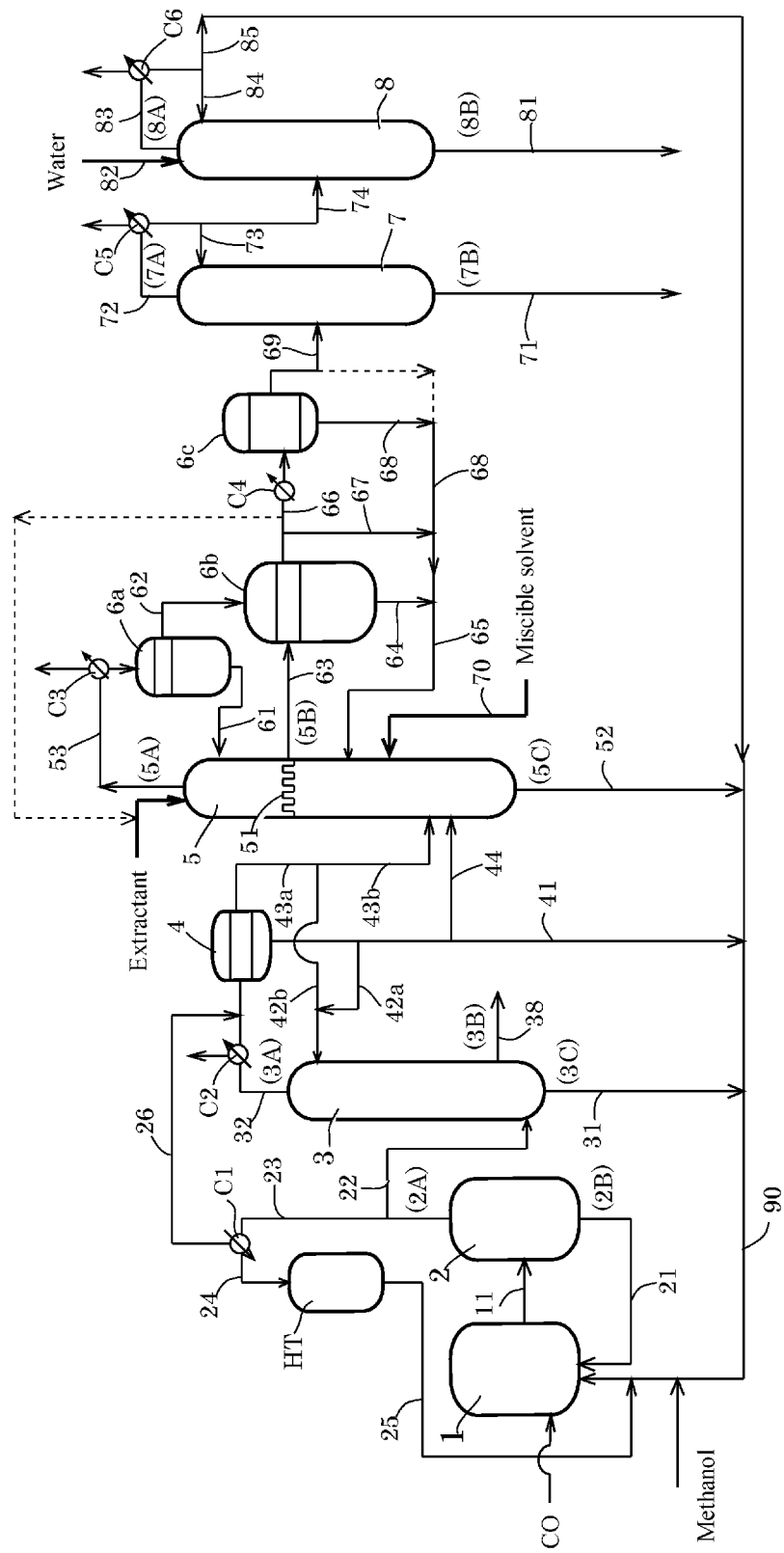
[Fig. 1]

[Fig. 2]
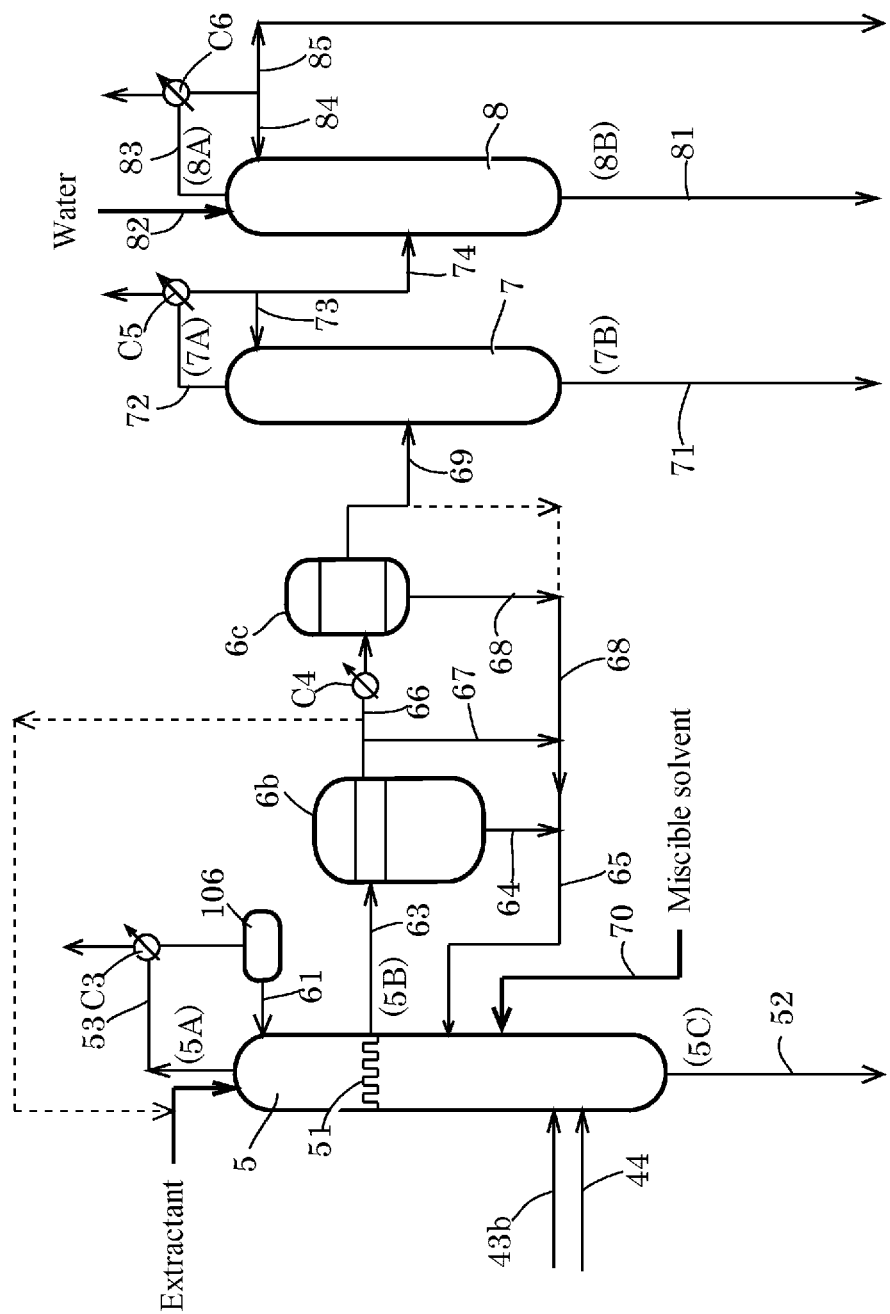

[Fig. 3]
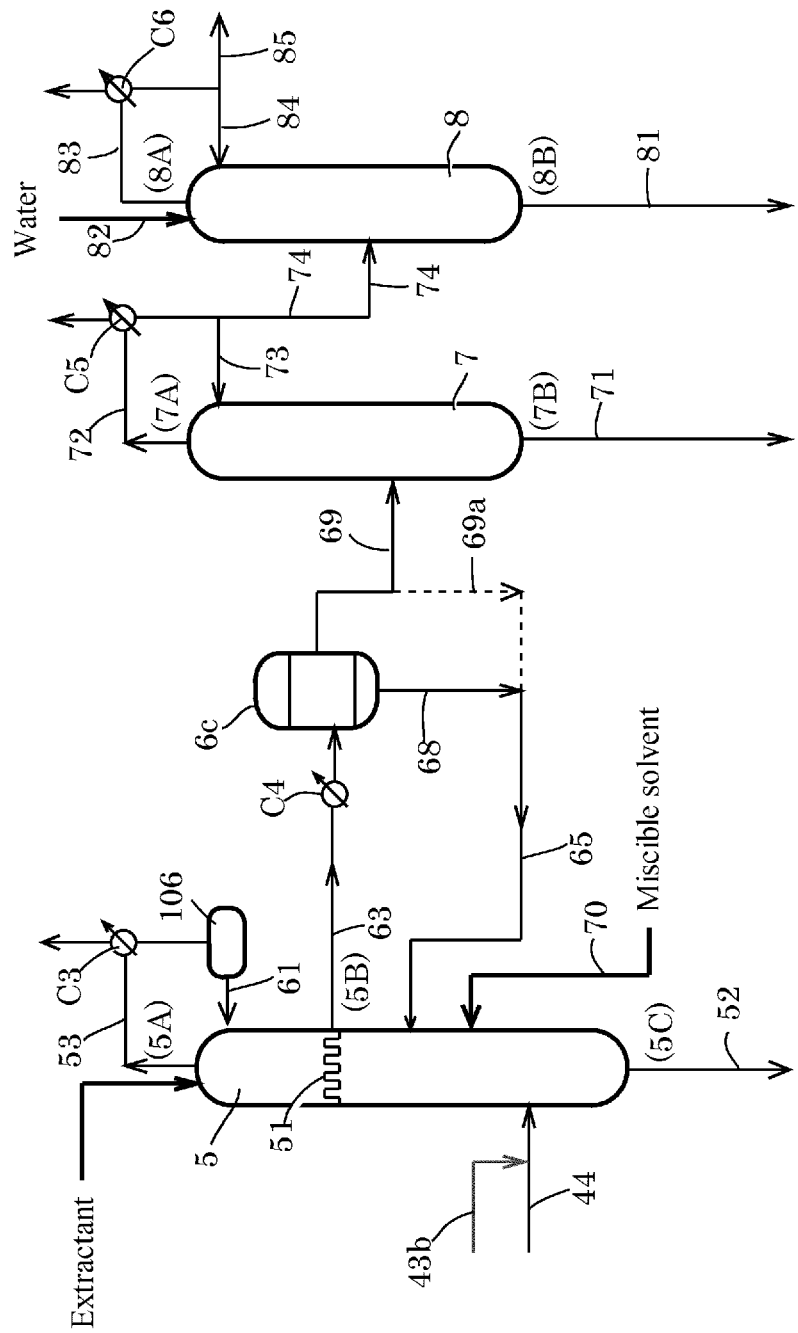

[Fig. 4]
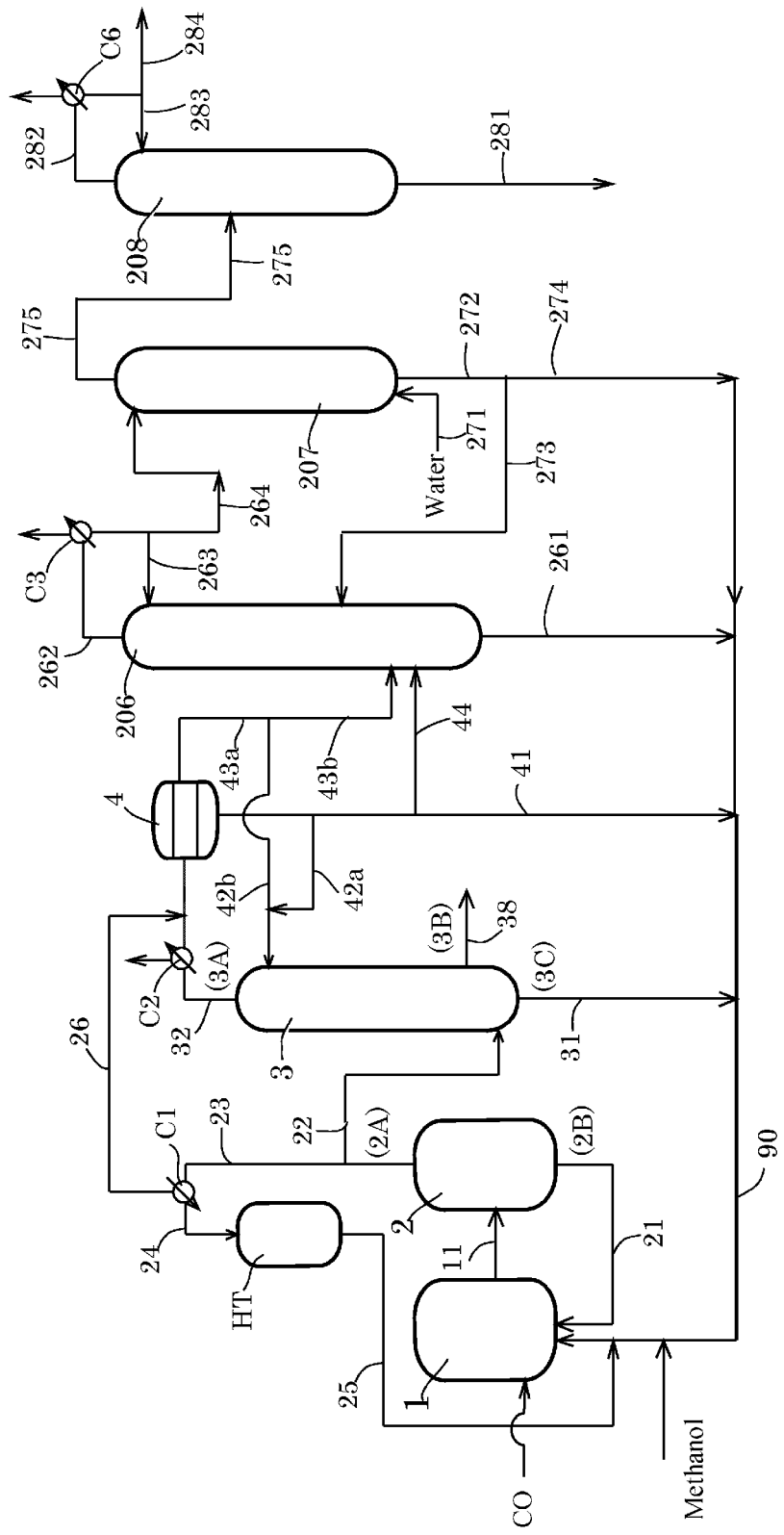

[Fig. 5]
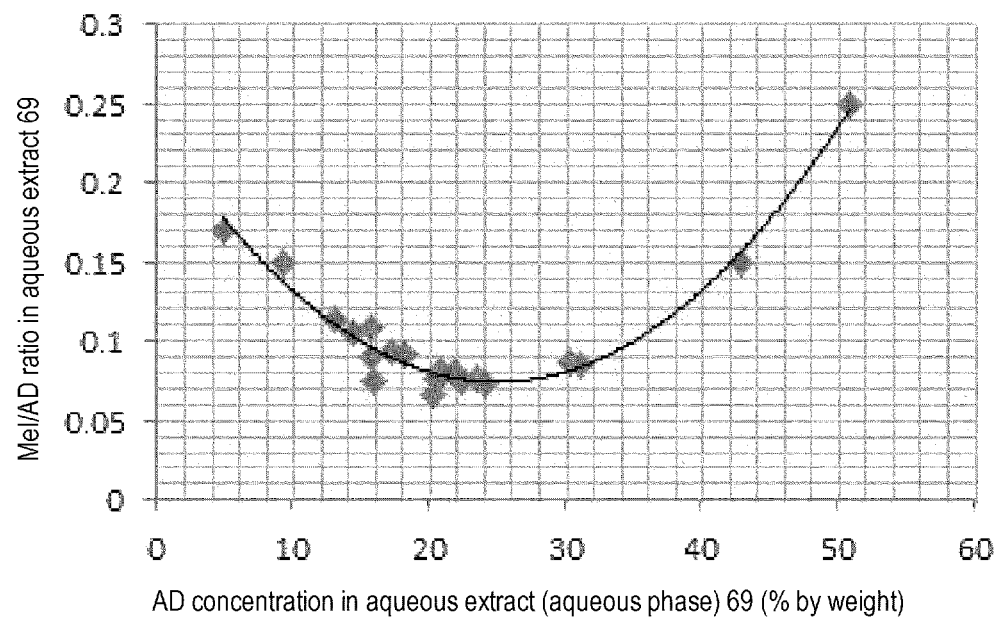

PROCESS FOR PRODUCING ACETIC ACID

TECHNICAL FIELD

The present invention relates to processes useful for separating permanganate reducing compounds (PRC's) such as acetaldehyde and methyl iodide from each other to remove the PRC's, and also relates to processes for producing acetic acid by methanol carbonylation with utilizing the above separation processes.

BACKGROUND ART

Acetic acid is produced industrially by carbonylating methanol in the presence of water, a rhodium catalyst, a metal iodide, and methyl iodide. For the methanol carbonylation reaction, the reaction mixture contains small amounts of by-products (impurities), for example, a carbonyl compound (e.g., acetaldehyde, butyraldehyde, crotonaldehyde, 2-ethylcrotonaldehyde, and an aldol condensation product thereof), an organic iodide (e.g., a $C_{2-12}$alkyl iodide such as ethyl iodide, butyl iodide, or hexyl iodide), and others. These impurities result in low quality of product acetic acid. For example, a permanganate reducing compound test (permanganate time) detects extremely small amounts of impurities (permanganate reducing compounds; PRC's) even if the extremely small amounts are difficult to determine quantitatively by current advanced instrumental analysis. Unfortunately, acetaldehyde and methyl iodide have close boiling points to each other, and thus it is difficult to separate acetaldehyde and methyl iodide from each other efficiently by an ordinary distillation means alone. Moreover, separation of the impurities by combination of distillation with water extraction has also been reported. According to this process, for coexistence of methyl acetate with PRC's as well as methyl iodide, methyl acetate is dissolved in and distributed to an aqueous phase in the water extraction, and thus methyl iodide may also undesirably be extracted into the aqueous phase. This results in a loss of methyl iodide.

Japanese Patent Application Laid-Open Publication No. 8-67650 (JP-8-67650A, Patent Document 1) discloses a process for removing acetaldehyde, comprising the steps of: separating a reaction mixture of methanol carbonylation into a volatile phase containing acetic acid, methyl acetate and methyl iodide and a less-volatile phase containing a rhodium catalyst; distilling the volatile phase to form a product mixture containing acetic acid and an overhead containing methyl acetate and methyl iodide; separating the overhead into a lower phase (a methyl iodide phase) and an upper phase (an aqueous phase containing acetaldehyde); distilling the lower phase and/or the upper phase in a distillation column (an acetaldehyde removing column) to form an acetaldehyde concentrate from a top of the column; and subjecting the acetaldehyde concentrate to a water extraction.

However, in distilling the upper phase (aqueous phase) containing acetaldehyde, it is necessary to provide a large amount of energy for distillation and separation of acetaldehyde due to distillation of water having a large latent heat for evaporation, or it is necessary to reduce the amount of energy required for the distillation by increasing the number of distillation stages (or plates). Whereas, in distilling the lower phase (methyl iodide phase), it is necessary to increase a reflux amount or to increase the number of distillation stages, due to a small difference in boiling point between methyl iodide and acetaldehyde. Moreover, the distillation of a mixture or homogeneous liquid of the upper phase and the lower phase also involves an increase in the amount of vapor (the amount of heat energy) in the distillation column and/or an increase in the number of distillation stages. This results in economically low production of acetic acid.

Furthermore, the process described in Patent Document 1 fails to increase an acetaldehyde removal efficiency in the distillation column, because acetaldehyde is not concentrated in the overhead effectively.

WO 2014/031407 (Patent Document 2) discloses a process for producing acetic acid, the process comprising the steps of: separating a crude acetic acid composition in a light ends column (a splitter column) into an overhead stream comprising methyl iodide, water, methyl acetate, and permanganate reducing compounds (PRC's), and an acetic acid product stream; separating a portion of the overhead stream in a first distillation column to form a stream enriched in at least one PRC, wherein the enriched stream further comprises at least some of the methyl iodide; and extractive distilling the enriched stream with an extractive agent (e.g., water) in a second distillation column to form a distillate comprising methyl iodide and a residue comprising at least one PRC and optionally less than 1 wt. % methyl iodide. This document also discloses a mass flow ratio of the enriched stream relative to the extractive agent of at least 0.01:1.

Unfortunately, according to this process, for distillation and separation in the first distillation column, as the same as the process described in Patent Document 1, it is necessary to provide a large amount of energy or it is necessary to increase the number of distillation stages. In addition, the extractive distillation of the PRC's in the second distillation column needs a large amount of an extractive agent and a large number of the distillation stages and thus requires a large amount of separation energy. Further, methyl acetate or acetic acid coexistent with the PRC's in the second extractive distillation step is dissolved in an aqueous phase in the water extractive distillation, and thus methyl iodide may undesirably be extracted into the aqueous phase. This results in a loss of methyl iodide.

CITATION LIST

Patent Literature

Patent Document 1: JP-8-67650A (Claims, [0007], [0018], and Examples)

Patent Document 2: WO 2014/031407 (Claims)

SUMMARY OF INVENTION

Technical Problem

It is therefore an object of the present invention to provide a process for efficiently separating PRC's and methyl iodide from each other, and a process for producing acetic acid.

Another object of the present invention is to provide a process for effectively separating PRC's, which result in low quality of acetic acid, and methyl iodide from each other by a compact (or simple) apparatus with a low energy, and a process for producing acetic acid.

It is still another object of the present invention to provide a process for efficiently separating PRC's and methyl iodide from each other with a small number of distillation stages, and a process for producing acetic acid.

It is a further object of the present invention to provide a process for efficiently separating PRC's and methyl iodide from each other by extractive distillation of PRC's in the coexistence of methyl acetate and/or acetic acid, and a process for producing acetic acid.

Solution to Problem

The inventors of the present invention made intensive studies to achieve the above objects and finally found that (i) distillation of a mixed composition (or a mixture) containing methyl iodide and a low concentration of acetaldehyde forms a concentration zone (a high concentration zone or a condensed zone or an enriched zone) of methyl iodide and acetaldehyde in a distillation column; (ii) water extractive distillation in which water (which can preferentially extract acetaldehyde) is added to the concentration zone from a top of the distillation column makes the boiling point of the extract higher than the boiling point of acetaldehyde to easily increase the concentration of acetaldehyde in the extract, and efficiently separates methyl iodide and acetaldehyde from each other to transfer acetaldehyde from the methyl iodide phase to the aqueous phase without concentrating acetaldehyde in the methyl iodide phase (the extractive distillation enables the formation of an extract containing a high concentration of acetaldehyde); and (iii) withdrawing a liquefied fraction (or an extraction mixture) falling from the concentration zone not as a bottom stream but as a side-cut stream reduces the amount of energy required for the distillation and also reduces the number of distillation stages, and these findings establishes a process which enables economically advantageous removal of acetaldehyde. The present invention was accomplished based on the above findings.

Hereinafter, the present invention will be explained with respect to reference numerals in the drawings. The reference numerals are only used to aid understanding of the present invention and are not intended to be limited to specific units or process streams indicated by the reference numerals. For example, although FIG. 1 shows a process comprising indirectly feeding an overhead stream or mixed composition (3A) from a first distillation column (3) to a second distillation column (5), any stream having a composition of the mixed composition (3A) may be fed to any one or plurality of distillation columns following the first distillation column (3); any one or plurality of distillation columns is not limited to the second distillation column (5).

That is, an aspect of the present invention provides a process for separating or removing a permanganate reducing compound (in particular, at least acetaldehyde) from a mixed composition (or a mixture) (3A) containing at least a permanganate reducing compound (a PRC or PRC's including acetaldehyde) and methyl iodide, the process comprising distilling the mixed composition in a distillation step (5) to form an overhead stream (5A), a side-cut stream (5B), and a lower stream (5C). In a distillation column of the distillation step (5), an extractant (or an extraction solvent) which can extract PRC's preferentially to methyl iodide is added to a concentration zone (a high concentration zone) of PRC's and methyl iodide; and an extraction mixture (a liquefied fraction, a falling liquid) falling from the concentration zone is withdrawn as the side-cut stream (5B).

The mixed composition (3A) may contain methyl iodide in a concentration of not less than 1.5% by weight (for example, not less than 2% by weight), or may be a mixed composition in which at least methyl iodide among permanganate reducing compounds (PRC's) and methyl iodide is concentrated compared with a mixed stream produced in a preceding unit operation. Further, the mixed composition (3A) may usually contain methyl iodide in a concentration of not less than 10% by weight (for example, not less than 20% by weight). Thus, according to the present invention, the mixed composition (3A) may biphasically be separable and may contain at least a portion of an organic phase, at least a portion of an aqueous phase, or a mixture of the organic phase and the aqueous phase.

According to such a process, an ascending stream containing concentrated PRC's and methyl iodide is allowed to countercurrently contact with a descending stream of the extractant, and an extract having a high concentration of PRC's can be formed with a small amount of the extractant without highly concentrating PRC's by distillation for separating methyl iodide and PRC's from each other. Thus, the process not only enables efficient separation of PRC's and methyl iodide from each other but also makes the distillation space smaller to efficiently extract PRC's with a small quantity of heat energy and a small number of distillation stages.

Therefore, (i) the PRC concentration (in particular, the acetaldehyde concentration) in the extraction mixture or side-cut stream (5B) can be higher than (or increased compared with) the PRC concentration in each of the mixed composition (3A) and the lower stream (5C). For example, (ii) the concentration of each one of PRC's or the concentration of all PRC's in the extraction mixture or side-cut stream (5B) (e.g., an aqueous phase formed from the extraction mixture) may be about 0.1 to 45% by weight (e.g., about 5 to 45% by weight). Moreover, (iii) the ratio of PRC's (in particular, acetaldehyde) relative to methyl iodide in the extraction mixture or side-cut stream (5B) may be larger than PRC's (in particular, acetaldehyde) relative to methyl iodide in each stream of the mixed composition (3A) and the lower stream (5C). Further, the methyl iodide concentration in the aqueous phase formed from the side-cut stream (5B) can be reduced compared with a methyl iodide concentration in an aqueous phase formed by water extraction of a distillate (an overhead condensate) from a conventional acetaldehyde-removing column, and thus a loss of methyl iodide can be reduced.

The mixed composition (3A) may further contain methyl acetate. Furthermore, the mixed composition (3A) may contain at least one component selected from the group consisting of acetic acid, methanol, water, dimethyl ether, and an acetaldehyde derivative (a substance derived from acetaldehyde).

The flow rate of the extractant may be relatively low, and, for example, the weight ratio of the flow rate of the extractant relative to the flow rate of the mixed composition (3A) [the former/the latter] may be about 0.0001/100 to 100/100, preferably about 0.0001/100 to 20/100, and particularly about 0.001/100 to 10/100 in terms of liquid matter.

Specifically, the distillation column of the distillation step (5) may usually be provided with a receiver disposed at a lower position than an addition port for the extractant. The height level of the receiver may be the same height level as a feed port for the mixed composition (3A) or may be upper or lower than a feed port for the mixed composition (3A).

In a case where the receiver is disposed at a lower position than the feed port for the mixed composition (3A), the receiver may be positioned upper than the bottom stream. Such a receiver may permit a vapor or evaporation fraction of the mixed composition to ascend to the concentration zone and may be capable of receiving the extraction mixture (liquefied fraction, falling liquid) falling from the concentration zone. The extractant which is separable from methyl iodide to form an extract phase may be added to the concentration zone formed above (or over) the receiver. The extraction mixture may be withdrawn as the side-cut stream (5B) from a withdrawing port communicating with the receiver. The extractant can be added or sprayed from an addition port positioned at an upper position of the distillation column than the feed port for the mixed composition. More specifically, the distillation column may be provided with at least one chimney tray. An aqueous extractant may be added or sprayed to the concentration zone being formed above (or over) an uppermost chimney tray and containing a vapor or evaporation fraction of the mixed composition (3A); the extraction mixture from the concentration zone (or the liquid falling from the concentration zone, the liquefied mixture) may be received in a tray section or area of the chimney tray; and the extraction mixture retained in the tray section or area may be withdrawn as the side-cut stream (5).

The extractant may be an aqueous extractant, for example, at least one aqueous solvent selected from the group consisting of (i) water, (ii) an aqueous process stream produced in the process, and (iii) an aqueous solution (or an aqueous mixture) produced by water absorption treatment of an off-gas from the process. The aqueous solvent (or process stream) (ii) produced in the process may contain, for example, water and at least one component selected from the group consisting of PRC's, methyl iodide, acetic acid, methyl acetate, methanol, dimethyl ether, and all components (such as impurities) present in the aqueous process stream.

Feeding the extractant (e.g., an aqueous solvent such as water) to the distillation column from the upper position (e.g., the top) thereof probably allows the extraction mixture or the falling liquid to form a liquid-liquid separated state easily. Thus the extraction mixture (5B) may be liquid-liquid separable into an upper phase and a lower phase. In a case where the extraction mixture (5B) is separable into an aqueous phase and an organic phase, the aqueous phase may be separated, and the organic phase may be recycled to the distillation column or others. For example, at least a portion (or the whole amount) of the extraction mixture (5B) may be withdrawn from the distillation column of the distillation step (5) and biphasically separated into aqueous and organic phases, the aqueous phase containing at least acetaldehyde may be separated, and the organic phase containing at least methyl iodide may be recycled to the distillation column of the distillation step (5) directly or indirectly. The extraction mixture (5B) and the overhead stream (5A) may be biphasically separated independently or in combination (for example, at least the extraction mixture (5B) among the extraction mixture (5B) and the overhead stream (5A) may be biphasically separated) to form aqueous phase and organic phases, the aqueous phase containing at least acetaldehyde may be separated, and the organic phase containing at least methyl iodide may be recycled to the distillation column of the distillation step (5). In the distillation column of the distillation step (5), the extraction mixture (the falling liquid) may be retained in the tray to form an aqueous phase containing at least acetaldehyde and an organic phase containing at least methyl iodide, the aqueous phase may be separated, and the organic phase may be recycled to the distillation column of the distillation step (5). The extraction mixture may be withdrawn from the distillation column of the distillation step and biphasically separated to form an aqueous phase containing at least acetaldehyde and an organic phase containing at least methyl iodide, and at least a portion of the aqueous phase and the organic phase may be recycled to the distillation column of the distillation step. The organic phase may be fed to an upper or lower position than the withdrawing port of (or for) the side-cut stream (5B) to form a concentration zone in the distillation column of the distillation step (5).

According to the present invention, PRC's (e.g., acetaldehyde) can efficiently be extracted with an aqueous extractant such as water, and the vapor pressure of PRC's (e.g., acetaldehyde) in the aqueous extractant can be lowered (that is, the boiling point of the extract can be raised or elevated) to increase the concentration of PRC's in the extractant. By utilizing a higher distribution factor of PRC's (e.g., acetaldehyde) in the aqueous phase compared with in the the organic phase (or methyl iodide phase), the concentration of PRC's (e.g., acetaldehyde) in the aqueous extractant phase (aqueous phase) can be increased compared with that in the organic phase (or methyl iodide phase). Thus, the reduced concentration of PRC's in the organic phase and the efficient dissolution of PRC's in the aqueous phase can separate PRC's and methyl iodide from each other. Further, since the concentration of PRC's in the organic phase can be reduced, PRC's (e.g., acetaldehyde) can efficiently be removed in the form of an aqueous solution even at a small number of distillation stages (or plates) and a low energy (energy saving).

The extraction mixture (the falling liquid) withdrawn may biphasically be separated in a decanter, for example, under the condition of a retention time of not less than 10 seconds. The residence (or retention) time may be the total time of the residence time of the liquid which is in contact with the extractant in the receiver (or chimney tray) of the distillation column and the residence time of the liquid in the decanter.

The mixed composition (3A) contains PRC's (e.g., acetaldehyde) and methyl iodide. The mixed composition (3A) may be produced in a process for producing acetic acid. For example, the process of the present invention may comprise: (1) a reaction step for continuously carbonylating methanol in the presence of a catalyst system containing a metal catalyst, metal halide, and methyl iodide; (2) a flash evaporation step for continuously separating the reaction mixture into a volatile phase (2A) containing the product acetic acid and methyl iodide and a less-volatile phase (2B) containing the metal catalyst and the metal halide; (3) a first distillation step for continuously separating the volatile phase (2A) into an overhead (3A) containing methyl iodide and by-product acetaldehyde and a stream (3B) containing acetic acid; and (4) a step for condensing a gaseous phase to form an organic phase and an aqueous phase, the gaseous phase being produced from at least one step selected from the group consisting of these steps and containing at least acetaldehyde and methyl iodide, wherein at least a portion of the organic phase (the organic phase rich in methyl iodide) and/or at least a portion of the aqueous phase may be subjected to the second distillation step (5), and water or at least a portion of the aqueous phase (the aqueous phase rich in acetaldehyde) may be utilized as the extractant. For example, the overhead (3A) may be brought into contact with water to form an organic phase rich in methyl iodide and an aqueous phase rich in acetaldehyde, and the organic phase may be subjected to the second distillation step (5), and the aqueous phase may be utilized as the extractant in the second distillation step (5).

The overhead stream (5A) and/or the side-cut stream (extraction mixture) (5B) separated in the distillation step (5) may further be subjected to a third distillation step (7). For example, at least the extraction mixture (5B) among the overhead stream (5A) and the extraction mixture (5B) may biphasically be separated into an aqueous phase and an organic phase, and at least a portion of the aqueous phase may be subjected to a succeeding distillation step (7) to form an overhead stream (a lower boiling point stream, an upper stream) (7A) containing acetaldehyde and methyl iodide and a liquid stream (7B) (a higher boiling point stream, a bottom stream or lower stream) containing the extractant. The liquid stream (7B) containing the extractant may be reused as the extractant in the second distillation step (5). The overhead (7A) may have a PRC (representatively, acetaldehyde) concentration of about 1 to 99% by weight and a methyl iodide concentration of about 0.1 to 10% by weight, and the liquid stream (7B) may have a methyl iodide concentration of not more than 1% by weight (provided that, each stream, including impurities, has a total amount of 100% by weight).

As described above, at least the extraction mixture (5B) among the extraction mixture (5B) and the overhead stream (5A) may biphasically be separated into an aqueous phase and an organic phase (or a raffinate) containing at least methyl iodide, at least a portion of the aqueous phase may be subjected to distillation in the succeeding distillation step (7) and/or water extractive distillation in a succeeding distillation step (8), the organic phase may directly or indirectly be recycled to the second distillation step (5) from a lower position than the withdrawing port for the side-cut stream (5B). Moreover, a miscible solvent which is miscible with the organic phase separated from the extraction mixture (5B) may be directly or indirectly fed to the second distillation step (5) from a lower position than the withdrawing port for the side-cut stream (5B). The miscible solvent may, for example, be at least one component selected from the group consisting of water, acetic acid, methyl iodide, and methanol.

The amount to be added of the miscible solvent may be not more than 30% by weight relative to the amount of the falling liquid from the concentration zone in the distillation column of the distillation step (5). The total amount to be recycled of the aqueous phase separated from the extraction mixture (5B) and/or the amount to be added of the miscible solvent may be not more than 30% by weight relative to the amount of the falling liquid from the concentration zone in the distillation step (5).

The process of the present invention may further comprise (8) a step for subjecting the following (a) and/or (b) to water extraction or water extractive distillation: (a) at least a portion of the aqueous phase separated from at least the extraction mixture (5B) among the extraction mixture (5B) and the overhead stream (5A), and (b) the overhead stream (7A) from the third distillation step (7). The water extraction step (8) may be a step for separating the overhead stream (7A) into a phase or stream (a raffinate) rich in methyl iodide and a phase or stream (an extract) rich in PRC's, or may be (8) a fourth distillation step for subjecting the overhead stream (7A) to water extractive distillation to form an overhead stream (8A) and a bottom liquid stream (8B). In the distillation step (8), the water extraction may be carried out under the condition that the ratio of methyl iodide relative to acetaldehyde in the overhead stream (8A) is larger than that in the feed liquid stream.

Another aspect of the present invention provides a process for producing acetic acid by utilizing the above separation process. The production process comprises distilling a mixed composition (or a mixture) (2A) containing at least a permanganate reducing compound (PRC), methyl iodide, methyl acetate, and acetic acid to separate the mixed composition into an overhead (3A) containing at least acetaldehyde and methyl iodide and an acetic acid stream (3B) containing product acetic acid; and subjecting at least a portion of the overhead (3A) to the distillation step (5) to give acetic acid. Specifically, acetic acid may continuously be produced by the process comprising: (1) a reaction step for continuously carbonylating methanol in the presence of a catalyst system containing a metal catalyst, a metal halide, and methyl iodide; (2) a flash evaporation step for continuously separating the reaction mixture into a volatile phase (2A) containing product acetic acid and methyl iodide and a less-volatile phase (2B) containing the metal catalyst and the metal halide; (3) a distillation step for continuously separating the volatile phase (2A) into an overhead (3A) containing methyl iodide and by-product acetaldehyde and a stream (3B) containing acetic acid; and the distillation step (5) for distilling at least a portion of the overhead (3A).

As used herein, acetaldehyde may simply be referred to as PRC's. The extraction mixture in the distillation column of the distillation step (5) is withdrawn as the side-cut stream (5B), and thus the side-cut stream (5B) withdrawn from the distillation step (5) may simply be referred to as an extraction mixture (5B). The term "falling liquid" is synonymous with "falling stream". The term "extraction mixture" is synonymous with "extracted mixture" or "extraction mixture stream".

Advantageous Effects of Invention

According to the present invention, since PRC's are preferentially extracted with an extractant from a concentration zone of PRC's and methyl iodide and the extraction mixture is withdrawn as a side-cut stream, PRC's and methyl iodide are efficiently separable from each other. Thus, PRC's and methyl iodide are efficiently separable from each other with a significantly decreased amount of the extractant and a low energy. Further, PRC's and methyl iodide are separable from each other even by a compact (or simple) apparatus having a distillation column with a small number of stages (or plates). Furthermore, PRC's and methyl iodide are efficiently separable from each other even in the coexistence with methyl acetate or acetic acid.

BRIEF DESCRIPTION OF DRAWINGS

FIG. 1 is a flowchart (or a flow diagram) for explaining a production process (or production apparatus) of acetic acid in accordance with an embodiment of the present invention.

FIG. 2 is a flowchart (or a flow diagram) for explaining a production process (or production apparatus) of acetic acid in accordance with another embodiment of the present invention.

FIG. 3 is a flowchart (or a flow diagram) for explaining a process in accordance with an embodiment of Examples.

FIG. 4 is a flow chart (or flow diagram) for explaining a conventional production process (or production apparatus) of acetic acid.

FIG. 5 is a graph showing a relationship between a concentration of acetaldehyde (AD) and a methyl iodide/acetaldehyde ratio (MeI/AD ratio) in Examples.

DESCRIPTION OF EMBODIMENTS

Hereinafter, the present invention will be explained in detail with reference to the drawings if necessary. In FIGS. 1 to 4, each step and a main apparatus or unit for the corresponding step may be indicated by the same reference numeral. Unless otherwise specifically noted, an acetaldehyde-containing aqueous phase obtainable by liquid-liquid (or biphasic) separation is synonymous with a light phase or an upper phase, and a methyl iodide-containing organic phase obtainable by liquid-liquid (or biphasic) separation is synonymous with a heavy phase, a methyl iodide phase, or a lower phase. An aqueous phase obtainable by extraction is synonymous with an extract, and an organic phase obtainable by extraction means the same as a raffinate.

With reference to a distillation column, the term "number of stages (or plates)" means either the number of theoretical stages (or plates) or the number of actual stages (or plates). For example, one theoretical stage (or plate) corresponds to two actual stages (or plates) if the efficiency of the actual stage (or plate) is 50%. The species or kind of the distillation column is not limited to a plate (Oldershaw) column, and may be a packed column. The species or kind of the distillation column is not particularly limited to a specific one. Hereinafter, unless otherwise specifically noted, the term "number of stages (or plates)" simply means the number of actual stages (or plates) in a plate column. The position at which a fluid flows in/flows out a packed column (inflow/outflow position) means a position corresponding to a height level of a plate of a plate column. For example, the 20th plate from the bottom of a plate column having the number of actual stages (or plates) of 50 means a height level corresponding to the 20th plate/the 50 plates from the bottom of a packed column (the height level "0.4" relative to the height "1" of a packed layer or bed of a packed column).

The embodiment of FIG. 1 shows a continuous process (or apparatus) for producing acetic acid from a reaction mixture (or a liquid reaction medium) produced by carbonylation reaction of methanol with carbon monoxide in the presence of a catalyst system comprising a rhodium catalyst as a metal catalyst and a co-catalyst [lithium iodide as a metal halide and methyl iodide] as well as acetic acid, methyl acetate, and a finite (or limited) amount of water.

The process (or production apparatus) comprises (1) a reaction step (a reaction system or a reactor) for carrying out a carbonylation reaction of methanol; (2) a flash evaporation step (a flasher) for separating a reaction mixture (or a reaction liquid) containing product acetic acid into a volatile phase (or lower boiling point fraction) (2A) and a less-volatile phase (or higher boiling point fraction) (2B); (3) a first distillation step (a splitter column or a distillation column) for separating the volatile phase (2A) into a first overhead (3A), an acetic acid stream (3B) as a side-cut stream, and a bottom liquid stream (higher boiling point fraction) (3C); (4) a first liquid-liquid separation step for condensing the first overhead (3A) to form two phases; (5) a second distillation step (a second distillation column) for separating an organic phase (a heavy phase rich in methyl iodide) formed in the liquid-liquid separation step (4) into a second overhead stream (5A), a side-cut stream (5B), and a lower stream (5C); (6) a second liquid-liquid separation step (a separation unit 6a, a hold tank 6b, and a decanter 6c) for separating the second overhead stream (5A) and the side-cut stream (5B) into two phases; (7) a third distillation step (a third distillation column) for separating an aqueous phase (light phase) formed in the second liquid-liquid separation step (6) into a third overhead stream (7A) and a liquid stream (7B); and (8) a fourth distillation step (a fourth distillation column) for subjecting the third overhead stream (7A) to water extractive distillation to form an overhead stream (8A) and a bottom liquid stream (8B).

Incidentally, among these steps, the process of the present invention comprises at least the second distillation step (5). Other steps [for example, the first liquid-liquid separation step (4), the second liquid-liquid separation step (6), the third distillation step (7), and the fourth distillation step (8)] are not necessarily essential. The process of the present invention usually comprises the first distillation step (3), the liquid-liquid separation step (4), and the second distillation step (5), and may comprise the liquid-liquid separation step (6). The second distillation step (5) is not limited to a single distillation step and may contain a plurality of distillation steps using a plurality of distillation columns. For the production of acetic acid, the process of the present invention usually further comprises the reaction step (1) and the flash evaporation step (flasher) (2).

As the distillation column of each of the distillation steps (3), (5), (7), and (8) (including the splitter column of the first distillation step (3)), there may be used a plate column, a packed column, or other columns.

Hereinafter, the process shown in FIG. 1 will be explained in more detail.

(1) Reaction Step (Reactor)

In the reaction step (reactor) (1), methanol and carbon monoxide are continuously fed to a reactor in the presence of a reaction medium containing a carbonylation catalyst system and water and produce acetic acid by carbonylation of methanol.

The carbonylation catalyst system usually contains a metal catalyst (such as a cobalt catalyst, a rhodium catalyst, or an iridium catalyst), a catalyst stabilizer or reaction accelerator, and a co-catalyst. The metal catalysts may be used alone or in combination. The metal catalyst may preferably include a rhodium catalyst and an iridium catalyst (in particular, a rhodium catalyst).

The metal catalyst may be used in the form of a simple metal, a metal oxide (including a complex metal oxide), a metal hydroxide, a metal iodide, a metal carboxylate (e.g., an acetate), a metal salt of an inorganic acid (e.g., a sulfate, a nitrate, and a phosphate), or a metal complex. It is preferred to use the metal catalyst in a form (e.g., a complex form) dissolvable in a liquid phase (or a reaction liquid). The rhodium catalyst may preferably include, for example, a rhodium iodide complex {e.g., $RhI_3$, $RhI_2(CO)_4]^-$, and $[Rh(CO)_2I_2]^-$} and a rhodium carbonyl complex. The metal catalyst has a concentration of, for example, about 100 to 5000 ppm (on the basis of weight, the same applies hereinafter), preferably about 200 to 3000 ppm, more preferably about 300 to 2000 ppm, and particularly about 500 to 1500 ppm in the whole liquid phase in the reactor.

The catalyst stabilizer or reaction accelerator may include a metal iodide capable of producing an iodide ion in the reaction medium, for example, an alkali metal iodide (e.g., lithium iodide, sodium iodide, and potassium iodide). Among these stabilizers, lithium iodide is preferred. These co-catalysts or accelerators may be used alone or in combination.

The catalyst stabilizer or reaction accelerator in the whole liquid phase in the reactor has a concentration of, for example, about 1 to 25% by weight, preferably about 2 to 22% by weight, and more preferably about 3 to 20% by weight. The iodide ion in the reaction system may have a concentration of, for example, about 0.05 to 2.5 mol/L and preferably about 0.25 to 1.5 mol/L.

As the co-catalyst, methyl iodide may be used. The methyl iodide in the whole liquid phase in the reactor has a concentration of, for example, about 1 to 30% by weight, preferably about 5 to 25% by weight, and more preferably about 6 to 20% by weight (e.g., about 8 to 18% by weight).

A preferred carbonylation catalyst system may comprise a rhodium catalyst, a metal iodide as a catalyst stabilizer (e.g., lithium iodide), and methyl iodide as a co-catalyst. To the reactor may be fed a catalyst mixture (a catalyst liquid) containing the carbonylation catalyst system and water.

The reaction medium (or liquid phase) usually contains product acetic acid, methyl acetate formed by a reaction of product acetic acid and raw material methanol, and water. The acetic acid also plays as a solvent. Moreover, the reaction medium (or the liquid phase) usually contains unreacted raw material methanol. The proportion of methyl acetate in the whole reaction liquid may be about 0.1 to 30% by weight, preferably about 0.3 to 20% by weight, and more preferably about 0.5 to 10% by weight (e.g., about 0.5 to 6% by weight). The water in the reaction medium may have a low concentration. The water in the whole reaction liquid has a concentration of, for example, about 0.1 to 15% by weight, preferably about 0.5 to 10% by weight, and more preferably about 0.8 to 5% by weight (e.g., about 1 to 3% by weight) or may have a concentration of about 1 to 10% by weight (e.g., about 2 to 5% by weight).

The carbon monoxide partial pressure in the reactor may be a pressure of, for example, about 0.2 to 3 MPa and preferably about 0.4 to 1.5 MPa. A waste gas containing carbon monoxide produced in the succeeding step(s) may be recycled to the reaction system.

The carbonylation reaction produces hydrogen by a reaction of carbon monoxide with water. Hydrogen increases the catalyst activity. Thus hydrogen may be fed to the reactor if necessary. Hydrogen may be fed to the reactor by recycling gaseous component(s) (including hydrogen, carbon monoxide, or other gases) exhausted in the process, if necessary after purifying and/or separating the gaseous component(s) in the succeeding step(s). The hydrogen partial pressure in the reaction system may be a pressure of, for example, about 0.5 to 250 kPa (e.g., about 1 to 200 kPa), preferably about 5 to 150 kPa, and more preferably about 10 to 100 kPa (e.g., about 10 to 50 kPa) in terms of absolute pressure.

The temperature of the carbonylation reaction may be, for example, about 150 to 250° C., preferably about 160 to 230° C., and more preferably about 170 to 220° C. The reaction pressure (total reactor pressure), including partial pressures of by-products, may be, for example, about 1.5 to 4 MPa.

In the reactor, the carbonylation reaction of methanol proceeds with forming an equilibrium between a liquid-phase reaction system and a gaseous-phase system. The liquid-phase reaction system contains the reactant(s) and the metal catalyst component, and the gaseous-phase system comprises carbon monoxide, reaction products (hydrogen, methane, and carbon dioxide), and vaporized lower boiling point components (e.g., methyl iodide, product acetic acid, and methyl acetate). The vapor components (vent gas) may be withdrawn from the top (or head) of the reactor (1), or may be subjected to an absorption treatment to recover carbon monoxide and/or hydrogen which may be then recycled to the reactor.

The reaction mixture (the crude reaction liquid) contains acetic acid, lower boiling point components or impurities, each having a boiling point lower than that of acetic acid (e.g., methyl iodide as a co-catalyst, methyl acetate as a reaction product of acetic acid and methanol, water, and acetaldehyde as a by-product), and higher boiling point components or impurities, each having a boiling point higher than that of acetic acid [e.g., a metal catalyst component (e.g., a rhodium catalyst), lithium iodide as a catalyst stabilizer, and a $C_{3-12}$alkanecarboxylic acid (e.g., propionic acid)]. Further, by-products derived from acetaldehyde (acetaldehyde derivatives) are also produced. The acetaldehyde derivatives may include, for example, other aldehydes such as butyraldehyde, crotonaldehyde, 2-ethylcrotonaldehyde, and 2-ethylbutyraldehyde; a ketone such as acetone or methyl ethyl ketone; an aldol condensation product thereof; and a $C_{2-12}$alkyl iodide such as ethyl iodide, propyl iodide, butyl iodide, pentyl iodide, or hexyl iodide. The by-products may also include a 3-hydroxyalkanal (e.g., 3-hydroxybutanal); formic acid or the $C_{3-12}$alkanecarboxylic acid (such as propionic acid, butanoic acid, hexanoic acid, heptanoic acid, or octanoic acid); a $C_{3-12}$alkyl alcohol such as butyl alcohol or 2-ethylbutyl alcohol; an ester of methanol or the above alkyl alcohol with acetic acid or the above carboxylic acid; an ether of methanol and/or the above alkyl alcohol (a dialkyl ether such as dimethyl ether); and methane and a hydrocarbon with two or more carbon atoms (e.g., a $C_{2-12}$alkane). These by-products are usually increased in proportion to the square to the cube of the concentration of acetaldehyde. Methane and a hydrocarbon with two or more carbon atoms (e.g., a $C_{2-12}$alkane) may be produced. Acetaldehyde and the by-products derived from acetaldehyde (for example, other aldehydes, the ketone, and the aldol condensation product) belong to permanganate reducing compounds (PRC's). Thus, it is preferred to separate and remove acetaldehyde, which is a main by-product, from the reaction mixture and to recover useful components (e.g., methyl iodide) from the process stream(s) for effective utilization. Incidentally, as used herein, methyl iodide is excluded from PRC's, although the $C_{2-12}$alkyl iodide as well as methyl iodide also belongs to PRC's.

According to the present invention, acetaldehyde is efficiently separable and removable to decrease the concentration of acetaldehyde in the reactor even in a continuous reaction. With the decrease in acetaldehyde concentration or the elimination of acetaldehyde, production of by-products derived from acetaldehyde is significantly prevented. For example, the whole liquid phase in the reactor may have a PRC (representatively, acetaldehyde) concentration of, for example, not more than 1000 ppm (e.g., 0 or detection limit to 700 ppm), preferably not more than 400 ppm (e.g., 5 to 300 ppm), and more preferably about 10 to 250 ppm throughout the whole process.

The space time yield of the objective carboxylic acid (acetic acid) in the reaction system may be, for example, about 5 mol/Lh to 50 mol/Lh, preferably about 8 mol/Lh to 40 mol/Lh, and more preferably about 10 mol/Lh to 30 mol/Lh.

The reaction system is an exothermic reaction system that accompanies heat generation, and the reaction temperature may be controlled (or regulated) by recycling of the condensate which has been cooled or from which heat has been removed, installation of a heat-removable (or heat-removing) unit or a cooling unit (e.g., a jacket). In order to remove part of the reaction heat, a vapor (vent gas) from the reactor may be cooled in a condenser, a heat exchanger, or other means to separate the vapor into liquid components and gaseous components, and the liquid components and/or the gaseous components may be recycled to the reactor.

(2) Flash Evaporation Step

In the flash evaporation step (2), a portion of the reaction mixture is continuously withdrawn from the reactor 1 and is introduced or fed to a flasher (catalyst separation column) (2) via a feed line 11 to separate the reaction mixture into a volatile phase (2A) and a less-volatile (2B); the volatile phase (2A) contains product acetic acid, methyl iodide, acetaldehyde, methyl acetate, water, or other compounds, and the less-volatile phase (2B) contains the rhodium catalyst and lithium iodide. At least a first portion of the volatile phase (2A) is fed to a distillation column of the first distillation step (3) via a feed line 22, and the less-volatile phase (2B) is recycled to the reactor of the reaction step (1) via a recycle line 21.

A second portion of the volatile phase (2A) may be cooled and condensed in a condenser C1 on a line 23. The resulting condensate may be held in a hold tank HT for recycling the condensate to the reaction step (reactor) (1). The cooled product (condensate and/or noncondensable component) in the condenser C1 may be fed to the liquid-liquid separation step (4) via a line 26 and may be held in a decanter (4) together with an overhead (3A) from the first distillation step (splitter column) (3), and a mixture of the cooled product and the overhead (3A) may be separated into two phases in the decanter (4).

[Condensation of Volatile Phase]

The second portion of the volatile phase (2A) may be fed, without condensation, to the second distillation step (5) directly or indirectly via the liquid-liquid separation step (4), or may be cooled and condensed in one or a plurality of condensers C1 to form two phases (an aqueous phase or an organic phase) for subjecting the aqueous phase or the organic phase (at least the aqueous phase) to the second distillation step (5) directly or indirectly via the liquid-liquid separation step (4). For example, the second portion of the volatile phase (2A) may optionally be condensed as described above (and optionally be liquid-liquid separated) and mix with the condensate obtained in the liquid-liquid separation step (4), and the mixture may be subjected to the second distillation step (5).

If necessary, the catalyst component (metal catalyst component) and the catalyst stabilizer or the reaction accelerator may be separated from the less-volatile phase (2B) by one or a plurality of steps and may be recycled to the reaction step (1).

The flash evaporation may include a thermostatic flash in which the reaction mixture is heated and depressurized, an adiabatic flash in which the reaction mixture is depressurized without heating, or a combination of these flash conditions. By such a flash evaporation, the reaction mixture may be separated into the vapor phase and the liquid phase. For example, the flash distillation may be carried out at a temperature of the reaction mixture of about 80 to 200° C., a pressure (absolute pressure) of the reaction mixture of about 50 to 1000 kPa (e.g., about 100 to 1000 kPa), preferably about 100 to 500 kPa, and more preferably about 100 to 300 kPa.

The flash evaporation may, for example, be carried out at a temperature of about 100 to 250° C. (e.g., about 110 to 200° C.), preferably about 120 to 180° C. (e.g., about 125 to 170° C.), and more preferably about 130 to 160° C. The pressure (gauge pressure) may be about 0.01 to 1 MPa (e.g., about 0.03 to 1 MPa), preferably about 0.05 to 0.5 MPa, and more preferably about 0.08 to 0.3 MPa (e.g., about 0.1 to 0.2 MPa). The less-volatile phase or the catalyst liquid mixture may have a temperature of, for example, about 80 to 200° C. (e.g., about 90 to 180° C.), preferably about 100 to 170° C. (e.g., about 120 to 160° C.), and more preferably about 130 to 160° C.

(3) First Distillation Step (Splitter Column)

In the first distillation step (splitter column) (3), the volatile phase (2A) is separated into a first overhead (3A), an acetic acid stream (3B), and a bottom stream (3C); the first overhead (3A) (overhead gas, lower boiling point stream or lower boiling point fraction) is withdrawn from a top or upper position (or part) of the column via a withdrawing line 32, the acetic acid stream (3B) is side-cut via a line 38 and mainly contains acetic acid, and the bottom stream (3C) (higher boiling point stream or higher boiling point fraction) is withdrawn from a bottom or lower part of the column via a bottom line 31. The proportion of the first overhead stream or overhead (3A) may be about 35 to 50% by weight in the whole volatile phase (2A).

The first overhead stream (3A), which corresponds to a mixed composition (3A), contains at least both permanganate reducing compound (PRC) and methyl iodide. The PRC contains at least by-product acetaldehyde. The first overhead stream (3A) usually contains methyl acetate and practically contains acetic acid, methanol, water, dimethyl ether, by-products derived from acetaldehyde (e.g., an aldehyde such as crotonaldehyde or butyraldehyde; an acetaldehyde derivative such as a $C_{2-12}$alkyl iodide or a $C_{3-12}$alkanecarboxylic acid; and a $C_{2-12}$alkane).

The acetic acid stream or side-cut stream (3B) is further fed to a purification step by a distillation column or other means (not shown) to remove water or higher boiling point impurities or other impurities from the stream (3B), thus producing purified acetic acid with a high purity. The liquid stream (3C) usually contains at least water and acetic acid and also practically contains methanol, propionic acid, or other compounds. The liquid stream (3C) may contain an entrained metal catalyst component. The liquid stream (3C) may be discharged via the line 31, or a portion or whole of the liquid stream (3C) may be recycled to the reaction step (reactor) (1) via a line 90.

The process of the present invention can be applied to the mixed composition or overhead stream which contains at least a PRC and methyl iodide. The first overhead (3A) may be subjected to the second distillation step (5) in a gaseous form. In a preferred embodiment, PRC's are effectively extracted with a small amount of the extractant in a small extraction space, and the process is effectively applied to the mixed composition or overhead stream (3A) which contains a high concentration of at least methyl iodide (in particular, high concentrations of both at least methyl iodide and PRC's). Incidentally, the mixed composition or overhead stream (3A) may have an increased water concentration. Thus, as shown in FIG. 1, by a preceding step or unit operation [e.g., the distillation step (3), the liquid-liquid separation step (4)], the mixed composition (3A) in which methyl iodide is (in particular, both methyl iodide and PRC's are) concentrated is produced. In this embodiment, the mixed composition (3A) is condensed and biphasically separated in the liquid-liquid separation step (4), and the resulting organic phase and/or aqueous phase is subjected to the second distillation step (5).

The internal temperature of the distillation column (splitter column) of the first distillation step (3) depends on an internal pressure thereof. At the internal pressure of an atmospheric pressure (1 atm=about 0.1 MPa), the distillation column may have a column top temperature of, for example, about 20 to 100° C. (e.g., about 30 to 80° C.) and preferably about 40 to 70° C. (e.g., about 50 to 60° C.), or may have a column bottom temperature of, for example, about 40 to 120° C. (e.g., about 50 to 100° C.) and preferably about 60 to 90° C. (e.g., about 70 to 85° C.). The distillation column may have a pressure of, for example, about 0.1 to 0.5 MPa, preferably about 0.2 to 0.4 MPa, and more preferably about 0.25 to 0.35 MPa in terms of absolute pressure.

The distillation column may have a theoretical stage or plate (or the number of theoretical stages or plates) of, for example, about 2 to 100 (e.g., about 5 to 70) and preferably about 7 to 50 (e.g., about 10 to 30). The reflux ratio of the distillation column may be infinity or may be, for example, about 1 to 5000 (e.g., about 10 to 4000) and preferably about 100 to 3000 (e.g., about 500 to 2000).

The internal temperature of the distillation column (splitter column) of the first distillation step (3) depends on an internal pressure thereof. At the internal pressure of an atmospheric pressure (1 atm=about 0.1 MPa), the distillation column may have a column top temperature of, for example, about 50 to 180° C. (e.g., about 70 to 170° C.) and preferably about 80 to 160° C. (e.g., about 90 to 140° C.), or may have a column bottom temperature of, for example, about 60 to 200° C. (e.g., about 80 to 180° C.) and preferably about 90 to 170° C. (e.g., about 100 to 160° C.). The distillation column may have a pressure (gauge pressure) of, for example, about 0.05 to 0.5 MPa, preferably about 0.08 to 0.4 MPa, and more preferably about 0.1 to 0.3 MPa.

The distillation column may have a theoretical stage or plate of, for example, about 2 to 100 (e.g., about 5 to 70) and preferably about 7 to 50 (e.g., about 10 to 30). The reflux ratio of the distillation column may be infinity or may be, for example, about 1 to 1000 (e.g., about 5 to 500) and preferably about 10 to 100 e.g., about 15 to 50).

(4) Condensation/Liquid-Liquid Separation Step

The first overhead (3A) from the first distillation step (splitter column or distillation column) (3) is cooled and condensed in a condenser C2 on a withdrawing line 32, and the condensate is biphasically separable into an aqueous phase rich in acetaldehyde and an organic phase rich in methyl iodide in a decanter (a decanter apparatus, a storage container) (4). A portion of the condensate (the aqueous phase and/or the organic phase) is returned to the splitter column (3) via a reflux line 42 (42a, 42b) for reflux. At least a portion of the aqueous phase is fed to a distillation column of the second distillation step (5), and at least a portion of the organic phase is recycled to the reaction step (1) via a line 41. In the embodiment shown in FIG. 1, a portion of the aqueous phase is returned to the splitter column (3) via the reflux line 42b for reflux, the residual portion of the aqueous phase is fed to the distillation column of the second distillation step (5) via a feed line 43b, a first portion of the organic phase is returned to the splitter column (3) via the reflux line 42a for reflux, and a second portion of the organic phase is fed to the distillation column of the second distillation step (5) via a feed line 44, and the residual portion of the organic phase is recycled to the reaction step (1) via the line 41.

Incidentally, to the distillation column of the second distillation step (5) may be fed the aqueous phase (a portion or the whole of the aqueous phase) or may be fed at least a portion of the organic phase (or the whole organic phase), as far as the side-cut stream (5B) is liquid-liquid (or biphasically) separable. Each of the aqueous phase and the organic phase may have a methyl iodide concentration of, for example, not less than 1.5% by weight (e.g., about 2 to 99% by weight, preferably about 3 to 95% by weight, and more preferably about 5 to 90% by weight). In a preferred embodiment, at least a portion of the organic phase (the organic phase rich in methyl iodide) is usually fed to the distillation column of the second distillation step (5), and at least a portion of the aqueous phase may be fed to the distillation column of the second distillation step (5).

In addition to the liquid-liquid separation step (decanter) (4) for temporarily holding or retaining the condensate and biphasically separating the condensate, a buffer tank for temporarily holding (or retaining) the condensate (the separated lower phase or upper phase) in the decanter (4) may optionally be utilized for suppressing the flow rate fluctuation of the process stream.

The condensate (as well as the aqueous phase and the organic phase) may have a temperature of, for example, about 20 to 110° C. (e.g., about 25 to 90° C.) and preferably about 30 to 80° C. (e.g., about 35 to 70° C.).

[Liquid-Liquid Separable/Condensable Gaseous Phase]

In the liquid-liquid separation step (4), a gas (off-gas) produced from the process may be condensed to separate the gaseous phase into two liquid phases; the gas produced from the process includes, for example, a gaseous phase (overhead) that is produced from at least one step selected from the group consisting of the reaction step (1), the flash evaporation step (2), the first distillation step (3), and the succeeding distillation steps (5), (7) and (8) [e.g., at least the first distillation step (3)] and contains at least acetaldehyde and methyl iodide.

[Plurality of Condensation Steps]

Among acetic acid, methyl acetate, methyl iodide, methanol, water, acetaldehyde, or other compounds, acetaldehyde has a boiling point close to that of methyl iodide and has the lowest boiling point. Thus, in a case where the first overhead stream (3A) is cooled stepwise in a plurality of condensers (a plurality of condensers successively lower in cooling temperature) to form a plurality of condensates successively lower in temperature, a condensate formed by a subsequent condenser has a higher concentration of acetaldehyde, which is a lower boiling point component, compared with a process liquid (a condensate) formed by a first condenser. Moreover, in a case where the first overhead stream (3A) is cooled stepwise in such a plurality of condensers, in the first condenser the first overhead stream (3A) is separable into a first condensate and a first gas fraction (noncondensable fraction) having a high acetaldehyde concentration, in a second condenser the first gas fraction is separable into a second condensate having a high acetaldehyde concentration and a second gas fraction (noncondensable fraction). Accordingly, a condensate having a high concentration of acetaldehyde may be fed to the second distillation step (5) to separate acetaldehyde from the condensate.

The gas fraction (noncondensable fraction) in the condenser(s) may be fed as a vent gas or off-gas (exhaust gas) to an absorption system to further collect or recover a useful component such as methyl iodide.

[Water Extraction and Liquid-Liquid Separation]

The process shown in FIG. 1 may further comprise, in addition to the liquid-liquid separation step (4), an water extraction step for bringing the first overhead stream (3A) to contact with water [or subjecting the first overhead stream (3A) to water extraction] to separate the first overhead stream (3A) into an organic phase rich in methyl iodide and an aqueous phase rich in acetaldehyde. In the extraction step, the first overhead stream (3A) may be brought to directly contact with water to give an acetaldehyde extract and may optionally be separated into an aqueous phase and an organic phase. In order to improve the extraction efficiency, the aqueous phase and/or the organic phase separated in the liquid-liquid separation step (4) may be brought to contact with water to form an acetaldehyde extract. At least one of the aqueous phase and the organic phase formed by the water extraction may be subjected to the second distillation step (5). The organic phase, which is rich in methyl iodide, is usually subjected to the second distillation step (5). The aqueous phase, which is rich in acetaldehyde, may be used as an extractant for the second distillation step (5) or may be fed to a concentration zone between the top of the column (the zeroth plate when the uppermost plate is the first plate) and a plate that is one plate upper than the side-cut stream (5B) (or side-cut plate).

The distillation of the overhead stream or mixed composition (3A) forms the side-cut stream (5B), which is liquid-liquid separable. The mixed composition (3A) may biphasically be separable. In a case where the mixed composition (3A) is biphasically separable, at least a portion of the organic phase, at least a portion of the aqueous phase, or a feed liquid containing the mixture of the organic phase and the aqueous phase can be fed to the distillation step (5). Thus, in the mixed composition (3A), the concentrations of methyl iodide, PRC's, water, or other compounds can be selected from wide concentration ranges.

Hereinafter, with reference to compositions of process streams, concentrations of typical components (acetaldehyde, methyl iodide, methyl acetate, acetic acid, water, and dimethyl ether) will be described, although the process streams inevitably contain other components (including impurities) as described below. The process streams may include the mixed composition (3A) and phases (phasically) separated therefrom, the second overhead stream (5A), the side-cut stream (5B) and phases (phasically) separated therefrom, overhead streams (7A) (8A) or condensates thereof, and bottom liquid streams (7B) (8B). As used herein, each process stream (or each phase), including impurities, has a total amount of 100% by weight on the basis of weight. The term "concentration of PRC's" may be the concentration of each one of PRC's or may be the concentration of all PRC's (or the total concentration of PRC's). The concentration of PRC's is simply referred to as "PRC concentration". Representative PRC's include acetaldehyde.

The mixed composition (3A) (a homogeneous liquid, or a mixture of an aqueous phase and an organic phase) may have a PRC (representatively, acetaldehyde) concentration of, for example, about 10 ppm to 10% by weight (e.g., about 100 ppm to 5% by weight) and preferably about 500 ppm to 1% by weight (e.g., about 0.1 to 0.5% by weight). According to the present invention, small amounts of PRC's (e.g., acetaldehyde) can be separated effectively, and thus the mixed composition (3A) may have a PRC (e.g., acetaldehyde) concentration of about 100 to 5000 ppm (e.g., about 500 to 3000 ppm) and usually about 750 to 2500 ppm (e.g., about 1000 to 2000 ppm). The mixed composition (3A) may have a methyl iodide concentration of, for example, about 10 to 85% by weight (e.g., about 25 to 80% by weight) and preferably about 40 to 75% by weight (e.g., about 50 to 70% by weight). The mixed composition (3A) may have a methyl acetate concentration of, for example, about 0 to 30% by weight (e.g., about 0.1 to 25% by weight) and preferably about 1 to 20% by weight (e.g., about 5 to 20% by weight) or may have a methyl acetate concentration of about 7 to 17% by weight (e.g., about 10 to 15% by weight). The mixed composition (3A) may have an acetic acid concentration of, for example, about 0 to 12% by weight (e.g., about 0.1 to 10% by weight) and preferably about 0.5 to 8% by weight (e.g., about 1 to 7% by weight); or may have an acetic acid concentration of about 1 to 5% by weight (e.g., about 1 to 3% by weight). The mixed composition (3A) may have a water concentration of, for example, not less than 1% by weight (e.g., about 5 to 87% by weight), preferably not less than 10% by weight (e.g., about 15 to 85% by weight), and more preferably not less than 20% by weight (e.g., about 30 to 83% by weight); or may have a water concentration of about 5 to 50% by weight (e.g., about 10 to 40% by weight) and preferably about 15 to 35% by weight (e.g., about 17 to 30% by weight). The mixed composition (3A) may have a dimethyl ether concentration of, for example, about 0 to 1% by weight (e.g., about 1 ppm to 0.5% by weight) and preferably about 5 ppm to 0.3% by weight (e.g., about 10 to 500 ppm). The mixed composition (3A) may have a methanol concentration of, for example, about 10 ppm to 5% by weight (e.g., about 50 ppm to 4% by weight) and preferably about 0.01 to 2.5% by weight (e.g., about 0.03 to 1.5% by weight).

In a case where the overhead stream or mixed composition (3A) is liquid-liquid separated (or forms an organic phase and an aqueous phase), the organic phase (the lines 41, 42a, and 44) may have a PRC (representatively, acetaldehyde) concentration of, for example, about 1 ppm to 10% by weight (e.g., about 100 ppm to 5% by weight) and preferably about 300 ppm to 2.1% by weight (e.g., about 500 ppm to 0.5% by weight) or may have a PRC concentration of about 100 to 5000 ppm (e.g., about 250 to 4000 ppm) and preferably about 500 to 3000 ppm (e.g., about 1000 to 2500 ppm). The organic phase may have a methyl iodide concentration of, for example, about 10 to 95% by weight (e.g., about 30 to 93% by weight), preferably about 50 to 90% by weight (e.g., about 70 to 90% by weight), and more preferably about 75 to 85% by weight (e.g., about 80 to 85% by weight); or may have a methyl iodide concentration of, for example, not less than 10% by weight (e.g., about 15 to 90% by weight), preferably not less than 20% by weight (e.g., about 25 to 90% by weight), more preferably not less than 30% by weight (e.g., about 30 to 80% by weight), and particularly about 40 to 70% by weight (e.g., about 50 to 65% by weight). The organic phase may have a methyl acetate concentration of, for example, about 1 to 30% by weight (e.g., about 3 to 25% by weight), preferably about 5 to 20% by weight (e.g., about 7 to 16% by weight), and more preferably about 10 to 18% by weight. The organic phase of the mixed composition (3A) may have an acetic acid concentration of, for example, about 0 to 10% by weight (e.g., about 0.1 to 7% by weight) and preferably about 0.3 to 5% by weight (e.g., about 0.5 to 3% by weight) or may have an acetic acid concentration of about 1 to 5% by weight (e.g., about 1.5 to 3% by weight). The organic phase may have a water concentration of, for example, about 0 to 50% by weight (e.g., about 0.01 to 40% by weight), preferably about 0.1 to 30% by weight (e.g., about 0.2 to 20% by weight), and more preferably about 0.5 to 10% by weight (e.g., about 1 to 5% by weight); or may have a water concentration of about 0 to 5% by weight (e.g., about 0.1 to 3% by weight) and preferably about 0.3 to 2% by weight (e.g., about 0.5 to 1.5% by weight). The organic phase may have a dimethyl ether concentration of, for example, about 0 to 1% by weight (e.g., about 1 ppm to 0.5% by weight), preferably about 5 ppm to 0.3% by weight (e.g., about 10 ppm to 0.1% by weight), and more preferably about 10 to 100 ppm (e.g., about 15 to 70 ppm). The organic phase may have a methanol concentration of, for example, about 10 ppm to 4% by weight (e.g., about 50 ppm to 3% by weight) and preferably about 0.01 to 1% by weight (e.g., about 0.03 to 0.5% by weight).

In a case where the overhead stream or mixed composition (3A) is liquid-liquid separated (or forms an organic phase and an aqueous phase), the aqueous phase (lines 43a and 43b) may have a PRC (representatively, acetaldehyde) concentration of, for example, about 500 ppm to 30% by weight (e.g., about 1000 ppm to 25% by weight), preferably about 2000 ppm to 20% by weight (e.g., about 2500 ppm to 15% by weight), and more preferably about 3000 ppm to 5% by weight (e.g., about 3000 ppm to 5% by weight). The aqueous phase may have a methyl iodide concentration of, for example, about 0.1 to 30% by weight (e.g., about 1 to 25% by weight) and preferably about 3 to 20% by weight (e.g., about 5 to 15% by weight); or may have a methyl iodide concentration of not less than 1.5% by weight (e.g., about 2 to 50% by weight), not less than preferably 2% by weight (e.g., about 3 to 40% by weight), and more preferably not less than 4% by weight (e.g., about 5 to 30% by weight); or may have a methyl iodide concentration of about 0.1 to 10% by weight (e.g., about 0.5 to 7% by weight) and more preferably about 1 to 5% by weight (e.g., about 1.5 to 3.5% by weight). The aqueous phase may have a methyl acetate concentration of, for example, about 1 to 30% by weight (e.g., about 3 to 25% by weight), preferably about 5 to 20% by weight (e.g., about 7 to 15% by weight), or about 5 to 10% by weight. The aqueous phase may have an acetic acid concentration of, for example, about 5 to 60% by weight (e.g., about 10 to 50% by weight), preferably about 20 to 40% by weight (e.g., about 25 to 35% by weight), or may have an acetic acid concentration of about 15 to 35% by weight (e.g., about 20 to 30% by weight). The aqueous phase may have a water concentration of, for example, about 10 to 90% by weight (e.g., about 25 to 80% by weight) and preferably about 30 to 75% by weight (e.g., about 40 to 70% by weight). The aqueous phase may have a dimethyl ether concentration of, for example, about 0 to 0.3% by weight (e.g., about 1 ppm to 0.2% by weight) and preferably about 5 ppm to 0.1% by weight (e.g., about 10 to 500 ppm). The aqueous phase may have a methanol concentration of, for example, about 100 ppm to 7% by weight (e.g., about 500 ppm to 5% by weight) and preferably about 0.1 to 3% by weight (e.g., about 0.3 to 2% by weight).

The acetic acid stream or side-cut stream (3B) may have a PRC (such as acetaldehyde) concentration of, for example, about 0 to 2000 ppm (e.g., about 0 to 1000 ppm), preferably about 0 to 500 ppm (e.g., about 1 to 100 ppm), and more preferably about 0 to 50 ppm or may have the PRC concentration substantially not more than detection or measurable limit. The acetic acid stream (3B) may have a methyl iodide concentration of, for example, about 0 to 15% by weight (e.g., about 0.3 to 10% by weight) and preferably about 0.5 to 7% by weight (e.g., about 1 to 5% by weight). The acetic acid stream (3B) may have a methyl acetate concentration of, for example, about 0 to 15% by weight (e.g., about 0.3 to 10% by weight) and preferably about 0.5 to 8% by weight (e.g., about 1 to 5% by weight). The acetic acid stream (3B) may have a water concentration of, for example, about 0 to 15% by weight (e.g., about 0.3 to 10% by weight) and preferably about 0.5 to 5% by weight (e.g., about 1 to 3% by weight). The acetic acid stream (3B) may have a dimethyl ether concentration of, for example, about 0 to 1000 ppm (e.g., about 0 to 100 ppm) and preferably about 0 to 50 ppm (e.g., about 0 to 10 ppm) or may have a dimethyl ether concentration substantially not more than detection limit. The acetic acid stream (3B) may have a methanol concentration of, for example, about 0 to 1% by weight (e.g., about 0 to 0.5% by weight), preferably about 0 to 5000 ppm (e.g., about 0 to 1000 ppm), and more preferably about 0 to 100 ppm or may have a methanol concentration substantially not more than detection limit. The acetic acid stream or side-cut stream (3B) contains these components, inevitable contaminants (including impurities or by-products), and acetic acid as the remainder. The acetic acid stream (3B) may have an acetic acid concentration of, for example, about 87 to 99% by weight (e.g., about 88 to 98% by weight) and preferably about 90 to 97% by weight (e.g., about 90 to 95% by weight).

The bottom liquid stream (higher boiling point stream or higher boiling point fraction) (3C) (the line 31) may have a PRC (such as acetaldehyde) concentration of, for example, about 0 to 2000 ppm (e.g., about 0 to 1000 ppm), preferably about 0 to 500 ppm (e.g., about 1 to 100 ppm), and more preferably about 0 to 50 ppm or may have the PRC concentration substantially not more than detection limit. The bottom liquid stream (3C) may have a methyl iodide concentration of, for example, about 0 to 15% by weight (e.g., about 0.01 to 10% by weight), preferably about 0.1 to 8% by weight (e.g., about 0.2 to 5% by weight), and more preferably about 0.5 to 3% by weight. The bottom liquid stream (3C) may have each of a methyl acetate concentration and water concentration of, for example, about 0 to 15% by weight (e.g., about 0.1 to 10% by weight), preferably about 0.3 to 8% by weight (e.g., about 0.5 to 5% by weight), and more preferably about 0.7 to 3% by weight (e.g., about 1 to 2% by weight). The bottom liquid stream (3C) may have an acetic acid concentration of, for example, about 60 to 99% by weight (e.g., about 70 to 99% by weight), preferably about 80 to 98% by weight (e.g., about 85 to 98% by weight), and more preferably about 90 to 98% by weight. The bottom liquid stream (3C) may have a dimethyl ether concentration of, for example, about 0 to 1000 ppm (e.g., about 0 to 100 ppm) and preferably about 0 to 50 ppm (e.g., about 0 to 10 ppm) or may have a dimethyl ether concentration substantially not more than detection limit. The bottom liquid stream (3C) may have a methanol concentration of, for example, about 0 to 1% by weight (e.g., about 0 to 0.5% by weight), preferably about 0 to 5000 ppm (e.g., about 0 to 1000 ppm), and more preferably about 0 to 100 ppm or may have a methanol concentration substantially not more than detection limit.

(5) Second Distillation Step (Distillation Column)

In the second distillation step (distillation column) (5), the first overhead stream (3A) fed via the feed lines 43b, 44 [in the embodiment illustrated, the condensate from liquid-liquid separation step (4)] is distilled to form a concentration zone (a zone with high concentrations of PRC's (in particular, acetaldehyde) and methyl iodide) in the upper position of the distillation column. To the concentration zone, an extractant which can extract PRC's (in particular, acetaldehyde) preferentially to methyl iodide is added to extract at least PRC's (in particular, acetaldehyde), and an extraction mixture (liquefied fraction, falling liquid) falling from the concentration zone is withdrawn as a side-cut stream (5B) from the distillation column. The extraction mixture has a PRC (in particular, acetaldehyde) concentration significantly higher than the first overhead stream or mixed composition (3A) fed to the distillation column (5). Withdrawing the extraction mixture as the side-cut stream (5B) allows PRC's to be separated or removed effectively.

Assuming that the total number of plates of the distillation column is "100" and the bottom is the "zeroth" (0th) plate, the position (feed port, or feed plate or tray) at which the mixed composition or overhead stream (3A) [in the embodiment illustrated, the organic phase and/or the aqueous phase from the liquid-liquid separation step (4)] is fed to the second distillation column (5) may be selected from the range of about the 1st to the 70th plate from the bottom of the distillation column, and, for example, may be about the 1st to the 50th plate (e.g., about the 3rd to the 45th plate), preferably the 4th to the 40th plate (e.g., about 5th to the 35th plate) from the bottom of the distillation column. In other words, assuming that the height level of the distillation portion of the distillation column is "1", the mixed composition or overhead stream (3A) may, for example, be fed at a height level of about 0.01/1 to 0.7/1 (e.g., about 0.01/1 to 0.5/1), preferably about 0.03/1 to 0.45/1 (e.g., about 0.04/1 to 0.4/1), and more preferably about 0.05/1 to 0.35/1 from the bottom. For example, for a plate distillation column having the total actual number of stages (or plates) of 43, the feed plate to which the mixed composition (3A) is fed may be about the 1st to the 20th plate, preferably about the 2nd to the 15th plate, and more preferably about the 4th to the 10th plate from the bottom of the distillation column. For example, for a plate distillation column having the total actual number of stages (or plates) of 10, the feed plate to which the mixed composition (3A) is fed may be about the 1st to the 7th plate, preferably about the 1st to the 5th plate, and more preferably about the 1st to the 3rd plate from the bottom of the distillation column.

The distillation column of the distillation step (5) is provided with a receiving or holding unit, for example, a receiver (e.g., a chimney tray) (51); the unit permits the upward transfer of the vapor or evaporation fraction of the first overhead stream (3A) [in the embodiment illustrated, the condensate from the liquid-liquid separation step (4)] to the concentration zone and the holding of the whole amount of the extraction mixture (or falling liquid) falling from the concentration zone. Incidentally, the extraction mixture may be liquid-liquid separable in a receiving unit capable of receiving the falling liquid as a mixture of the raffinate (methyl iodide liquid) and the extract.

The receiver is disposed at an upper position than the feed port of the first overhead stream (3A) and a lower position than the addition port of the extractant. The receiver (e.g., a chimney tray) has a usual structure, for example, a tray capable of receiving the extraction mixture (liquid, falling liquid) falling from the concentration zone, and hollow cylindrical chimneys; each chimney projects or extends from the edge of the opening of the tray toward the top of the column (upwardly), and allows the vapor or evaporated fraction of the first overhead stream (3A) to rise or transfer to the concentration zone. The chimney has an upper opening to which a cover (a cowl or a cap) is attached; the cover permits the vapor or evaporation fraction to move upward or pass through. The receiver (e.g., a chimney tray) may be provided with a withdrawing port or withdrawing line for withdrawing a liquid in the tray. The structure of the receiver (e.g., chimney tray) is not limited to the structure described above. The chimney, if necessary the cover, may have a small pore permitting the vapor or evaporation fraction to pass through. The tray may have a funnel structure, a curved structure, or other structures. The receiver (chimney tray) may have an opening ratio (an area ratio of the openings relative to the whole surface of the tray) of about 5 to 90%, for example, about 10 to 50% (e.g., about 15 to 40%), and preferably about 15 to 35%.

In the distillation column (5) provided with such a unit or receiver (chimney tray), the extractant is added to the concentration zone formed above the receiver. The concentration zone is formed in a space between the feed port and the top of the column. Due to a low boiling point of acetaldehyde and that of methyl iodide, the concentration zone can be formed in an upper space (the top side of the column), in particular, a space in or near the top of the column. Thus, the receiver (e.g., a chimney tray) may be disposed at an upper position of the distillation column (5). The PRC's are extracted efficiently by withdrawing the side-cut stream (5B) from the concentration zone, and thus the position of the receiver [the position of a port withdrawing the side-cut stream (5B)] is practically upper than the feed port of the mixed composition (3A). The receiver [a port withdrawing the side-cut stream (5B)] is not limited to a particular position, and may be disposed at the same height level as the height level of the feed port (or feed plate) of the first overhead stream or mixed composition (3A) or may be disposed at a recovery zone lower than the feed port. Specifically, the height level of the receiver may be the same as that of the feed port of the first overhead stream or mixed composition (3A) or may be higher or lower than that of the feed port of the mixed composition (3A). In a case where the receiver is disposed at a position lower than the feed port of the first overhead stream or mixed composition (3A), the receiver is positioned at an upper than the bottom stream.

The height level of the receiver (e.g., a chimney tray) in the distillation column is upper than the feed part or feed tray of the first overhead stream (3A). According to the number of plates of the distillation column, the height level of the receiver (e.g., a chimney tray) is in between the uppermost plate of the column (the 1st plate from the top of the column) and a plate at least one plate upper than the feed part or feed tray of the first overhead stream (3A) or is positioned at or near the top (or head) of the column. Assuming that the total number of plates of the distillation column is 100, the position (height level) of the receiver may be selected from the range corresponding to about the 2nd to the 70th plate from the top of the distillation column, and, for example, may correspond to about the 2nd to the 60th plate (e.g., about the 2nd to the 45th plate), preferably about the 2nd to the 30th plate (e.g., about the 2nd to the 25th plate), and more preferably about the 2nd to the 10th plate (e.g., about the 2nd to the 7th plate) from the top of the distillation column. In other words, assuming that the height level of the distillation portion of the distillation column is "1", the receiver may be formed at a height level of about 0.02/1 to 0.7/1 (e.g., about 0.02/1 to 0.6/1), preferably about 0.02/1 to 0.45/1 (e.g., about 0.02/1 to 0.3/1), and more preferably about 0.02/1 to 0.25/1 (e.g., about 0.02/1 to 0.1/1) from the top of the distillation column. For example, in a case where the distillation column is a plate distillation column having the total actual number of stages (or plates) of 43, the receiver (e.g., a chimney tray) may be disposed in place of a plate between the uppermost plate of the top of the column (the 1st plate from the top of the column) or the top of the column and a plate that is positioned at at least one plate upper than the feed part or feed tray of the first overhead stream (3A) (for example, a plate that is at least 5 plates upper than the feed tray); or the receiver (e.g., a chimney tray) may be disposed in place of a plate between the uppermost plate of the top of the column and a plate that is positioned at 25 plates lower than the uppermost plate (the 25th plate) (preferably the 10th plate from the uppermost plate, more preferably the 5th plate from the uppermost plate, and particularly the 3rd plate from the uppermost plate). More specifically, the side-cut plate (receiver) of the side-cut stream (5B) may be positioned at the uppermost plate of the distillation column (the 1st plate), the 2nd or the 3rd uppermost plate (in particular, the uppermost plate or the 2nd uppermost plate).

In a case where the distillation column is a plate distillation column having the total actual number of stages (or plates) of 10, the receiver (e.g., a chimney tray) may be disposed in place of a plate between the uppermost plate of the top of the column (the 1st plate from the top of the column) or the column top and a plate that is positioned at at least one plate upper than the feed part or feed tray of the first overhead stream (3A) (for example, a plate that is at least 5 plates upper than the feed tray); or the receiver (e.g., a chimney tray) may be disposed in place of a plate between the uppermost plate of the top of the column and a plate that is positioned at 10 plates lower than the uppermost plate (the 10th plate) (preferably the 5th plate from the uppermost plate, more preferably the 2nd plate from the uppermost plate, and particularly the 1st plate from the uppermost plate). More specifically, the side-cut plate (receiver) of the side-cut stream (5B) may be positioned at the uppermost plate of the distillation column (the 1st plate), the 2nd or the 3rd uppermost plate (in particular, the uppermost plate or the 2nd uppermost plate).

The extractant can usually be added to the upper part of the distillation column (5) [for example, to the uppermost plate of the column, or between the top of the column and a plate that is positioned at at least one plate upper than the feed part or feed tray of the first overhead stream (3A)]. Assuming that the distillation column has the total number of plates of 100, the feed plate of the extractant may be a plate at or near the top of the distillation column (5), for example, about the 0th to the 50th plate (e.g., about the 1st to the 25th plate), preferably about the 1st to the 20th plate (e.g., about the 1st to the 15th plate), and more preferably about the 1st to the 10th plate from the top of the distillation column. In other words, assuming that the height level of the distillation portion of the distillation column is "1", the extractant may, for example, be fed at a height level of about 0/1 (the top of the column) to 0.5/1 (e.g., about 0.01/1 to 0.25/1), preferably about 0.01/1 to 0.2/1 (e.g., 0.01/1 to 0.15/1), and more preferably about 0.01/1 to 0.1/1 from the top of the column. For example, in a case where the distillation column is a plate distillation column having the total actual number of stages (or plates) of 43, the extractant may be added to a plate at or near the top of the distillation column (5) (e.g., the 0th to the 20th plate, preferably the uppermost to the 10th plate, more preferably the uppermost to the 5th plate, and particularly the uppermost to the 3rd plate). In a case where the distillation column is a plate distillation column having the total actual number of stages (or plates) of 10, the extractant may be added to a plate at or near the top of the distillation column (5) (e.g., the 0th to the 7th plate, preferably the uppermost to the 5th plate, more preferably the uppermost to the 3rd plate, and particularly the uppermost to the 2nd plate). In order to increase the extraction efficiency by countercurrently adding the extractant to the rising vapor or evaporation fraction, the extractant may usually be added to the uppermost plate of the distillation column (5). In order to increase the extraction efficiency, the extractant can be added in a droplet form, in particular, may be added by spraying or sprinkling. The extractant may have a temperature of, for example, about 0 to 60° C., preferably about 10 to 50° C., and more preferably about 20 to 40° C., or may have an ordinary temperature (e.g., about 15 to 25° C.). The extractant may be added as an extractant warmed or heated (for example, heated to about 30 to 150° C. and preferably about 50 to 110° C.) or in the form of vapor (including superheated vapor).

The extractant is capable of extracting PRC's (in particular, acetaldehyde) preferentially to methyl iodide. The extractant is preferably separable from the methyl iodide phase by liquid-liquid separation. Specifically, the preferred extractant can separate the extraction mixture (5B) into an upper phase and a lower phase. In particular, the extractant preferably includes an aqueous extractant containing at least water, for example, water, and a mixed solvent containing water and a water-soluble organic solvent [e.g., an alcohol (a monool) such as methanol, a glycol such as ethylene glycol, a polyhydric alcohol such as glycerin, acetone, an ester, and an ether]. Among these extrantants, water is preferred. Feeding water as the extractant keeps or maintains the extraction mixture (or droplet extraction mixture) in a liquid-liquid separated state to advantageously separate the extraction mixture into two phases.

The extractant may contain water and at least one component selected from the group consisting of PRC's, methyl iodide, acetic acid, methyl acetate, dimethyl ether, and a component present in the process (all components including the impurities described above). Such an extractant may be an aqueous solvent produced in the process [for example, an aqueous phase 43a produced in the liquid-liquid separation step (4) of the first overhead stream (3A), an aqueous process stream such as the extracts 62, 67, and 69 produced in the second liquid-liquid separation step (6) (e.g., an acetaldehyde-containing aqueous process stream), and other acetaldehyde-containing aqueous process streams (e.g., an aqueous phase formed by extracting PRC's with water)]. The extractant may also include an aqueous solution (for example, an aqueous solution containing acetaldehyde and methyl iodide) obtainable by absorption-treating an off-gas with water, the off-gas being produced from the process. The off-gas may include, for example, off-gases produced in a variety of unit operations in the process, such as off-gases produced in the reactor (1), the flash evaporator (2), the first distillation column (3), the second distillation column (5) or the separation unit 6a, the third distillation column (7), the fourth distillation column (8), or others.

According to the present invention, not the whole of the distillation column but a space (or zone) between the addition port (or position) of the extractant and the receiver (side-cut position) can be used as an extraction space (an extraction zone); the vapor or vaporized fraction in the concentration zone (in particular, at least acetaldehyde and methyl iodide contained in the zone) can be extracted with the extractant. Thus PRC's (in particular, acetaldehyde) can be extracted efficiently with a smaller amount of the extractant relative to the amount of the extractant used for a process withdrawing the extraction mixture (5B) as the bottom stream (5C). For example, the weight ratio of the flow rate of the extractant relative to the flow rate of the first overhead stream (3A) (in terms of liquid stream) [the former/the latter] may be selected from a range of about 0.0001/100 to 100/100 (e.g., about 0.001/100 to 50/100) or may usually be about 0.0001/100 to 20/100 (e.g., about 0.001/100 to 10/100), preferably about 0.01/100 to 8/100, and more preferably about 0.1/100 to 5/100. Thus the extraction mixture or the falling liquid [or the side-cut stream (5B)] in the distillation column can form a liquid stream [or side-cut stream (5B)] having a low extractant content; the biphasically separable liquid stream can form an aqueous phase (a small amount of an aqueous phase or extract) and an organic phase (a large amount of an organic phase or raffinate).

Incidentally, according to the conventional combination of acetaldehyde (AD)-removing distillation with water extraction, a PRC-concentrated organic phase (or methyl iodide phase) is extracted with substantially the same amount of an extraction water as the PRC-concentrated organic phase. In contrast, according to the present invention, the amount of the extraction water is about 0.1% to 10% of the PRC-concentrated organic phase (or methyl iodide phase). Thus, in a case where the PRC concentration in the organic phase is substantially the same, the PRC concentration in the aqueous phase can significantly be increased compared with the conventional water extractive distillation. In other words, PRC's can be extracted with water efficiently even if the organic phase has a low PRC concentration, and thus the separation zone (the actual number of stages (or plates) or the number of theoretical stages (or plates)) of the distillation column may be reduced compared with the conventional art, removing acetaldehyde with a lower cost. Meanwhile, irrespective of the amount of the organic phase, the organic phase has a high (substantially equivalently high) methyl iodide concentration; under the same acetaldehyde (AD) concentration in the aqueous phase, the concentration of methyl iodide (MeI) dissolved in the aqueous phase is low and is hardly changed regardless of the amount ratio of the aqueous phase and the organic phase after the extraction. Thus, according to the present invention, even though an extremely smaller amount of the extractant relative to the amount of the organic phase to be extracted is used, the ratio (MeI/AD ratio) of methyl iodide (MeI) relative to acetaldehyde (AD) can be reduced compared with the conventional combination of the acetaldehyde-removing distillation with water extraction, and PRC's can be removed effectively under the condition of reducing a loss of methyl iodide to the outside of the system with a small distillation zone and a low cost.

Incidentally, Examples of Patent Document 2 (TABLE 2) disclose that, in water extractive distillation using a second distillation column, water is fed to a top of the column, a feed liquid having an acetaldehyde concentration of 31% by weight is distilled in the second distillation column, and an aqueous bottom stream is withdrawn from a bottom of the column, and that the acetaldehyde concentration of 31% by weight in the feed liquid is reduced to 22.4% by weight in the bottom stream. However, the water extractive distillation described in Patent Document 2 requires 100 or more times the amount of the extractant that the second distillation step (5) according to the present invention. Incidentally, according to the present invention, methyl iodide can be withdrawn as the overhead stream or mixed composition (3A) from a side the distillation column (5), whereas according to Patent Document 2, methyl iodide is mainly withdrawn from the top of the column; both are quite different in separation manner of methyl iodide. According to the present invention, a bottom stream having a high methyl iodide concentration is obtainable by withdrawing the side-cut stream from the distillation column (5) and returning the withdrawn stream to the distillation column (5). If, in accordance with the process of Patent Document 2, the amount of the extractant (e.g., water) fed to the top of the distillation column is 100 or more times as large as that of the extractant in the present invention (for example, the amount of the extractant is substantially the same as or larger than the amount of the feed liquid), the ratio of the bottom rate/the feed rate in accordance with Patent Document 2 is 100 or more times as high as the side-cut aqueous phase rate/feed rate in the present invention. Thus, in a case where the bottom aqueous stream is directly discharged to the outside of the system or is further distilled for separation of acetaldehyde and methyl iodide from water, at least 5 to 10 or more times the amount of methyl iodide is discharged to the outside of the system in comparison with the present invention due to methyl iodide dissolved in the bottom stream (aqueous stream). Moreover, differently from the present invention, according to Patent Document 2, most of feed methyl iodide is withdrawn from the top of the column, and thus a large amount of energy is required, which is uneconomic.

Further, since the extraction mixture not as the lower stream or bottom stream (5C) but as the side-cut stream (5B) is withdrawn from a withdrawing port of a receiver (e.g., a chimney tray), PRC's (in particular, acetaldehyde) and methyl iodide can be separated from each other even if the number of plates of the distillation column is significantly decreased. For example, assuming that the total number of plates of the distillation column is 100 in the conventional process, the number of plates of the distillation column in the present invention can be reduced to about 5 to 80 (e.g., about 10 to 80), preferably about 7 to 70 (e.g., about 12 to 60), more preferably about 8 to 50 (e.g., about 15 to 50), and particularly about 10 to 40 (e.g., about 20 to 40). Even if a distillation column has about 8 to 20 (e.g., about 10 to 15) plates, PRC's and methyl iodide can effectively be separated. In other words, assuming that usual distillation column has a separation space (distillation space) of "100", a distillation column having a separation space of, for example, about 5 to 80 (e.g., about 10 to 80), preferably about 7 to 50 (e.g., about 8 to 30), and more preferably about 10 to 30 (e.g., about 10 to 20) also allows effective separation of PRC's and methyl iodide from each other.

In a case where a membrane separation of PRC's is further conducted following the extractive distillation in the distillation column (5), assuming that the total number of plates of the distillation column (5) is 100 as the same as that of the distillation column of Patent Document 2, the number of plates of the distillation column in the present invention can be reduced to about 5 to 20. For example, in a case where an aqueous phase having a higher methyl iodide/PRC's ratio than a process stream prior to the PRC's removal is withdrawn in the extractive distillation by the distillation column (5) and then PRC's are separated from the withdrawn phase in a succeeding step (e.g., membrane separation), the number of plates of the distillation column (5) can further significantly be reduced as described above.

From the distillation column, at least a portion of the extraction mixture (5B) is withdrawn. The extraction mixture retained in the tray may usually be withdrawn continuously. Specifically, the extraction mixture can be withdrawn from the distillation column depending on the amount of the liquid falling from the concentration zone (the whole amount of the falling liquid).

In such a process, even if the first overhead stream (3A) contains an amphipathic component (such as methyl acetate or acetic acid) having a high affinity with both PRC's (such as acetaldehyde) and methyl iodide, the PRC's (such as acetaldehyde) in the first overhead stream (3A) can effectively be extracted to the side-cut stream or extraction mixture (5B), and thus the PRC's (such as acetaldehyde) can be separated and removed. For example, the acetaldehyde concentration in the side-cut stream (5B) is higher than that in the first overhead stream (3A) and that of the bottom stream (5C). For example, the PRC (such as acetaldehyde) concentration in the side-cut stream (5B) [the aqueous phase of the side-cut stream (5B)] is about 10 to 1000 times (e.g., about 20 to 800 times), preferably about 30 to 500 times (e.g., about 50 to 200 times), and more preferably about 50 to 170 times (e.g., about 60 to 150 times) as large as that in the first overhead stream (gaseous stream or a condensate stream thereof) (3A).

The ratio of acetaldehyde relative to methyl iodide in the side-cut stream (5B) is higher than that in the first overhead stream (3A) and is higher than that in the bottom stream (5C).

The internal temperature of the distillation column of the second distillation step (5) depends on an internal pressure thereof. At the internal pressure of an atmospheric pressure, the distillation column may have a column top temperature of, for example, about 15 to 120° C. (e.g., about 18 to 100° C.), preferably about 20 to 90° C. (e.g., about 20 to 80° C.), and more preferably about 20 to 70° C. (e.g., about 25 to 70° C.), or may have a column bottom temperature of, for example, about 35 to 150° C. (preferably about 40 to 120° C.). The distillation column may have a column top pressure (absolute pressure) of, for example, about 0.1 to 0.5 MPa. In the second distillation step (5), other distillation conditions (e.g., the number of theoretical stages of the distillation column, and the reflux ratio) may be the same as those in the first distillation step (3).

The second overhead stream (5A) (a mixture of an aqueous phase and an organic phase when the stream is separated into these phases; a mixture in a line 53, a mixture of a stream in a line 61 and a stream a line 62) may have a PRC (such as acetaldehyde) concentration of, for example, about 1 to 75% by weight (e.g., about 10 to 70% by weight), preferably about 20 to 65% by weight (e.g., about 25 to 60% by weight), and more preferably about 30 to 55% by weight (e.g., about 35 to 50% by weight); or may have a PRC concentration of about 50 to 95% by weight (e.g., about 75 to 90% by weight) and preferably about 80 to 90% by weight. The second overhead stream (5A) may have a methyl iodide concentration of, for example, about 1 to 85% by weight (e.g., about 10 to 80% by weight), preferably about 20 to 80% by weight (e.g., about 30 to 75% by weight), and more preferably about 40 to 75% by weight (e.g., about 50 to 70% by weight); or may have a methyl iodide concentration of about 5 to 30% by weight (e.g., about 7 to 25% by weight) and preferably about 10 to 20% by weight. The second overhead stream (5A) may have a methyl acetate concentration of, for example, about 0 to 10% by weight (e.g., about 0.01 to 7% by weight), preferably about 0.02 to 5% by weight (e.g., about 0.03 to 2% by weight), and more preferably about 0.05 to 1% by weight (e.g., about 0.1 to 0.5% by weight), or may have a methyl acetate concentration of about 0.2 to 1% by weight (e.g., about 0.3 to 0.7% by weight). The second overhead stream (5A) may have an acetic acid concentration of, for example, about 0 to 5% by weight (e.g., about 1 ppm to 3% by weight) and preferably about 0 to 2% by weight (e.g., about 10 ppm to 1% by weight), or may have an acetic acid concentration substantially not more than detection limit. Further, the second overhead stream (5A) may have a water concentration of, for example, about 0 to 30% by weight (e.g., about 0.02 to 10% by weight), preferably about 0.05 to 5% by weight (e.g., about 0.07 to 1% by weight), and preferably about 0.1 to 0.5% by weight. The second overhead stream (5A) may have a dimethyl ether concentration of, for example, about 0 to 2.5% by weight (e.g., about 10 ppm to 2% by weight) and preferably about 100 ppm to 1.5% by weight (e.g., about 0.1 to 1% by weight). The second overhead stream (5A) may have a methanol concentration of, for example, about 0 to 0.5% by weight, preferably about 0 to 0.3% by weight, and more preferably about 0 to 2500 ppm (e.g., about 0 to 1000 ppm), or may have a methanol concentration substantially not more than detection limit. The reduction of the number of distillation stages (or plates) of the second distillation column (5) (for example, the reduction the actual number of stages (or plates) from 100 to not more than 15% (or to about 10 to 15)) may tend to increase the PRC (representatively acetaldehyde) concentration in the second overhead stream (5A) and to decrease the methyl iodide concentration in the second overhead stream (5A).

The second overhead stream (5A) (the line 53 just before a condenser C3) (a mixture of an aqueous phase and an organic phase when the second overhead stream is separated into these phases) may have a temperature at an atmospheric pressure of, for example, about 15 to 110° C. (e.g., about 18 to 90° C.) and preferably about 20 to 80° C. (e.g., about 20 to 70° C.).

The off-gas from the condenser C3 is rich in dimethyl ether, PRC's (in particular, acetaldehyde), and methyl iodide. The off-gas from the condenser C3 may have a PRC (such as acetaldehyde) concentration of, for example, about 1 to 75% by weight (e.g., about 10 to 70% by weight), and preferably about 20 to 65% by weight (e.g., about 30 to 60% by weight), or may have a PRC concentration of about 35 to 65% by weight. The off-gas may have a methyl iodide concentration of, for example, about 1 to 55% by weight (e.g., about 5 to 50% by weight) and preferably about 7 to 45% by weight (e.g., about 10 to 40% by weight). The off-gas may have a methyl acetate concentration of, for example, about 0.1 to 20% by weight (e.g., about 0.5 to 15% by weight) and preferably about 1 to 12% by weight (e.g., about 2 to 10% by weight). The off-gas may have an acetic acid concentration of, for example, about 0 to 5% by weight (e.g., about 0.0001 to 3% by weight), preferably about 0 to 2.5% by weight (about 0.001 to 2% by weight), and preferably about 0.01 to 1% by weight, or may have an acetic acid concentration substantially not more than detection limit. The off-gas may have a water concentration of, for example, about 0 to 5% by weight (e.g., about 0.01 to 2.5% by weight) and preferably about 0 to 2% by weight (e.g., about 0.1 to 1.5% by weight), or may have a water concentration substantially not more than detection limit. The off-gas may have a dimethyl ether concentration of, for example, about 0.1 to 90% by weight (e.g., about 1 to 80% by weight), preferably about 3 to 80% by weight (e.g., about 5 to 70% by weight), and more preferably about 10 to 60% by weight (e.g., about 20 to 50% by weight). The off-gas may have a methanol concentration of, for example, about 0 to 5% by weight (e.g., about 0.01 to 3% by weight) and preferably about 0 to 2.5% by weight (e.g., about 0.1 to 2% by weight).

The side-cut stream (5B) (a mixture of an aqueous phase and an organic phase when the stream is separated into these phases; a mixture in a line 63, a mixture of a stream in the line 61 and a stream in the line 62) may have a PRC (such as acetaldehyde) concentration of, for example, about 0.1 to 90% by weight (e.g., about 0.2 to 70% by weight), preferably about 0.3 to 60% by weight (e.g., about 0.4 to 50% by weight), more preferably about 0.5 to 40% by weight (e.g., about 1 to 20% by weight), and particularly about 2 to 10% by weight (e.g., about 3 to 7% by weight); or may have a PRC concentration of about 0.1 to 10% by weight, preferably about 0.5 to 7% by weight, and more preferably about 1 to 5% by weight; or may have a PRC concentration of about 3 to 10% by weight (e.g., about 5 to 8% by weight). The side-cut stream (5B) may have a methyl iodide concentration of, for example, about 1 to 99% by weight (e.g., about 5 to 97% by weight), preferably about 10 to 95% by weight (e.g., about 20 to 95% by weight), and more preferably about 30 to 95% by weight; or may have a methyl iodide concentration of about 50 to 99% by weight (e.g., about 65 to 98% by weight), preferably about 75 to 98% by weight (e.g., about 85 to 97% by weight), and more preferably about 90 to 97% by weight; may have a methyl iodide concentration of about 75 to 95% by weight (e.g., about 80 to 93% by weight). The side-cut stream (5B) may have a methyl acetate concentration of, for example, about 0.1 to 20% by weight (e.g., about 0.5 to 10% by weight) and preferably about 0.7 to 7% by weight (e.g., about 0.7 to 5% by weight), may have a methyl acetate concentration of about 0.5 to 5% by weight (e.g., about 0.5 to 3% by weight), or may have a methyl acetate concentration of about 1 to 5% by weight (e.g., about 2.5 to 5% by weight). The side-cut stream (5B) may have an acetic acid concentration of, for example, about 0 to 5% by weight (e.g., about 0.01 to 3% by weight) and preferably about 0.1 to 2% by weight, or may have an acetic acid concentration substantially not more than detection limit. The side-cut stream (5B) may have a water concentration of, for example, about 0.1 to 20% by weight (e.g., about 0.3 to 10% by weight), preferably about 0.5 to 5% by weight, and more preferably about 0.8 to 3% by weight (e.g., about 1 to 2% by weight). The side-cut stream (5B) may have a dimethyl ether concentration of, for example, about 0 to 3% by weight (e.g., about 0.0001 to 2% by weight) and preferably about 0.001 to 1.7% by weight (e.g., about 0.01 to 1.5% by weight), or a dimethyl ether concentration of about 0.005 to 1% by weight (e.g., about 0.01 to 0.5% by weight) or about 0.1 to 1% by weight. The side-cut stream (5B) may have a methanol concentration of, for example, about 0 to 3% by weight (e.g., about 0.001 to 2% by weight) and preferably about 0.01 to 1.5% by weight (e.g., about 0.05 to 1% by weight). The reduction of the number of distillation stages (or plates) of the second distillation column (5) (for example, the reduction the actual number of stages (or plates) from 100 to not more than 15% (or to about 10 to 15)) may tend to slightly increase the PRC (representatively acetaldehyde) concentration and the methyl acetate concentration in the side-cut stream (5B) (a mixture of an aqueous phase and an organic phase when the stream is separated into these phases; a mixture in the line 63, a mixture of a stream in the line 61 and a stream in the line 62).

In a case where the side-cut stream (5B) is liquid-liquid separated (or forms an organic phase and an aqueous phase), the organic phase (lines 64, 68) may have a PRC concentration of, for example, about 0.1 to 90% by weight (e.g., about 0.2 to 70% by weight) and preferably about 0.3 to 60% by weight (e.g., 0.4 to 50% by weight), or may have a PRC concentration of about 0.1 to 20% by weight (e.g., about 0.5 to 20% by weight) and preferably about 1 to 10% by weight (e.g., about 2 to 5% by weight), or may have a PRC concentration of about 3 to 10% by weight (e.g., about 5 to 8.5% by weight). The organic phase may have a methyl iodide concentration of, for example, about 50 to 99% by weight (e.g., about 60 to 98% by weight) and preferably about 70 to 97% by weight (e.g., about 80 to 95% by weight), or may have a methyl iodide concentration of about 85 to 98% by weight (e.g., about 90 to 97% by weight), or may have a methyl iodide concentration of about 85 to 93% by weight. The organic phase may have a methyl acetate concentration of, for example, about 0.1 to 20% by weight (e.g., about 0.5 to 10% by weight) and preferably about 0.7 to 7% by weight (e.g., about 1 to 5% by weight), or may have a methyl acetate concentration of about 2 to 4.54% by weight (e.g., about 3 to 4% by weight), or may have a methyl acetate concentration of about 0.3 to 7% by weight (e.g., about 0.5 to 5% by weight). The organic phase may have an acetic acid concentration of, for example, about 0 to 5% by weight (e.g., about 0.001 to 3% by weight), preferably about 0.01 to 2% by weight, and about 0.1 to 0.5% by weight, or may have an acetic acid concentration substantially not more than detection limit. The organic phase may have a water concentration of about 0 to 5% by weight (e.g., about 0.01 to 3% by weight) and preferably about 0.05 to 1% by weight (e.g., about 0.1 to 0.3% by weight). The organic phase may have a dimethyl ether concentration of, for example, about 0 to 2.5% by weight (e.g., about 0 to 5000 ppm), preferably about 1 ppm to 2% by weight (e.g., about 1 to 3000 ppm), more preferably about 10 ppm to 1.5% by weight (e.g., about 10 to 2500 ppm), and more preferably about 100 ppm to 1% by weight (e.g., about 100 to 2000 ppm). The organic phase may have a methanol concentration of, for example, about 0 to 3% by weight (e.g., about 0.001 to 2% by weight) and preferably about 0 to 1.5% by weight (e.g., about 0.05 to 0.5% by weight), or may have a methanol concentration substantially not more than detection limit. The reduction of the number of distillation stages (or plates) of the second distillation column (5) (for example, the reduction the actual number of stages (or plates) from 100 to not more than 15% (or to about 10 to 15)) may tend to slightly increase the PRC (representatively acetaldehyde) concentration and the methyl acetate concentration in the organic phase (the lines 64, 68) liquid-liquid separated from the side-cut stream (5B).

In a case where the side-cut stream (5B) is liquid-liquid separated (or forms an organic phase and an aqueous phase), the aqueous phase (lines 66, 69) may have a PRC concentration of about 1 to 50% by weight (e.g., about 5 to 40% by weight) and preferably about 10 to 30% by weight (e.g., about 15 to 25% by weight). The aqueous phase may have a methyl iodide concentration of, for example, about 0.01 to 10% by weight (e.g., about 0.1 to 5% by weight) and preferably about 0.5 to 4% by weight (e.g., about 0.8 to 3% by weight), or may have a methyl iodide concentration of about 1 to 2% by weight. The aqueous phase may have a methyl acetate concentration of, for example, about 0.1 to 10% by weight (e.g., about 0.2 to 5% by weight) and preferably about 0.3 to 2% by weight (e.g., about 0.5 to 1% by weight), or may have a methyl acetate concentration of about 0.1 to 1.5% by weight, or may have a methyl acetate concentration of about 0.5 to 3% by weight (e.g., about 1 to 2% by weight). The aqueous phase may have an acetic acid concentration of, for example, about 0 to 5% by weight (e.g., about 0.001 to 3% by weight) and preferably about 0.01 to 2% by weight, or may have an acetic acid concentration substantially not more than detection limit (0% by weight). The aqueous phase may have a dimethyl ether concentration of, for example, about 0 to 1.5% by weight (e.g., about 1 ppm to 1.2% by weight) and preferably about 0.001 to 1% by weight (e.g., about 0.01 to 1% by weight). The aqueous phase may have a methanol concentration of, for example, about 0.1 to 10% by weight (e.g., about 0.5 to 8% by weight) and preferably about 1 to 6% by weight (e.g., about 1.5 to 5% by weight). The aqueous phase usually contains these components, inevitable contaminants (including impurities or by-product), and water as the remainder. The aqueous phase may have a water concentration of, for example, about 50 to 95% by weight (e.g., about 60 to 93% by weight) and preferably about 70 to 90% by weight (e.g., about 75 to 85% by weight), or may have a water concentration of about 65 to 85% by weight (e.g., about 70 to 85% by weight). The reduction of the number of distillation stages (or plates) of the second distillation column (5) (for example, the reduction the actual number of stages (or plates) from 100 to not more than 15% (or to about 10 to 15)) may tend to slightly increase the methyl acetate concentration in the aqueous phase (the lines 66, 69) liquid-liquid separated from the side-cut stream (5B).

The PRC concentration in the extraction mixture or side-cut stream (5B) (the line 63) [for example, the acetaldehyde concentration in the aqueous phase (aqueous extract) (the lines 66, 69) formed in liquid-liquid separation] has a great influence on the ratio of methyl iodide relative to acetaldehyde (MeI/AD ratio), that is, the amount of methyl iodide to be discharged together with acetaldehyde to the outside of the system. The amount of methyl iodide to be discharged to the outside of the system is increased at either excessively low or high acetaldehyde concentration. In order to reduce the amount of methyl iodide to be discharged (or make the MeI/AD ratio smaller), the PRC concentration in the extraction mixture or side-cut stream (5B) (the line 63) (for example, the acetaldehyde concentration in the aqueous phase (aqueous extract)) may be about 0.1 to 45% by weight (e.g., about 0.5 to 30% by weight), preferably about 1 to 25% by weight (e.g., about 1.5 to 15% by weight), and more preferably about 2 to 10% by weight. The effective PRC concentration in the extraction mixture or side-cut stream (5B) (the line 63) (in particular, the acetaldehyde concentration in the aqueous phase (aqueous extract) (the lines 66, 69)) may be about 5 to 45% by weight, preferably about 10 to 40% by weight, and more preferably about 15 to 35% by weight (e.g., about 20 to 30% by weight) or may also be 10 to 25% by weight (e.g., about 12 to 25% by weight).

The aqueous phase (the lines 66, 69), which is a phase liquid-liquid separated from the side-cut stream (5B) contains enriched PRC's (e.g., acetaldehyde) and has a PRC (e.g., acetaldehyde) concentration higher than a methyl iodide concentration. The aqueous phase may have a ratio (AD/MeI) of acetaldehyde (AD) relative to methyl iodide (MeI) of, for example, about 3/1 to 50/1 (e.g., about 4/1 to 40/1) and preferably about 5/1 to 30/1 (e.g., about 7/1 to 20/1), or may be about 8/1 to 15/1 (e.g., about 10/1 to 15/1).

The side-cut stream (5B) (the line 63) may have a temperature at an atmospheric pressure of, for example, about 15 to 110° C. (e.g., about 20 to 90° C.) and preferably about 25 to 80° C. (e.g., about 30 to 70° C.).

The lower stream (5C) (a line 52) usually contains methyl iodide as a main component and is rich in methyl iodide. In a case where the first overhead stream (3A) to be fed to the distillation column (5) is a homogeneous liquid or a mixture of an aqueous phase and an organic phase, the lower stream (5C) (the line 52) may have a PRC (representatively, acetaldehyde) concentration of, for example, about 0 to 1% by weight (e.g., about 1 to 5000 ppm), preferably about 0 to 2500 ppm (e.g., about 10 to 1000 ppm), and more preferably about 50 to 500 ppm, or may have a PRC concentration of about 30 to 2500 ppm (e.g., about 100 to 2000 ppm), or may have a PRC concentration substantially not more than detection limit. The lower stream (5C) may have a methyl iodide concentration of, for example, about 10 to 85% by weight (e.g., about 25 to 80% by weight) and preferably about 40 to 75% by weight (e.g., about 50 to 70% by weight); may have a methyl iodide concentration of about 50 to 99% by weight (e.g., about 60 to 95% by weight) and preferably about 70 to 90% by weight (e.g., about 75 to 88% by weight), or may have a methyl iodide concentration of about 1 to 75% by weight (e.g., about 5 to 65% by weight). The lower stream (5C) may have a methyl acetate concentration of, for example, about 0 to 30% by weight (e.g., about 0.1 to 25% by weight) and preferably about 1 to 20% by weight (e.g., about 5 to 20% by weight), or may have a methyl acetate concentration of about 7 to 17% by weight (e.g., about 10 to 15% by weight); or may have a methyl acetate concentration of about 0 to 40% by weight (e.g., about 1 to 30% by weight) and preferably about 3 to 25% by weight (e.g., about 5 to 20% by weight), or may have a methyl acetate concentration of about 7 to 18% by weight (e.g., about 10 to 17% by weight), or may have a methyl acetate concentration of about 5 to 15% by weight. The lower stream (5C) may have an acetic acid concentration of, for example, about 0 to 12% by weight (e.g., about 0.1 to 10% by weight) and preferably about 0.5 to 8% by weight (e.g., about 1 to 7% by weight); or may have an acetic acid concentration of about 1 to 5% by weight (e.g., about 1 to 3% by weight), or may have an acetic acid concentration of about 5 to 30% by weight (e.g., about 7 to 25% by weight). The lower stream (5C) may have a water concentration of, for example, about not less than 1% by weight (e.g., about 5 to 89% by weight), preferably not less than 10% by weight (e.g., about 15 to 87% by weight), and more preferably not less than 20% by weight (e.g., about 30 to 85% by weight); or may have a water concentration of about 5 to 52% by weight (e.g., about 10 to 42% by weight) and preferably about 15 to 37% by weight (e.g., about 17 to 32% by weight); or may have a water concentration of about 0 to 10% by weight (e.g., about 0.001 to 5% by weight), preferably about 0.01 to 3% by weight (e.g., about 0.1 to 2% by weight), and more preferably about 0.2 to 1% by weight or more (e.g., about 0.3 to 0.8% by weight), or may have a water concentration of about 5 to 65% by weight (e.g., about 15 to 60% by weight). The lower stream (5C) may have a dimethyl ether concentration of, for example, about 0 to 2000 ppm (e.g., about 1 to 1500 ppm) and preferably about 10 to 1000 ppm (e.g., about 50 to 500 ppm); or may have a dimethyl ether concentration of about 0.01 to 1000 ppm and preferably about 0.1 to 500 ppm (e.g., about 1 to 100 ppm), or may have a dimethyl ether concentration substantially not more than detection limit. The lower stream (5C) may have a methanol concentration of, for example, about 0 to 2% by weight (e.g., about 0.0001 to 1% by weight) and preferably about 0.001 to 0.5% by weight (e.g., about 0.01 to 0.3% by weight) or may have a methanol concentration of about 0.1 to 1.5% by weight (e.g., about 0.2 to 1% by weight). In a case where the water concentration in the first overhead stream (3A) to be fed to the second distillation column (5) (or the ratio of the aqueous phase 43b relative to the organic phase 44) is increased, the lower stream (5C) (the line 52) may show tendencies to decrease the methyl iodide concentration and the methyl acetate concentration and to increase the water content, and to slightly increase the methanol concentration.

In a case where the first overhead stream (3A) to be fed to the distillation column (5) is a mixture of an aqueous phase and an organic phase, the lower stream (5C) (the line 52) may have a PRC (representatively, acetaldehyde) concentration of, for example, about 0 to 1% by weight (e.g., about 1 to 5000 ppm), preferably about 0 to 2500 ppm (e.g., about 10 to 1000 ppm), and more preferably about 50 to 500 ppm; or may have a PRC concentration of about 50 to 5000 ppm (e.g., about 100 to 3000 ppm) and preferably about 150 to 2000 ppm (e.g., about 170 to 1500 ppm); or may have a PRC concentration substantially not more than detection limit. The lower stream (5C) may have a methyl iodide concentration of, for example, about 1 to 80% by weight (e.g., about 3 to 70% by weight), preferably about 5 to 60% by weight (e.g., about 7 to 50% by weight), and more preferably about 10 to 40% by weight, or may have a methyl iodide concentration of about 7 to 60% by weight (e.g., about 10 to 55% by weight). The lower stream (5C) may have a methyl acetate concentration of, for example, about 0 to 40% by weight (e.g., about 1 to 30% by weight) and preferably about 3 to 25% by weight (e.g., about 5 to 20% by weight); or may have a methyl acetate concentration of about 7 to 18% by weight (e.g., about 8 to 17% by weight); or may have a methyl acetate concentration of about 5 to 15% by weight (e.g., about 7 to 13% by weight). The lower stream (5C) may have an acetic acid concentration of, for example, about 0 to 40% by weight (e.g., about 1 to 30% by weight) and preferably about 2 to 25% by weight (e.g., about 3 to 23% by weight), or may have an acetic acid concentration of about 5 to 30% by weight (e.g., about 8 to 25% by weight). The lower stream (5C) may have a water concentration of, for example, about 1 to 95% by weight (e.g., about 2 to 90% by weight), preferably about 5 to 85% by weight (e.g., about 7 to 80% by weight), more preferably about 10 to 75% by weight (e.g., about 20 to 70% by weight), and more preferably about 30 to 65% by weight, or may have a water concentration of about 20 to 60% by weight. The lower stream (5C) may have a dimethyl ether concentration of, for example, about 0 to 2000 ppm (e.g., about 0.01 to 1000 ppm) and preferably about 0.1 to 500 ppm (e.g., about 1 to 100 ppm), or may have a dimethyl ether concentration substantially not more than detection limit. The lower stream (5C) may have a methanol concentration of, for example, about 0 to 2% by weight (e.g., about 0.0001 to 1% by weight) and preferably about 0.001 to 0.5% by weight (e.g., about 0.01 to 0.3% by weight), or may have a methanol concentration of about 0.1 to 2% by weight (e.g., about 0.2 to 1.5% by weight) and preferably about 0.3 to 1% by weight.

In a case where the first overhead stream (3A) to be fed to the distillation column (5) is an organic phase formed in liquid-liquid separation, the lower stream (5C) may have a PRC (representatively, acetaldehyde) concentration of, for example, about 0 to 1% by weight (e.g., about 1 to 5000 ppm) and preferably about 0 to 2500 ppm (e.g., about 10 to 1000 ppm), or may have a PRC concentration substantially not more than detection limit. The lower stream (5C) may have a methyl iodide concentration of, for example, about 10 to 95% by weight (e.g., about 30 to 93% by weight) and preferably about 50 to 90% by weight (e.g., about 70 to 90% by weight); for example, or may have a methyl iodide concentration of not less than 10% by weight (e.g., about 15 to 90% by weight), preferably not less than 20% by weight (e.g., about 25 to 90% by weight), more preferably not less than 30% by weight (e.g., about 30 to 80% by weight), and particularly about 40 to 70% by weight (e.g., about 50 to 65% by weight). The lower stream (5C) may have a methyl acetate concentration of, for example, about 1 to 30% by weight (e.g., about 3 to 25% by weight) and preferably about 5 to 20% by weight (e.g., about 7 to 16% by weight). The lower stream (5C) may have an acetic acid concentration of, for example, about 0 to 10% by weight (e.g., about 0.1 to 7% by weight) and preferably about 0.3 to 5% by weight (e.g., about 0.5 to 3% by weight). The lower stream (5C) may have a water concentration of about 0 to 52% by weight (e.g., about 0.01 to 42% by weight), preferably about 0.1 to 32% by weight (e.g., about 0.2 to 22% by weight), and more preferably about 0.5 to 11% by weight (e.g., about 1 to 6% by weight); or may have a water concentration of about 0 to 6% by weight (e.g., about 0.1 to 4% by weight) and preferably about 0.3 to 3% by weight (e.g., about 0.5 to 2% by weight). The lower stream (5C) may have a dimethyl ether concentration of, for example, about 0 to 2000 ppm (e.g., about 1 to 1500 ppm) and preferably about 10 to 1000 ppm (e.g., about 50 to 500 ppm); or may have a dimethyl ether concentration of about 5 to 500 ppm (e.g., about 10 to 100 ppm); or may have a dimethyl ether concentration substantially not more than detection limit. The lower stream (5C) may have a methanol concentration of, for example, about 0 to 1% by weight (e.g., about 0.001 to 0.8% by weight) and preferably about 0.005 to 0.5% by weight (e.g., about 0.01 to 0.5% by weight).

In a case where the first overhead stream (3A) to be fed to the distillation column (5) is an aqueous phase formed in liquid-liquid separation, the lower stream (5C) may have a PRC (representatively, acetaldehyde) concentration of, for example, about 0 to 1% by weight (e.g., about 1 to 5000 ppm) and preferably about 0 to 2500 ppm (e.g., about 10 to 1000 ppm), or may have a PRC concentration substantially not more than detection limit. The lower stream (5C) may have a methyl iodide concentration of, for example, about 0.1 to 30% by weight (e.g., about 0.5 to 25% by weight) and preferably about 1 to 20% by weight (e.g., about 3 to 15% by weight); or may have a methyl iodide concentration of not less than 1.5% by weight (e.g., about 2 to 50% by weight), preferably not less than 2% by weight (e.g., about 3 to 40% by weight), and more preferably not less than 4% by weight (e.g., about 5 to 30% by weight). The lower stream (5C) may have a methyl acetate concentration of, for example, about 1 to 30% by weight (e.g., about 3 to 25% by weight) and preferably about 5 to 20% by weight (e.g., about 7 to 15% by weight). The lower stream (5C) may have an acetic acid concentration of, for example, about 5 to 60% by weight (e.g., about 10 to 50% by weight) and preferably about 20 to 40% by weight (e.g., about 25 to 35% by weight). The lower stream (5C) may have a water concentration of, for example, about 10 to 92% by weight (e.g., about 25 to 82% by weight) and preferably about 30 to 77% by weight (e.g., about 40 to 72% by weight). The lower stream (5C) may have a dimethyl ether concentration of, for example, about 0 to 2000 ppm (e.g., about 0.1 to 1500 ppm) and preferably about 1 to 1000 ppm (e.g., about 5 to 500 ppm); or may have a dimethyl ether concentration of about 1 to 500 ppm (e.g., about 5 to 100 ppm); or may have a dimethyl ether concentration substantially not more than detection limit. The lower stream (5C) may have a methanol concentration of, for example, about 0 to 5% by weight (e.g., about 0.001 to 3% by weight) preferably about 0.1 to 2.5% by weight (e.g., about 0.5 to 2% by weight).

The lower stream (5C) may have a temperature at an atmospheric pressure of, for example, about 30 to 160° C. (e.g., about 35 to 120° C.) and preferably about 40 to 100° C. (e.g., about 40 to 80° C.).

The lower stream (5C) has a PRC (such as acetaldehyde) concentration significantly lower than that of the first overhead stream (3A). For example, the lower stream (5C) may have a PRC concentration of about 1 ppm to 0.3% by weight (e.g., about 1 to 800 ppm), preferably about 10 ppm to 0.2% by weight (e.g., about 20 to 1000 ppm), and more preferably about 30 to 500 ppm, or may have a PRC concentration substantially not more than detection limit (0% by weight). Thus the lower stream (5C) may be recycled to the reaction system via the line 52. If necessary, via the line 52 the lower stream (5C) may be subjected to additional distillation and then optional water extraction to remove and separate PRC's (e.g., acetaldehyde).

According to the present invention, the first overhead stream (3A) is distilled in the second distillation step (5) to form the second overhead stream (5A), the side-cut stream (5B), and the lower stream or bottom stream (5C). The distillation column of the second distillation step (5) may function as an aldehyde-removing column. Thus the first overhead stream (3A) contains at least a PRC (e.g., acetaldehyde) and methyl iodide and has a composition corresponding to the composition of the mixed composition. The first overhead stream or mixed composition (3A) may further contain methyl acetate. As described above, the first overhead stream or mixed composition (3A) may further contain at least one selected from acetic acid, methanol, water, dimethyl ether, an acetaldehyde derivative (e.g., an aldehyde, a ketone, an alkyl iodide, a higher boiling point alkanecarboxylic acid, and an alkane), a dialkyl ether, or other compounds.

The distillation column of the second distillation step (5) is provided with at least one receiver (e.g., a chimney tray). The distillation column may be provided with a plurality of receivers (chimney trays). For a distillation column having a plurality of receivers (chimney trays), the extractant is added to a concentration zone that is formed above the uppermost chimney tray.

(6) Liquid-Liquid Separation Step

In the embodiment shown in FIG. 1, the second overhead stream (5A) is cooled and condensed in the condenser C3 on the withdrawing line 53 and is then biphasically separated in the separation unit (decanter) 6a to form an organic phase (a lower phase, a raffinate) and an aqueous phase (an upper phase, an extract). The organic phase is refluxed or recycled to the distillation column (for example, the top of the column) of the second distillation step (5) via the reflux line 61. The aqueous phase from the decanter 6a is fed to the hold tank 6b via the line 62. The extraction mixture (5B) as the side-cut stream is also fed to the hold tank 6b via the line 63. The liquid in the hold tank 6b s biphasically separated. The hold tank 6b also functions as a buffer tank or a decanter.

The organic phase (the raffinate) from the hold tank 6b is recycled to the distillation column of the second distillation step (5) via the line 64 and a recycle line 65 at a position lower than a position withdrawing the side-cut stream (5B). The side-cut stream and extraction mixture (5B) have a relatively high temperature, and a portion of the aqueous phase (the extract) from the hold tank 6b is cooled in a cooling unit (cooler) C4 on the line 66 and is biphasically separated in the decanter 6c. The residual portion of the aqueous phase (the extract) from the hold tank 6b is recycled to the distillation column of the second distillation step (5) via the line 67 at a position lower than a position withdrawing the side-cut stream (5B). As shown by a dotted line, a portion of the aqueous phase (extract) in the line 66 may be recycled as an extractant.

In the decanter 6c, a small amount of methyl iodide can be separated by biphasic separation (or formation of an organic phase and an aqueous phase). The organic phase (a heavy phase rich in methyl iodide or a lower phase) formed in the decanter 6c is recycled to the distillation column of the second distillation step (5) via the line 68. The aqueous phase (a light phase rich in acetaldehyde or an upper phase) formed in the decanter 6c is fed to the third distillation step (distillation column) (7) via the line 69 for further separating PRC's and methyl iodide.

Each of the condensate (the aqueous phase, the organic phase, or a mixture thereof) cooled in the condenser C3 and the liquid stream (and the aqueous phase and the organic phase) cooled in the cooling unit C4 may have a temperature of, for example, about 0 to 60° C. (e.g., about 1 to 50° C.), preferably about 3 to 30° C. (e.g., about 3 to 20° C.), and more preferably about 5 to 15° C.

In practical cases, at least the extraction mixture (5B) is biphasically separated. The extraction mixture (5B) and the overhead stream (5A) may biphasically be separated independently or in combination. Specifically, as described above, each of the extraction mixture (5B) and the overhead stream (5A) may be liquid-liquid separated; or, without liquid-liquid separation of the overhead stream (5A) in the decanter 6a, the overhead stream (5A) may be mixed or merged with the extraction mixture (5B) and the resulting mixture may be liquid-liquid separated.

The extract (aqueous phase) and/or the raffinate (organic phase) formed in liquid-liquid separation may be recycled in various manners (via various routes) to the second distillation step (5). In this embodiment, as described above, a portion of the aqueous phase formed in the hold tank 6b and the organic phases (the organic phase formed in the hold tank 6b and the organic phase formed in the decanter 6c) are mixed together via the line 67 and the lines 64, 68, respectively, to recycle the resulting mixture to the second distillation step (5).

To the second distillation step (5) may be recycled a portion of the raffinate (or organic phase), practically at least a portion of the raffinate (or organic phase), for example, the whole of the raffinate (or organic phase).

To the third distillation step (distillation column) (7), the extract (or aqueous phase) formed in the second liquid-liquid separation step (6) is fed, and usually at least a portion or the whole of the extract (or aqueous phase) is fed. If necessary, a portion of the raffinate (or organic phase) may also be fed to the third distillation step (distillation column) (7).

Recycling at least the extract (or aqueous phase) to a plate being in a lower position of the distillation column (5) than a withdrawing port for withdrawing the side-cut stream (5B) increases the concentrations of acetaldehyde and water in an upper position than the feed plate in the distillation column (5) to prevent the formation of an azeotropic composition containing combination of a plurality of components such as methyl iodide, methyl acetate, acetaldehyde, and water, and in some cases to reduce the concentration of acetic acid by increasing the water concentration. Thus, the methyl acetate concentration can be reduced in a space upper than the feed plate of the distillation column (5). Further, acetic acid present in a space upper than the feed plate of the distillation column (5) may be converted into methyl iodide or methyl acetate to decrease in concentration of acetic acid. For example, the concentration of methyl acetate or acetic acid in a space upper than the feed plate (recycle plate) of the distillation column (5) can be reduced: by feeding the aqueous phase and the organic phase to the distillation column (5) via the feed lines 43b and 44; by recycling the organic phase via the lines 64, 68 and the aqueous phase via the line 67 to the distillation column (5); and/or by feeding the aqueous phase to the distillation column (5) via the feed line 43b. Moreover, recycle of a stream (including an aqueous phase, an organic phase, or others) to the second distillation step (5) increases the concentration of the components of the recycling stream in the distillation column to prevent an increase in the concentration of the amphipathic compound such as methyl acetate, irrespective of the position of the withdrawing port for withdrawing the side-cut stream (5B). Thus, the concentration of methyl acetate or acetic acid in the aqueous phase [for example, the side-cut stream (5B), the aqueous phase in the tank 6b, and further, the aqueous phase via the line 67] can be reduced to decrease the amount of methyl iodide dissolved in the aqueous phase. The recycling amount of the aqueous phase may suitably be selected considering the stability of the process. Too large a recycling amount of the aqueous phase causes outflow of a large amount of water from the bottom stream (5C) (the line 52) of the second distillation column (5) to undesirably increase the concentration of water in the reaction system or the process. In a case where a large amount of acetic acid is incorporated with the side-cut stream (5B) by addition and distillation and recycling of acetic acid (miscible solvent) as the amphipathic component (mentioned hereinafter), the amount of methyl iodide, as well as methyl acetate, dissolved in the aqueous phase is increased to induce a loss of methyl iodide.

It is not necessary to cool and condense the second overhead stream (5A) for liquid-liquid separating the condensate in the separation unit 6a. The whole of the second overhead stream (5A) may be refluxed in the distillation column of the second distillation step (5).

According to the present invention, the extraction mixture (5B) may be fed to the third distillation step (distillation column) (7) without being subjected to the liquid-liquid separation step (6) (or without condensation and/or liquid-liquid separation).

The extraction mixture (5B) is usually separable into an upper phase (aqueous phase) and a lower phase (organic phase). Thus in a case where the extraction mixture is biphasically separable in the distillation column of the distillation step (5), the extraction mixture (5B) may be retained in a tray (or a decanter in the distillation system) for biphasic separation, or an aqueous phase formed in the column may selectively be withdrawn by side-cut. In a preferred embodiment, the whole amount of the falling liquid or the extraction mixture (5B) may be withdrawn from the distillation column of the distillation step (5) by side-cut, and if necessary after being cooled, the withdrawn mixture may biphasically be separated in a decanter which is disposed outside of the distillation system. Further, the extraction mixture (5B) and the overhead stream (5A) may biphasically be separated independently or in combination.

The total retention time of the extraction mixture in the extractive distillation zone formed in the distillation column and the decanter disposed in the outside of the distillation system is sufficient for biphasic separation of the extraction mixture. The total retention time may be, for example, not less than 10 seconds (e.g., about 30 seconds to 120 minutes) and preferably about 1 to 100 minutes (e.g., about 5 to 60 minutes), or may be about 10 to 120 minutes (e.g., about 15 to 60 minutes).

In the liquid-liquid separation step (6), at least the side-cut stream or extraction mixture (53) among the second overhead stream (5A) and the side-cut stream or extraction mixture (5B) may biphasically be separated to further separate PRC's and methyl iodide from each other.

The liquid-liquid separation step (6) may comprise one or two liquid-liquid separation steps (or a hold tank and/or a decanter) without using a plurality of units (the separation unit 6a, the hold tank 6b, and the decanter 6c). At least a portion of the aqueous phase (acetaldehyde-enriched aqueous phase) may be separated or removed to the outside of the process; may be used as an extractant for the distillation step (5); or may be recycled to the reaction step (reactor) (1). At least a portion of the organic phase (an organic phase containing methyl iodide) may be recycled to the distillation step (5) directly or indirectly. For example, the organic phase rich in methyl iodide can be recycled to an appropriate position of the distillation column of the second distillation step (5); may be recycled to an upper position than the withdrawing port for the side-cut stream (5B); or may preferably be recycled to a lower position than the withdrawing port for the side-cut stream (5B) to form a concentration zone in the second distillation step (5).

As described above, the side-cut stream (5B) is practically obtained from the concentration zone in order to extract PRC's efficiently. In such a case, the extraction mixture (such as the organic phase) may be recycled to the concentration zone of the distillation column (5) or may be recycled to a plate having the same height level as that of the feed port (or feed plate) for the first overhead stream or mixed composition (3A) or may be recycled to a plate lower than the feed port.

[Miscible Solvent]

In order to efficiently separate methyl iodide and PRC's (e.g., acetaldehyde) from each other in the presence of methyl acetate, a miscible solvent that is miscible with an organic phase may be fed to a stream (an organic phase and/or an aqueous phase) which is recycled to the second distillation step (5). The miscible solvent may include a solvent having a high affinity with either an amphipathic compound (such as methyl acetate) or PRC's; a solvent capable of inhibiting formation of an azeotropic composition of an amphipathic compound (such as methyl acetate) and other compounds (in particular, water, PRC's such as acetaldehyde); and a solvent that lowers a volatility (vapor pressure) of an amphipathic compound (such as methyl acetate); or other solvents. The miscible solvent usually changes an azeotropic composition (or gas composition) of PRC's and methyl iodide in the presence of methyl acetate, or prevents the formation of an azeotropic composition and causes a concentration distribution of methyl acetate in the height direction of the distillation column; and/or lowers the volatility (vapor pressure) of methyl acetate. Thus addition of the miscible solvent reduces the concentration of methyl acetate in the aqueous phase and prevents methyl iodide being mixed into the aqueous phase.

The miscible solvent may be an internal miscible solvent present in the system [for example, a solvent present in the acetic acid production process or a solvent produced in the process, or a process stream (e.g., an aqueous solvent such as an aqueous extract 67)] or may be an external miscible solvent from the outside of the system (for example, at least one selected from water, acetic acid, and other compounds). The miscible solvent may have a boiling point higher than those of methyl iodide and PRC's (e.g., acetaldehyde). The process stream may be a process stream (e.g., a crude acetic acid stream, an overhead stream, a bottom stream, and a recycle stream) capable of lowering the volatility (vapor pressure) of methyl acetate. The miscible solvent may be an amphipathic solvent. The miscible solvent usually contains at least one member selected from water, acetic acid, methyl iodide, and methanol. The miscible solvent which is fed from outside may be water or other solvents, and is usually an organic miscible solvent, for example, a miscible solvent containing acetic acid (such as acetic acid or crude acetic acid). A preferred miscible solvent may be an aqueous phase separated from the second overhead stream (5A) and/or the side-cut stream (5B) [for example, an aqueous phase produced in the second liquid-liquid separation step (6)] or may be a process stream containing acetic acid (e.g., a crude acetic acid stream).

In the process shown in FIG. 1, to the distillation column of the second distillation step (5) is fed the miscible solvent via a feed line 70 and/or the aqueous phase (or extract) via the line 67, and the distillation in the presence of the miscible solvent separates methyl iodide and PRC's (e.g., acetaldehyde) in the presence (coexistence) of an amphipathic compound (such as methyl acetate).

The miscible solvent may directly be fed to the distillation column of the second distillation step (5) via the feed line 70 or may indirectly fed to the distillation column of the second distillation step (5) via a recycle line 65 or other lines. The miscible solvent is usually fed to a lower position than the receiver (such as a chimney tray) in height in order to prevent the condensation of methyl acetate in a space between the lower feed port and the feed plate of the first overhead stream (3A) (in the process shown in the drawing, the condensate from the liquid-liquid separation step (4)) in practical cases. The miscible solvent may be fed to an upper position than or over the receiver (such as a chimney tray) in height (for example, to the concentration zone or extraction zone). Incidentally, condensation of ethyl acetate in the space can be prevented by avoiding (or inhibiting) the formation of the azeotropic composition, by lowering the volatility (vapor pressure) of methyl acetate, or by other means, as described above.

Assuming that the total number of plates of the distillation column is 100, feeding the miscible solvent (such as acetic acid) to a plate lower than the recycle line 65 (for example, a plate that is positioned at 10 to 30 plates lower than a recycle plate to which a recycle stream is fed via the recycle line 65) can effectively prevent the miscible solvent (e.g., acetic acid) from mixing with the extraction mixture (5B) of the line 63. Thus, it is possible to reduce the amount of methyl iodide dissolved in the aqueous phase separated in the liquid-liquid separation step (6). Assuming that the total number of plates of the distillation column is 100, the miscible solvent such as acetic acid may be fed to a plate that is lower than the side-cut plate (receiver) of the side-cut stream (5B), and is the 10th to the 50th (e.g., the 20th to the 40th) plate from the uppermost plate. For example, assuming that the height level of the distillation portion of the distillation column is "1", the miscible solvent may, for example, be fed at a height level of about 0.1/1 to 0.5/1 (e.g., about 0.15/1 to 0.45/1) and preferably about 0.2/1 to 0.4/1 (e.g., about 0.25/1 to 0.3/1) from the top of the column. For example, for a plate distillation column having the total actual number of stages (or plates) of 43, the miscible solvent may be fed between the uppermost plate of the column top and a plate that is positioned at 40 plates lower than the uppermost plate (the 40th plate) (preferably the 35th plate from the uppermost plate, more preferably the 25th plate from the uppermost plate, and particularly the 15th plate from the uppermost plate). For a plate distillation column having the total actual number of stages (or plates) of 10, the miscible solvent may be fed between the uppermost plate of the column top and a plate positioned at 10 plates lower than the uppermost plate (the 10th plate) (preferably the 7th plate from the uppermost plate, more preferably the 5th plate from the uppermost plate, and particularly the 3rd plate from the uppermost plate).

The miscible solvent may have the same temperature as the extractant has. The miscible solvent may be added to the distillation column as a heated solvent having the same temperature as the temperature of the extractant or as a vaporized form (or steam).

The amount to be added of the miscible solvent may be not more than 30% by weight, for example, about 0.01 to 20% by weight (e.g., about 0.1 to 15% by weight), and preferably about 0.5 to 10% by weight (e.g., about 1 to 5% by weight) relative to the amount of the liquid falling from the concentration zone (the amount of the liquid falling in the tray(s)) in the second distillation step (5). The total of the amount of the extraction mixture (5B) recycled to the second distillation step (5) [for example, the recycled amount of the aqueous phase, biphasically separated, in the extraction mixture (5B)] and/or the added amount of the miscible solvent may be not more than 30% by weight [e.g., about 0.01 to 20% by weight (e.g., about 0.1 to 15% by weight) and preferably about 0.5 to 10% by weight (e.g., about 1 to 5% by weight)] relative to the amount of the liquid falling from the concentration zone in the second distillation step (5), as the same as described above.

In a case where the miscible solvent (e.g., acetic acid) is distilled in the distillation column of the second distillation step (5) together with an organic phase from the liquid-liquid separation step (6) or other steps [for example, distillation of the organic phase formed in the hold tank 6b and the miscible solvent (e.g., acetic acid) from the line 70, or distillation of the organic phase and the miscible solvent (e.g., acetic acid) fed from a distillation plate lower than a position withdrawing the side-cut stream (5B)], the combination of a plurality of components such as methyl iodide, methyl acetate, acetaldehyde, and water may be avoided from forming an azeotrope (or an azeotropic composition) or the vapor pressure of methyl acetate may simply be lowered (or reduced) in the second distillation column (5). Even in such a case, the methyl acetate concentration in the process liquid (a condensate, an upper phase and/or a lower phase, in particular, an upper phase containing acetaldehyde) fed to the third distillation step (7) via the line 69 may be decreased to result in the reduction of the concentration of methyl iodide dissolved in the aqueous phase.

In the production process of acetic acid, although it is preferred to use water in the system as a balanced (or internal) water without supply of water from the outside of the system, recycling of the aqueous phase (for example, the aqueous phase via the line 67) to the distillation column (5) slightly increases the water concentration in the bottom stream (5C) (the line 52) of the distillation column (5), thereby changing the water balance in the system. In contrast, use of the organic miscible solvent such as acetic acid reduces the concentration of methyl acetate in the distillation column while maintaining the water balance in the system, thus reducing the amount of methyl iodide to be discharged. For example, the aqueous phase (for example, the aqueous phase in the system, such as in the line 67) is recycled to the distillation column (5) while the miscible solvent (e.g., acetic acid) is added to the distillation column (5), and the bottom stream (5C) (the line 52) from the distillation column (5) is recycled to the reaction system; such a process reduces the concentration of methyl acetate in the distillation column to the utmost limit to reduce the amount of methyl iodide to be discharged to the outside of the system, while preventing accumulation of water in the reaction system.

The addition of the miscible solvent (e.g., acetic acid) may induce an aldol condensation in the distillation column of the second distillation step (5) to produce higher boiling point substances from acetaldehyde, which is to be concentrated in the top of the column, and thus can decrease separation of acetaldehyde. However, acetic acid only exhibits an extremely weak acidity in a system having a high concentration of methyl iodide and a low concentration of water. In such a system, the aldol condensation under an acidic condition is minimized and hardly affects the concentration of acetaldehyde.

Thus, the introduction of the aqueous solvent (for example, the aqueous extract 67) produced in the process and/or the miscible solvent into the distillation column of the second distillation step (5) prevents an azeotrope formation of two or three components selected from methyl iodide, water, methyl acetate, and acetaldehyde or simply lowers the vapor pressure of methyl acetate to significantly decrease the concentration of methyl acetate in the aqueous phase.

Incidentally, in a case where an amount of acetic acid as the miscible solvent is too large, there is a possibility to increase a concentration of acetic acid in the side-cut stream (5B) and the extract 67 and to increase a concentration of methyl iodide in the aqueous phase. However, such a situation is avoidable by feeding an appropriate amount of acetic acid.

If necessary, the liquid (the condensate, the aqueous phase and/or the organic phase) formed in the liquid-liquid separation step (6) may temporarily be stored or retained in a buffer tank to reduce fluctuation of the flow rate of the process stream.

(7) Distillation Step

The aqueous phase (a light phase rich in acetaldehyde or an upper phase) from the liquid-liquid separation step (6) is separated into a third overhead stream (lower boiling point stream) (7A) rich in a permanganate reducing compound (in particular, acetaldehyde) and methyl iodide, and a liquid stream rich in the extractant (higher boiling point stream, lower stream or bottom stream) (7B) in the third distillation step (distillation column) (7). The third overhead stream (lower boiling point stream) (7A) is cooled and condensed in a condenser C5; a first portion of the condensate is returned to the distillation column (7) of the third distillation step via a reflux line 73 for reflux, and a second portion of the condensate is fed to a fourth distillation step (8) via a feed line 74.

The internal temperature of the distillation column of the third distillation step (7) depends on an internal pressure thereof. At the internal pressure of an atmospheric pressure, the distillation column may have a column top temperature of, for example, about 10 to 90° C. (e.g., about 15 to 80° C.) and preferably about 20 to 70° C. (e.g., about 20 to 60° C.), or may have a column bottom temperature of, for example, about 70 to 170° C. (e.g., about 80 to 160° C.) and preferably about 90 to 150° C. (e.g., about 95 to 140° C.). The distillation column may have a column top pressure of, for example, about 0.1 to 0.5 MPa, preferably about 0.2 to 0.4 MPa and more preferably about 0.25 to 0.35 MPa in terms of absolute pressure.

The distillation column may have a theoretical stage (or plate) of, for example, about 1 to 50 (e.g., about 2 to 40) and preferably about 3 to 30 (e.g., about 5 to 10). The reflux ratio of the distillation column may be, for example, about 1 to 1000 (e.g., about 2 to 500), preferably about 3 to 100 (e.g., about 4 to 50), and more preferably about 5 to 30.

The overhead stream (7A) or a condensate thereof (lines 72, 73, 74) is rich in acetaldehyde and has a lower methyl iodide concentration. The overhead stream (7A) or the condensate thereof also contains methyl acetate. The condensate of the overhead stream (7A) may have a PRC (representatively acetaldehyde) concentration of, for example, about 50 to 99.9% by weight (e.g., about 60 to 99% by weight), preferably about 70 to 98% by weight (e.g., about 75 to 97% by weight), and more preferably about 80 to 95% by weight (e.g., about 85 to 95% by weight). The condensate may have a methyl iodide concentration of, for example, about 0.1 to 20% by weight and preferably about 0.5 to 10% by weight (e.g., about 1 to 7% by weight), or may have a methyl iodide concentration of about 2 to 10% by weight (e.g., about 3 to 10% by weight). The condensate may have a methyl acetate concentration of, for example, about 0.1 to 20% by weight, preferably about 0.5 to 15% by weight (e.g., about 0.7 to 12% by weight), and more preferably about 1 to 10% by weight (e.g., about 1 to 5% by weight). The condensate of the overhead stream (7A) may have an acetic acid concentration of, for example, about 0 to 5% by weight, preferably about 0 to 3% by weight, and more preferably about 0 to 1% by weight. In some embodiments, the condensate of the overhead stream (7A) substantially contains no acetic acid (or has an acetic acid concentration not more than detection limit). The condensate of the overhead stream (7A) may have a water concentration of, for example, about 0 to 5% by weight (e.g., about 0 to 3% by weight), preferably 0 to 1% by weight (e.g., 0 to 0.1% by weight), or may have a water concentration not more than detection limit. The condensate may have a dimethyl ether concentration of, for example, about 1 ppm to 5% by weight (e.g., about 0.001 to 3% by weight), preferably about 0.01 to 2.5% by weight (e.g., about 0.1 to 2% by weight), and more preferably about 0.5 to 1.5% by weight. The condensate of the overhead stream (7A) may have a methanol concentration of, for example, about 0.1 to 40% by weight (e.g., about 1 to 30% by weight), preferably about 2 to 25% by weight (e.g., about 5 to 20% by weight), and more preferably about 7 to 18% by weight (e.g., about 10 to 15% by weight).

The overhead stream (7A) may have a temperature at an atmospheric pressure of, for example, about 15 to 110° C. (e.g., about 20 to 90° C.) and preferably about 25 to 80° C. (e.g., about 30 to 70° C.), or may have a temperature at an atmospheric pressure of about 20 to 55° C. The condensate (the lines 73, 74) of the overhead stream (7A) cooled in the condenser C5 may have a temperature of, for example, about 0 to 60° C. (e.g., about 5 to 45° C.) and preferably about 7 to 30° C. (e.g., about 10 to 30° C.).

The bottom liquid stream (7B) (a line 71) usually contains an extractant as a main component. The bottom liquid stream (78) may contain, in addition to the extractant, small amounts of components such as acetaldehyde, methyl iodide, acetic acid, methyl acetate, methanol, dimethyl ether (DME), and impurities present in the system. The liquid stream (7B) may have a PRC (representatively acetaldehyde) concentration (on the basis of weight) of, for example, not more than 0.1% by weight (e.g., about 1 ppb to 0.1% by weight), preferably not more than 500 ppm (e.g., about 10 ppb to 300 ppm), and more preferably not more than 100 ppm (e.g., about 0.1 ppm to 100 ppm), or may have a PRC concentration substantially not more than detection limit (0% by weight). The liquid stream (7B) may have a methyl iodide concentration of, for example, not more than 1% by weight (e.g., about 1 ppm to 0.8% by weight) and preferably not more than 0.5% by weight (e.g., about 10 ppm to 0.1% by weight), or may have a methyl iodide concentration substantially not more than detection limit (0% by weight). The liquid stream (7B) may have a methyl acetate concentration of about 1 ppm to 4% by weight (e.g., about 5 ppm to 2% by weight) and preferably about 0.001 to 1% by weight (e.g., about 0.005 to 0.7% by weight). The liquid stream (7B) may have an acetic acid concentration of, for example, not more than 10% by weight (e.g., about 1 ppm to 10% by weight) and preferably not more than 7% by weight (e.g., about 0.001 to 5% by weight), or may have an acetic acid concentration substantially not more than detection limit (0% by weight). The liquid stream (7B) may have a dimethyl ether concentration of, for example, about 0 to 1000 ppm (e.g., about 0 to 100 ppm) and preferably about 0 to 50 ppm (e.g., about 0 to 10 ppm), or may have a dimethyl ether concentration substantially not more than detection limit (0% by weight). The liquid stream (7B) may have a methanol concentration of, for example, about 0 to 5% by weight (e.g., about 1 ppm to 3% by weight), preferably about 10 ppm to 2% by weight (e.g., about 50 ppm to 1% by weight), and more preferably about 100 ppm to 0.5% by weight (e.g., about 200 to 2000 ppm), or may have a methanol concentration substantially not more than detection limit. The bottom liquid stream (7B) usually contains these components, inevitable contaminants (including impurities or by-products), and water as the remainder. The bottom liquid stream (7B) may have a water concentration of, for example, about 90 to 99.99% by weight (e.g., about 93 to 99.98% by weight) and preferably about 95 to 99.95% by weight (e.g., about 97 to 99.9% by weight). The bottom liquid stream (7B) may be recycled, as an extractant in the second distillation step (5), to the distillation step (5) via the bottom line 71.

The bottom liquid stream (73) may have a temperature at an atmospheric pressure of, for example, about 70 to 160° C. (e.g., about 80 to 120° C.) and preferably about 85 to 110° C. (e.g., about 90 to 110° C.), or may have a temperature at an atmospheric pressure of about 95 to 105° C.

Probably because acetic acid and methyl acetate are predominantly transferred to the bottom liquid stream (7B), the third overhead stream (7A) seems to have each of a ratio (MeI/AC ratio) of methyl iodide (MeI) relative to acetic acid (AC) and a ratio (MeI/MA ratio) of methyl iodide (MeI) relative to methyl acetate (MA) higher than the liquid fed from the line 69.

In the process shown in FIG. 1, the aqueous phase formed in the liquid-liquid separation step (6) is distilled. As described above, the side-cut stream (5B) may be distilled in the third distillation step (7) without passing through the liquid-liquid separation step (6). The liquid stream (7B) may be removed or discharged to the outside of the system.

(8) Distillation Step

As described above, the overhead stream (7A) still contains methyl iodide, although the concentration of methyl iodide is low. Thus, the overhead stream (7A) may further be distilled in the fourth distillation step (8) to reduce the concentration of methyl iodide. Specifically, the overhead stream (7A) from the distillation step (7) may further be distilled in the distillation step (8) to separate the overhead stream (7A) into an overhead stream (8A) and a bottom liquid stream (8B). Since the overhead stream (7A) has a concentrated (enriched) acetaldehyde, the distillation step (8) may preferably be conducted in a water extractive distillation. In more details, water is added to the top of the distillation column (separation column) of the fourth distillation step (8) via a feed line 82 for conducting the water extractive distillation, and the overhead stream (8A) is directly or indirectly recycled to the reaction step (1), and the bottom liquid stream (8B) containing acetaldehyde is withdrawn via a line 81. In the process shown in FIG. 1, the overhead stream (8A) is cooled and condensed in a condenser C6 on a line 83, a first portion of the condensate is returned or refluxed to the distillation column (separation column) (8) via a reflux line 84, and a second portion of the condensate is withdrawn via a line 85 for recycling to the reaction step (1).

For such a water extractive distillation, the overhead stream (8A) or a condensate thereof, which has a ratio of methyl iodide relative to acetaldehyde larger than that of the liquid stream (8B), may produce a condensate having a high methyl iodide concentration. The concentrate may be recycled to the reaction step (reactor) (1) via a line 85.

For the water extractive distillation, the water may have the same temperature as the extractant. The water may be added as a warmed or heated water having the same temperature as the extractant or as a vaporized water (or steam).

The bottom liquid stream or aqueous bottom stream (8B) is rich in the extractant (in particular, water) and acetaldehyde. Thus the bottom liquid stream (8B) may be discharged to the outside of the system; or may further be distilled to separate a PRC's fraction and a water fraction from each other, the PRC's fraction may be discharged to the outside of the system, and the water fraction may be recycled as an extractant for the distillation step (5); or may be recycled to the reaction step (reactor) (1).

The internal temperature of the distillation column of the fourth distillation step (8) depends on an internal pressure thereof. At the internal pressure of an atmospheric pressure, the distillation column may have a column top temperature of, for example, about 10 to 90° C. (e.g., about 15 to 80° C.) and preferably about 20 to 70° C. (e.g., about 20 to 65° C.), or may have a column bottom temperature of, for example, about 15 to 110° C. (e.g., about 20 to 100° C.) and preferably about 25 to 80° C. (e.g., about 30 to 70° C.). The distillation column may have a column top pressure of, for example, about 0.1 to 0.5 MPa, preferably about 0.2 to 0.4 MPa, and more preferably about 0.25 to 0.35 MPa in terms of absolute pressure.

The distillation column may have a theoretical stage (or plate) of, for example, about 1 to 50 (e.g., about 2 to 40) and preferably about 3 to 30 (e.g., about 5 to 10). The reflux ratio of the distillation column may be, for example, about 1 to 1000 (e.g., about 3 to 500), preferably about 5 to 100 (e.g., about 10 to 70), and more preferably about 15 to 50 (e.g., about 15 to 30).

The weight ratio of the flow rate of the extractant (water) relative to the flow rate of the condensate 74 of the third overhead stream (lower boiling point stream) (in terms of liquid stream) [the former/the latter] may be selected from the range of about 0.1/100 to 1000/100 (e.g., about 10/100 to 500/100) or may usually be about 25/100 to 250/100 (e.g., about 50/100 to 200/100) and preferably about 70/100 to 150/100 (e.g., about 75/100 to 125/100).

For the water extractive distillation, the extractant (water) may have a temperature of, for example, about 0 to 60° C., preferably about 10 to 50° C., and more preferably about 20 to 40° C. or may have an ordinary temperature (e.g., about 15 to 25° C.). The extractant (water) may be added as a warmed or heated extractant or in the form of vapor.

The internal temperature of the water extractive distillation column depends on an internal pressure thereof. At the internal pressure of an atmospheric pressure, the distillation column may have a column top temperature of, for example, about 10 to 90° C. (e.g., about 15 to 80° C.) and preferably about 20 to 70° C. (e.g., about 20 to 65° C.), or may have a column bottom temperature of, for example, about 15 to 110° C. (e.g., about 20 to 100° C.) and preferably about 25 to 80° C. (e.g., about 30 to 70° C.). The distillation column may have a column top pressure (absolute pressure) of, for example, about 0.1 to 0.5 MPa, preferably about 0.2 to 0.4 MPa, and more preferably about 0.25 to 0.35 MPa. The distillation column may have a column top pressure (gauge pressure) of about 0.0 to 0.5 MPa, preferably about 0.1 to 0.4 MPa, and more preferably about 0.15 to 0.35 MPa.

The distillation column may have a theoretical stage (or plate) of, for example, about 0.5 to 30 (e.g., about 1 to 20) and preferably about 2 to 10 (e.g., about 3 to 5). The reflux ratio of the distillation column may be, for example, about 0.01 to 500 (e.g., about 0.1 to 100), preferably about 0.5 to 50 (e.g., about 1 to 30), and more preferably about 2 to 20 (e.g., about 3 to 10). The overhead stream (8A) or a condensate thereof (the lines 83, 84, 85) is rich in acetaldehyde and methyl iodide. The condensate of the overhead stream (8A) may have a PRC (representatively acetaldehyde) concentration of, for example, about 1 to 70% by weight (e.g., about 10 to 65% by weight) and preferably about 30 to 60% by weight (e.g., about 35 to 55% by weight); or may have a PRC concentration of about 5 to 20% by weight (e.g., about 10 to 15% by weight). The condensate may have a methyl iodide concentration of, for example, about 20 to 80% by weight (e.g., about 30 to 75% by weight) and preferably about 40 to 65% by weight (e.g., about 45 to 60% by weight); or may have a methyl iodide concentration of about 50 to 90% by weight (e.g., about 60 to 85% by weight) and preferably about 70 to 80% by weight. The condensate may have a methyl acetate concentration of, for example, about 0.01 to 20% by weight (e.g., about 0.1 to 15% by weight) and preferably about 1 to 10% by weight (e.g., about 2 to 8% by weight); or may have a methyl acetate concentration of about 3 to 20% by weight (e.g., about 5 to 15% by weight). The condensate of the overhead stream (8A) may have an acetic acid concentration of, for example, about 0 to 5% by weight, preferably about 0 to 3% by weight, and more preferably about 0 to 1% by weight, or may have an acetic acid concentration substantially not more than detection limit. The condensate may have a water concentration of, for example, about 0 to 10% by weight (e.g., about 0.01 to 8% by weight) and preferably about 0.1 to 5% by weight (e.g., about 0.3 to 3% by weight).

The condensate of the overhead stream (8A) may have a dimethyl ether concentration that can be selected from a wide range of about 10 ppm to 80% by weight, and may have a dimethyl ether concentration of, for example, about 100 ppm to 60% by weight (e.g., about 0.5 to 50% by weight) and preferably about 1 to 40% by weight (e.g., about 5 to 30% by weight). The concentration of dimethyl ether in the overhead stream (8A), which varies depending on process conditions, may be increased in some cases. The condensate of the overhead stream (8A) may have a methanol concentration of, for example, about 0 to 5% by weight (e.g., about 0 to 3% by weight), preferably about 0 to 1% by weight (e.g., about 0 to 0.5% by weight), and more preferably about 0.001 to 0.3% by weight (e.g., about 0.01 to 0.1% by weight), or may have a methanol concentration substantially not more than detection limit.

The overhead stream (8A) (the reflux line 83) may have a temperature at an atmospheric pressure of, for example, about 10 to 90° C. (e.g., about 15 to 80° C.) and preferably about 20 to 70° C. (e.g., about 20 to 65° C.). The condensate (the lines 84, 85) of the overhead stream (8A) cooled in the condenser C6 may have a temperature of, for example, about 0 to 45° C. (e.g., about 3 to 35° C.) and preferably about 5 to 30° C. (e.g., about 7 to 25° C.).

The bottom liquid stream or aqueous bottom stream (8B) (the line 81) usually contains water as a main component and may contain acetaldehyde. The liquid stream (8B) may have a PRC (representatively acetaldehyde) concentration (on the basis of weight) of, for example, about 1 to 50% by weight (e.g., about 5 to 45% by weight) and preferably about 10 to 40% by weight (e.g., about 20 to 40% by weight), or may have a PRC concentration of about 2 to 15% by weight (e.g., about 5 to 10% by weight). The liquid stream (8B) may have a methyl iodide concentration of, for example, not more than 1% by weight (e.g., about 1 ppm to 0.8% by weight), not more than preferably 0.5% by weight (e.g., about 0.001 to 0.2% by weight), and more preferably not more than 0.005 to 0.15% by weight. The liquid stream (8B) may have a methyl acetate concentration of, for example, about 1 ppm to 5% by weight (e.g., about 50 ppm to 2% by weight) and preferably about 0.01 to 1.5% by weight (e.g., about 0.05 to 1% by weight). The liquid stream (8B) may have an acetic acid concentration of, for example, not more than 5% by weight (e.g., about 1 ppm to 3% by weight) and preferably not more than 1% by weight (e.g., about 50 ppm to 0.5% by weight), or may have an acetic acid concentration substantially not more than detection limit (0% by weight). The liquid stream (8B) may have a water concentration of, for example, about 40 to 90% by weight (e.g., about 50 to 85% by weight) and preferably about 55 to 80% by weight (e.g., about 60 to 80% by weight); or may have a water concentration of about 80 to 98% by weight (e.g., about 85 to 97% by weight) and preferably about 90 to 95% by weight. The liquid stream (8B) may have a dimethyl ether concentration of, for example, about 0 to 2% by weight (e.g., about 0.0001 to 1.5% by weight), preferably about 0.001 to 1% by weight (e.g., about 0.01 to 0.5% by weight), and more preferably about 0.1 to 0.5% by weight. The liquid stream (8B) may have a methanol concentration of, for example, about 0 to 5% by weight (e.g., about 0 to 3% by weight), preferably about 0 to 1% by weight (e.g., about 0 to 0.5% by weight), and more preferably about 0.001 to 0.3% by weight (e.g., about 0.01 to 0.1% by weight), or may have a methanol concentration substantially not more than detection limit.

The bottom liquid stream or aqueous bottom stream (8B) may have a temperature at atmospheric pressure of, for example, about 15 to 110° C. (e.g., about 20 to 100° C.) and preferably about 25 to 80° C. (e.g., about 30 to 70° C.).

Regardless of use of acetic acid as the miscible solvent, the second overhead stream (5A) and/or the side-cut stream (5B) as well as the succeeding process stream, for example, the condensate (the aqueous phase and/or the organic phase, in particular, the aqueous phase) from the liquid-liquid separation step (6) usually contain acetic acid and methyl acetate in addition to acetaldehyde and methyl iodide. The distillation of the process stream containing such components in the above third distillation step (7) distributes acetic acid or methyl acetate to the extractant (in particular, water) of the bottom liquid stream (7B) to separate acetaldehyde and methyl iodide from acetic acid. Specifically, the distillation column (7) allows efficient separation of acetic acid and methyl acetate from the process stream. Thus, water extractive distillation in the fourth distillation step (8) following the third distillation step (7) prevents methyl iodide from being mixed into the bottom liquid stream (8B), due to an affinity between water and acetaldehyde, to provide the bottom liquid stream or aqueous solution (8B) having an extremely high ratio (AD/MeI) of acetaldehyde (AD) relative to methyl iodide (MeI). Specifically, after acetic acid and methyl acetate are removed in the third distillation step (7) in addition to the second distillation step (5), further water extractive distillation is conducted in the fourth distillation step (8) to achieve energy saving and reduction of the cost of equipment in comparison with the conventional process, and in addition, to reduce a discharge loss of methyl iodide to the outside of the system. The AD/MeI ratio in the bottom liquid stream or aqueous solution (8B) may be, for example, about 20/1 to 2000/1 (e.g., about 50/1 to 1500/1), preferably about 100/1 to 1000/1 (e.g., about 150/1 to 750/1), and more preferably about 200/1 to 500/1 (e.g., about 250/1 to 450/1).

As described above, each one of the process streams (e.g., a process stream, such as the mixed composition (3A) or phases separated therefrom, or the side-cut stream (5B) or phases separated therefrom) usually contains other components (including impurities) inevitably. The process stream may have a methanol concentration of, for example, about 0 to 5% by weight (e.g., about 0.0001 to 3% by weight), preferably about 0.001 to 1% by weight (e.g., about 0.01 to 0.5% by weight), and more preferably about 0.1 to 0.5% by weight. The process stream may have a hydrogen iodide concentration of about 0 to 5000 ppm (e.g., about 1 to 1000 ppm) and preferably about 5 to 500 ppm (e.g., about 10 to 300 ppm). The process stream may have a concentration of each of formic acid and $C_{3-8}$alkanecarboxylic acids (such as propionic acid) of, for example, about 0 to 500 ppm (e.g., about 1 to 300 ppm) and preferably about 0 to 100 ppm (e.g., about 5 to 50 ppm). The process stream may have a concentration of each of acetaldehyde-derived aldehydes (such as crotonaldehyde and 2-ethylcrotonaldehyde) of, for example, about 0 to 500 ppm (e.g., about 1 to 300 ppm) and preferably about 0 to 100 ppm (e.g., about 5 to 50 ppm). The process stream may have a concentration of each of alkyl iodides ($C_{2-12}$ alkyl iodides such as hexyl iodide) of, for example, about 0 to 100 ppm (e.g., about 1 ppb to 50 ppm) and preferably about 0 to 10 ppm (e.g., about 10 ppb to 5 ppm).

The condensate (the aqueous phase and/or the organic phase, for example, the aqueous phase) from the liquid-liquid separation step (6) may be subjected to water extractive distillation in the fourth distillation step (8) without subjecting to the third distillation step (7).

By separating acetic acid or methyl acetate as a component in the bottom liquid stream (7B), the third overhead stream (7A) from the third distillation step (7) has a reduced distributability or dissolubility of methyl iodide to water. Thus, if necessary, acetaldehyde may be extracted with water from the third overhead stream (7A) by one or a plurality of water extraction units provided with a mixer and a settler or by an extraction column, instead of the fourth distillation step (8).

Further, the aqueous phase obtained by biphasically separating the extraction mixture (5B) and the overhead stream (5A) also contains methyl iodide. Thus, at least a portion of the aqueous phase obtained by biphasically separating the extraction mixture (5B) and/or the overhead stream (5A) may be subjected to water extraction in the extraction or extractive distillation step (8). Incidentally, at least a portion of the aqueous phase obtained by biphasically separating at least the extraction mixture (5B), among the extraction mixture (5B) and the overhead stream (5A), may practically be subjected to the extraction step (8). The above aqueous phase and/or the overhead stream (7A) from the distillation step (7) may be subjected to water extraction in the extraction step (8).

According to the present invention, as described above, various changes and modifications of the process unit and/or the process flow may be made. For example, in the second liquid-liquid separation step (6), the separation unit 6a is not necessarily needed. For example, as shown in FIG. 2, the overhead stream (5A) from the distillation step (5) may be cooled and condensed in the condenser C3, and the whole of the condensate may be refluxed in the distillation column (5) using a reflux unit 106 instead of the separation unit 6a. For refluxing the whole of the overhead stream (5A), the reflux unit 106 is not necessarily needed. The second liquid-liquid separation step (6) does not necessarily require a plurality of liquid-liquid separation units 6b and 6c. The second liquid-liquid separation step (6) may use a single liquid-liquid separation unit (such as a tank, a decanter, a hold tank, or a buffer tank).

The side-cut stream (5B) or the fluid (such as the aqueous phase) from the second liquid-liquid separation step (6) may be distilled in the fourth distillation step (8). The third distillation step (7) and/or the fourth distillation step (8) are not necessarily needed. Instead of the fourth distillation step (8), an extraction unit (such as an extraction column or an extractor) may be used. An aqueous solvent produced in the process may be used as an extractant in the second distillation step (5).

Although the first overhead stream (3A) (including a condensate thereof, and an aqueous phase and/or an organic phase liquid-liquid separated therefrom) corresponds to a mixed composition (or mixture) from which PRC's (e.g., acetaldehyde) are separated and removed according to the present invention, the mixed composition (or mixture) according to the present invention is not limited to the first overhead stream (3A) or a condensate thereof and may be any mixture containing at least a PRC (such as acetaldehyde) and methyl iodide, for example, a mixture produced from the reaction step (reaction system or reactor) (1), the flash evaporation step (flasher) (2), or the first distillation step (3); and a mixture produced from each one of steps following the second distillation step (5) [for example, the second liquid-liquid separation step (6), the third distillation step (third distillation column) (7), and the fourth distillation step (fourth distillation column) (8)]. According to the present invention, PRC's (e.g., acetaldehyde) and methyl iodide can effectively be separated from each other even in such a mixture (in particular, a mixture containing methyl acetate).

The process of the present invention is applicable to any mixed composition (or mixture) or overhead stream containing at least a PRC and methyl iodide (in particular, a mixed composition or an overhead stream from which a side-cut stream produced by distillation with the extractant is liquid-liquid separable), and is applicable for not only the second distillation column (5) but also one or a plurality of distillation columns following the first distillation column (3) to selectively separate PRC's by using extractive distillation in the concentration zone. In particular, the process of the present invention is effectively applicable to a mixed composition or overhead stream containing concentrated methyl iodide as described above in order to effectively extract PRC's with a small amount of the extractant in a small extraction space. In the mixed composition or overhead stream, at least methyl iodide, among permanganate reducing compounds (PRC's) and methyl iodide, may be concentrated, PRC's may also be concentrated, or the water concentration may be reduced, compared with a mixed stream produced in a preceding unit operation [for example, a stream fed to the first distillation column (3)]. The above unit operation may include one or a plurality of various unit operations, e.g., a flash step, a distillation step (including a water extractive distillation step), an extraction step, a condensation and liquid-liquid (biphasic) separation step, an absorption step, and a membrane separation step.

EXAMPLES

The following examples are intended to describe this invention in further detail and should by no means be interpreted as defining the scope of the invention.

Hereinafter, the results of experiments carried out using an Oldershaw distillation column having a diameter of 40 mmφ according to a process flow of Examples shown in FIG. 3 will be shown. In experiments according to the process of Examples shown in FIG. 3, the process shown in FIG. 1, which comprises a second distillation step (5), a liquid-liquid separation step (6), a third distillation step (7), and a fourth distillation step (8), were modified by replacing a separation unit 6a following the second distillation step (5) with a reflux unit 106, by disposing a decanter 6c without using a decanter 6a and a hold tank 6b, and by connecting or joining a line 63 for a extraction mixture (5B) to a cooling unit (cooler) C4. Accordingly, without using a line 64 and a line 67 shown in FIG. 1, an organic phase in the decanter 6c was recycled to the distillation step (5) via a line 68. In addition, an aqueous phase in the decanter 6c was recycled at a predetermined flow rate (a flow rate corresponding to a flow rate in a line 67 shown in FIG. 1) from the tank 6c to the distillation step (5) via a line 69a branched from a line 69. Acetic acid, as a miscible solvent, was fed via a feed line 70 at an intermediate position in height between a recycle line 65 and a feed line 44.

In a process of Comparative Example 1, a second distillation column (acetaldehyde-removing column) 206, an extraction column 207, and a distillation column 208 were used, as shown in FIG. 4.

In Comparative Example 1 and Examples 1 to 8, an organic phase (MeI-rich feed liquid) in a decanter (4) was fed to the distillation column of the second distillation step (5) via a feed line 44 shown in FIG. 1. In Examples 9 and 10, an aqueous phase (water-rich feed liquid) in the decanter (4) was also fed to the distillation column of the second distillation step (5) via a feed line 43b shown in FIG. 1. The aqueous phase in the feed line 43b was mixed (or merged) with the organic phase in the feed line 44, and the resulting mixture was fed to the same plate of the distillation column.

In the following Comparative Example and Examples, numerical values were expressed as follows. Measured values were rounded off to the second last digit. With respect to the measured values in Comparative Example and Examples, concentration values were basically expressed as one decimal place, and flow rate values expressed were determined by rounding off measured values. In Tables, the concentration of each component was basically expressed as one or two decimal places; for a component having a lower concentration, the concentration was expressed as three or four decimal places. In Tables, the sum total of the concentrations of the components described is not strictly 100% by weight in some cases. In such cases, the amount of the component having the maximum concentration is used as a balanced amount so that the sum total was expressed as 100% by weight. The amount of the component having the maximum concentration was shown as a balanced amount "BL". In the balanced amount "BL", traces of impurities or other components are also contained.

Comparative Example 1

A second distillation column 206 having the actual number of stages of 100 [acetaldehyde-removing column; column top temperature of 22° C., column bottom temperature of 48° C., column top pressure of atmospheric pressure+10 mmH$_2$O (about 100 Pa)] was provided. To the 32nd plate from the bottom of the distillation column 206, a feed liquid (a line 44, temperature: 20° C.) was fed at 1295 g/h. An overhead 262 (temperature: 22° C.) produced by the distillation was cooled to 7° C. in a condenser C3. A portion of the condensate was refluxed at a rate of 987 g/h (via a reflux line 263), and the residual portion of the condensate was distilled off via a line 264 at a rate of 6.0 g/h. The feed liquid was a methyl iodide (MeI) solution (or mixture) having an acetaldehyde (AD) concentration of 1960 ppm, a methyl acetate (MA) concentration of 14.9% by weight, a water concentration of 0.7% by weight, and an acetic acid (AC) concentration of 1.9% by weight. The condensate (the line 264) of the overhead had an AD concentration of 41.4% by weight (MeI solution or mixture). The MeI solution was fed to a top of an extraction column 207 having the number of theoretical stages of 1 [column top temperature of 15° C., column bottom temperature of 15° C., absolute pressure of about 0.1 MPa (atmospheric pressure)] via the line 264, water (temperature: 15° C.) was fed at a rate of 6.0 g/h to a bottom of the extraction column 207 via a line 271, and an aqueous extraction mixture (temperature: 15° C.) having an AD concentration of 26.4% by weight was withdrawn at a flow rate of 8.5 g/h from a top of the column (a line 275). The AD-containing aqueous extraction mixture was fed to a distillation column (AD separation column) 208 (column top temperature of 21° C., column bottom temperature of 102° C., column top pressure of atmospheric pressure+10 mmH$_2$O) via a feed line 275 and distilled to form an overhead 282 having a temperature of 21° C. The overhead 282 was cooled in a condenser C6 to give a condensate (temperature: 7° C.). A portion of the condensate was refluxed at a rate of 25.3 g/h (via a reflux line 283), and the residual portion of the condensate, which had an AD concentration of 88.8% by weight and a MeI concentration of 10.8% by weight (temperature: 7° C.), was withdrawn at a flow rate of 2.53 g/h via a withdrawing line 284. From a bottom of the column, a bottom stream (temperature: 102° C.) was withdrawn via a line 281. According to the process, AD and MeI were removed from the process at a flow rate of 2.25 g/h and a flow rate of 0.27 g/h, respectively. The second distillation column (acetaldehyde-removing column) 206 required a reboiler heat quantity of 100.2 kcal/h, and the AD separation column 208 required a reboiler heat quantity of 4.3 kcal/h.

Table 1 shows componential analysis in each line depicted in FIG. 4.

TABLE 1

| Composition in Line No. depicted in FIG. 4 (% by weight) | | | | | |
|---|---|---|---|---|---|
| Line No. | 44 | 261 | 262/ 263/264 | 272 | 275 | 282/ 283/284 |
| AD | 0.196 | 0.0038 | 41.39 | 6.79 | 26.39 | BL |
| MeI | BL | BL | BL | BL | 3.22 | 10.83 |
| MA | 14.89 | 14.96 | 0.33 | 0.37 | 0.08 | 0.26 |
| H$_2$O | 0.70 | 0.70 | 0.53 | 1.27 | BL | 0.14 |
| AC | 1.90 | 1.91 | 0.00 | 0.00 | 0.00 | 0.00 |
| Total | 100 | 100 | 100 | 100 | 100 | 100 |

In Table 1, AD indicates acetaldehyde, MeI indicates methyl iodide, MA indicates methyl acetate, and AC indicates acetic acid (the same applies hereinafter).

Example 1

A second distillation column 5 having the actual number of stages of 43 [column top temperature of 23° C., column bottom temperature of 47° C., column top pressure of atmospheric pressure+10 mmH$_2$O (about 100 Pa)] was provided. A feed liquid (a line 44, temperature: 20° C.) was fed to the 7th plate from the bottom of the distillation column at a rate of 1295 g/h, and water (temperature: 20° C.) was fed to the 43rd plate from the bottom of the distillation column at a rate of 12.5 g/h. An overhead (temperature: 23° C.) from a line 53 was cooled in condenser C3 to 7° C. and was refluxed at a reflux rate of 576 g/h for water extractive distillation in the column. The feed liquid was a methyl iodide solution having an AD concentration of 1960 ppm, a MA concentration of 14.8% by weight, a water concentration of 0.7% by weight, and an AC concentration of 1.8% by weight. A chimney tray was installed instead of the third plate below the top of the column, and the whole amount of the falling liquid was withdrawn as a side-cut stream 63 (temperature: 36° C.). The side-cut stream was cooled in a cooling unit C4 to 15° C. and was then introduced into a hold tank 6c to form two phases of an aqueous phase and an organic phase (MeI phase). A bottom stream from a line 52 (temperature: 47° C.) was withdrawn at a rate of 1285 g/h. The whole amount of the aqueous phase (temperature: 15° C.) having an AD concentration of 15.8% by weight was withdrawn at a rate of 15.6 g/h from the tank 6c to the outside of the system via a line 69 without recycling to the second distillation column 5, and AD was thus removed. The whole amount (808.9 g/h) of the MeI phase (a line 68, temperature: 15° C.) in the tank 6c was recycled to the first plate below the chimney tray (the fourth plate below the top of the column) of the second distillation column (acetaldehyde-removing column) 5. According to the process, AD and MeI in the aqueous phase (the line 69) were removed from the process at a flow rate of 2.47 g/h and a flow rate of 0.22 g/h, respectively. The second distillation column 5 required a reboiler heat quantity of 56.1 kcal/h. The rate withdrawn from the bottom (the line 52) of the second distillation column 5 was 1285 g/h.

The following Table shows the results of componental analysis in each line depicted in FIG. 3.

TABLE 2

Composition in Line No. depicted in FIG. 3 (% by weight)

| Line No. | 44 | 52 | 53/61 | 63 | 65/68 | 69 |
|---|---|---|---|---|---|---|
| AD | 0.196 | 0.004 | 38.12 | 2.73 | 2.47 | 15.77 |
| Mel | BL | BL | BL | BL | BL | 1.43 |
| MA | 14.77 | 14.89 | 0.38 | 2.33 | 2.36 | 0.94 |
| $H_2O$ | 0.70 | 0.70 | 0.39 | 1.71 | 0.16 | BL |
| AC | 1.83 | 1.85 | 0.00 | 0.00 | 0.00 | 0.00 |
| Total | 100 | 100 | 100 | 100 | 100 | 100 |

Example 2

A second distillation column 5 having the actual number of stages of 43 [column top temperature of 22° C., column bottom temperature of 47° C., column top pressure of atmospheric pressure+10 mmH$_2$O (about 100 Pa)] was provided. A feed liquid (a line 44, temperature: 20° C.) was fed to the 7th plate from the bottom of the distillation column at a rate of 1302 g/h, and water (temperature: 20° C.) was fed to the 43rd plate from the bottom of the distillation column at a rate of 12.5 g/h. An overhead (temperature: 22° C.) from a line 53 was cooled in condenser C3 to 7° C. and was refluxed at a reflux rate of 937 g/h for water extractive distillation in the column. The feed liquid was a methyl iodide solution having an AD concentration of 1940 ppm, a MA concentration of 14.8% by weight, a water concentration of 0.7% by weight, and an AC concentration of 2.1% by weight. A chimney tray was installed instead of the third plate below the top of the column, and the whole amount of the falling liquid was withdrawn as a side-cut stream 63 (temperature: 34° C.). The side-cut stream was cooled in a cooling unit C4 to 15° C. and was then introduced into a hold tank 6c to form two phases of an aqueous phase and an organic phase. A bottom stream from a line 52 (temperature: 47° C.) was withdrawn at a rate of 1294 g/h. A first portion of the aqueous phase having an AD concentration of 20.5% by weight was withdrawn at a rate of 11.9 g/h from the tank 6c to the outside of the system via a line 69 without recycling to the second distillation column 5, and AD was thus removed. A second portion of the aqueous phase (a line 69a, temperature: 15° C.) was withdrawn at a flow rate of 7.4 g/h from the tank 6c and mixed (or merged) with the whole amount (1345 g/h) of the MeI phase (a line 68, temperature: 15° C.) withdrawn from the tank 6c (a line 65), and the resulting mixture was recycled to the first plate below the chimney tray (the fourth plate below the top of the column).

According to the process, AD and MeI in the aqueous phase (the line 69) were removed from the process at a flow rate of 2.44 g/h and a flow rate of 0.18 g/h, respectively. The second distillation column 5 required a reboiler heat quantity of 89.7 kcal/h. The rate withdrawn from the bottom (the line 52) of the second distillation column 5 was 1294 g/h.

The following Table shows the results of componental analysis in each line depicted in FIG. 3.

TABLE 3

Composition in Line No. depicted in FIG. 3 (% by weight)

| Line No. | 44 | 52 | 53/61 | 63 | 68 | 69/69a |
|---|---|---|---|---|---|---|
| AD | 0.194 | 0.005 | 41.12 | 3.73 | 3.49 | 20.54 |
| Mel | BL | BL | BL | BL | BL | 1.56 |
| MA | 14.76 | 14.83 | 0.29 | 2.26 | 2.28 | 0.75 |
| $H_2O$ | 0.70 | 0.97 | 0.33 | 1.28 | 0.19 | BL |
| AC | 2.08 | 2.09 | 0.00 | 0.00 | 0.00 | 0.00 |
| Total | 100 | 100 | 100 | 100 | 100 | 100 |

Example 3

A second distillation column 5 having the actual number of stages of 43 [column top temperature of 22° C., column bottom temperature of 47° C., column top pressure of atmospheric pressure+10 mmH$_2$O (about 100 Pa)] was provided. A feed liquid (a line 44, temperature: 20° C.) was fed to the 7th plate from the bottom of the distillation column at a rate of 1279 g/h, and water (temperature: 20° C.) was fed to the 43rd plate from the bottom of the distillation column at a rate of 12.6 g/h. An overhead (temperature: 22° C.) from a line 53 was cooled in condenser C3 to 7° C. and was refluxed at a reflux rate of 688 g/h for water extractive distillation in the column. The feed liquid was a methyl iodide solution having an AD concentration of 1960 ppm, a MA concentration of 14.8% by weight, a water concentration of 0.7% by weight, and an AC concentration of 1.8% by weight. A chimney tray was installed instead of the third plate below the top of the column, and the whole amount of the falling liquid was withdrawn as a side-cut stream 63 (temperature: 34° C.). The side-cut stream was cooled in a cooling unit C4 to 15° C. and was then introduced into a hold tank 6c to form two phases of an aqueous phase and an organic phase (MeI phase). A bottom stream from a line 52 (temperature: 47° C.) was withdrawn at a rate of 1299 g/h. The whole amount of the aqueous phase (temperature: 15° C.) having an AD concentration of 16.0% by weight was withdrawn at a rate of 15.3 g/h from the tank 6c to the outside of the system via a line 69 without recycling to the second distillation column 5, and AD was thus removed. The whole amount of the MeI phase (a line 68, temperature: 15° C.) in the tank 6c was recycled at a rate of 1013 g/h to the first plate below the chimney tray (the fourth plate below the top of the column) of the second distillation column (acetaldehyde-removing column) 5.

Further, acetic acid (temperature: 20° C.) was fed at a flow rate of 30.0 g/h to the 21st plate below the top of the second distillation column 5 (the 17th plate below the recycle plate) via a line 70.

According to the process, AD and MeI in the aqueous phase (the line 69) were removed from the process at a flow rate of 2.45 g/h and a flow rate of 0.18 g/h, respectively. The second distillation column 5 required a reboiler heat quantity of 66.1 kcal/h. The rate withdrawn from the bottom of the second distillation column 5 was 1299 g/h.

The following Table shows the results of componental analysis in each line depicted in FIG. 3.

TABLE 4

| Composition in Line No. depicted in FIG. 3 (% by weight) | | | | | |
|---|---|---|---|---|---|
| Line No. | 44 | 52 | 53/61 | 63 | 68/65 | 69 |
| AD | 0.196 | 0.004 | 38.74 | 2.67 | 2.47 | 15.97 |
| MeI | BL | BL | BL | BL | BL | 1.20 |
| MA | 14.77 | 14.54 | 0.15 | 0.94 | 0.95 | 0.50 |
| $H_2O$ | 0.70 | 0.71 | 0.37 | 1.34 | 0.11 | BL |
| AC | 1.83 | 4.11 | 0.00 | 0.00 | 0.00 | 0.00 |
| Total | 100 | 100 | 100 | 100 | 100 | 100 |

Example 4

A second distillation column 5 having the actual number of stages of 43 [column top temperature of 22° C., column bottom temperature of 47° C., column top pressure of atmospheric pressure+10 mmH₂O (about 100 Pa)] was provided. A feed liquid (a line 44, temperature: 20° C.) was fed to the 7th plate from the bottom of the distillation column at a rate of 1290 g/h, and water (temperature: 20° C.) was fed to the 43rd plate from the bottom of the distillation column at a rate of 12.5 g/h. An overhead (temperature: 22° C.) from a line 53 was cooled in condenser C3 to 7° C. and was refluxed at a reflux rate of 899 g/h for water extractive distillation in the column. The feed liquid was a methyl iodide solution having an AD concentration of 1940 ppm, a MA concentration of 14.8% by weight, a water concentration of 0.70% by weight, and an AC concentration of 2.1% by weight. A chimney tray was installed instead of the third plate below the top of the column, and the whole amount of the falling liquid was withdrawn as a side-cut stream 63 (temperature: 34° C.). The side-cut stream was cooled in a cooling unit C4 to 15° C. and was then introduced into a hold tank 6c to form two phases of an aqueous phase and an organic phase. A first portion of the aqueous phase (temperature: 15° C.) having an AD concentration of 20.3% by weight was withdrawn at a rate of 11.9 g/h from the tank 6c via a line 69 without recycling to the second distillation column 5, and AD was thus removed. A second portion of the aqueous phase (a line 69a) was withdrawn at a flow rate of 7.4 g/h from the tank 6c and mixed with the whole amount (1305 g/h) of the MeI phase (a line 68, temperature: 15° C.) withdrawn from the tank 6c (a line 65), and the resulting mixture was recycled to the first plate below the chimney tray (the fourth plate below the top of the column). The rate withdrawn from the bottom stream (the line 52, temperature: 47° C.) of the second distillation column 5 was 1312 g/h.

Further, acetic acid (temperature: 20° C.) was fed at a flow rate of 30.0 g/h to the 21st plate below the top of the second distillation column 5 (the 17th plate below the recycle plate) via a line 70.

Then, the aqueous phase (the line 69) in the decanter 6c was fed to a third distillation column having the actual number of stages of 6 [AD-removing column; column top temperature: 21° C., column bottom temperature: 99° C., column top pressure: atmospheric pressure+10 mmH₂O (about 100 Pa)] 7. An overhead (temperature: 21° C.) from a line 72 was cooled in a condenser C5 to 7° C. and refluxed at a reflux rate of 12.5 g/h by distillation. A distillate (condensate) having an AD concentration of 92.4% by weight was withdrawn at a flow rate of 2.62 g/h via a line 74. An aqueous mixture (temperature: 99° C.) having a methyl acetate concentration of 0.1% by weight was withdrawn from the bottom via a line 71 for removal of methyl acetate. A fourth distillation column having the actual number of stages of 6 [water extractive distillation column; column top temperature: 28° C., column bottom temperature: 35° C., column top pressure: atmospheric pressure+10 mmH₂O (about 100 Pa)] 8 was provided. The distillate after removal of methyl acetate was fed to the 1st plate from the bottom of the distillation column 8 via a line 74, and water (temperature: 20° C.) was fed at a rate of 5.2 g/h to the top of the column. An overhead (temperature: 28° C.) from the line 83 was cooled in a condenser C6 to 7° C. and refluxed at a reflux rate of 6.0 g/h for water extractive distillation. A condensate solution (a line 85) having an AD concentration of 42.9% by weight and a MeI concentration of 51.7% by weight was withdrawn at a rate of 0.3 g/h from the top of the column, and an aqueous mixture (temperature: 35° C.) having an AD concentration of 30.3% by weight and a MeI concentration of 0.073% by weight was withdrawn at 7.6 g/h from the bottom (a line 81).

According to the process, AD and MeI in the aqueous phase (the line 69) were removed from the process at a flow rate of 2.42 g/h and a flow rate of 0.16 g/h, respectively. Further, AD and MeI in the bottom (the line 81) were removed from the process at a flow rate of 2.29 g/h and a flow rate of 0.0055 g/h, respectively. The second distillation column 5 required a reboiler heat quantity of 86.4 kcal/h. The third distillation column (AD-removing column) 7 required a reboiler heat quantity of 3.0 kcal/h. The water extractive distillation column 8 required a reboiler heat quantity of 0.7 kcal/h.

The following Table shows the results of componential analysis in each line depicted in FIG. 3.

TABLE 5

| Composition in Line No. depicted in FIG. 3 (% by weight) | | | | | | | | |
|---|---|---|---|---|---|---|---|---|
| Line No. | 44 | 52 | 53/61 | 63 | 69/69a | 68 | 71 | 72/73/74 |
| AD | 0.194 | 0.005 | 41.33 | 3.51 | 20.34 | 3.39 | 0.0001 | BL |
| MeI | BL | BL | BL | BL | 1.35 | BL | 0.0001 | 6.13 |
| MA | 14.76 | 14.50 | 0.15 | 1.18 | 0.40 | 1.19 | 0.10 | 1.46 |
| $H_2O$ | 0.70 | 0.96 | 0.32 | 0.72 | BL | 0.15 | BL | 0.00 |
| AC | 2.08 | 4.33 | 0.00 | 0.00 | 0.00 | 0.00 | 0.00 | 0.00 |
| Total | 100 | 100 | 100 | 100 | 100 | 100 | 100 | 100 |

Example 5

A second distillation column 5 having the actual number of stages of 43 [column top temperature of 22° C., column bottom temperature of 47° C., column top pressure of atmospheric pressure+10 mmH₂O (about 100 Pa)] was provided. A feed liquid (a line 44, temperature: 20° C.) was fed to the 7th plate from the bottom of the distillation column at a rate of 1290 g/h, and water (temperature: 20° C.)

was fed to the 43rd plate from the bottom of the distillation column at a rate of 12.5 g/h. An overhead (temperature: 22° C.) from a line 53 was cooled in condenser C3 to 7° C. and was refluxed at a reflux rate of 899 g/h for water extractive distillation in the column. The feed liquid was a methyl iodide solution having an AD concentration of 1940 ppm, a MA concentration of 14.8% by weight, a water concentration of 0.7% by weight, and an AC concentration of 2.1% by weight. A chimney tray was installed instead of the third plate below the top of the column, and the whole amount of the falling liquid was withdrawn as a side-cut stream 63 (temperature: 34° C.) The side-cut stream was cooled in a cooling unit C4 to 15° C. and was then introduced into a hold tank 6c to form two phases of an aqueous phase and an organic phase. A first portion of the aqueous phase (temperature: 15° C.) having an AD concentration of 20.3% by weight was withdrawn at a rate of 11.9 g/h from the tank 6c via a line 69 and was fed to the after-mentioned fourth distillation column (water extractive distillation column) 8. A second portion of the aqueous phase (a line 69a) was withdrawn at a flow rate of 7.4 g/h from the tank 6c and mixed with the whole amount (1305 g/h) of the MeI phase (a line 68, temperature: 15° C.) withdrawn from the tank 6c, and the resulting mixture was recycled to the first plate below the chimney tray (the fourth plate below the top of the column). The rate withdrawn from the bottom stream (the line 52, temperature: 47° C.) of the second distillation column 5 was 1312 g/h.

Further, acetic acid (temperature: 20° C.) was fed at a flow rate of 30.0 g/h to the 21st plate below the top of the second distillation column 5 (the 17th plate below the recycle plate) via a line 70.

Then, the aqueous phase (the line 69) withdrawn from the decanter 6c at a rate of 11.9 g/h was directly fed to the first plate from the bottom of a fourth distillation column having the actual number of stages of 6 [water extractive distillation column; column top temperature of 32° C., column bottom temperature of 70° C., column top pressure: atmospheric pressure+10 mmH$_2$O (about 100 Pa)] 8 without being fed to the third distillation column (AD-removing column) 7, and water (temperature of 20° C.) was fed to the top of the fourth distillation column at a rate of 23.9 g/h. An overhead (temperature of 32° C.) from a line 83 was cooled in a condenser C6 to 15° C. and refluxed at a reflux rate of 1.8 g/h for water extractive distillation. A condensate solution having an AD concentration of 12.5% by weight and a MeI concentration of 76.4% by weight was withdrawn from the top of the column at 0.20 g/h, and an aqueous mixture (temperature of 70° C.) having an AD concentration of 6.7% by weight and a MeI concentration of 0.022% by weight was withdrawn from the bottom (a line 81) at a rate of 35.6 g/h.

According to the process, AD and MeI in the bottom (the line 81) were removed from the process at a flow rate of 2.40 g/h and a flow rate of 0.0078 g/h, respectively. The second distillation column 5 required a reboiler heat quantity of 86.4 kcal/h. The water extractive distillation column 8 required a reboiler heat quantity of 2.1 kcal/h.

The following Table shows the results of componential analysis in each line depicted in FIG. 3. The compositions of the lines 44, 52, 53/61, 63, 69a, 69, and 68 are the same as those in Example 4 and are omitted from the following Table. The composition of the line 69 is the same as that of the feed line 74, which is fed to the distillation column 8 without passing through the distillation column 7.

TABLE 6

| | Composition in Line No. depicted in FIG. 3 (% by weight) | | |
|---|---|---|---|
| Line No. | 74/69 | 81 | 84/85 |
| AD | 20.34 | 6.73 | 12.47 |
| MeI | 1.35 | 0.022 | BL |
| MA | 0.40 | 0.08 | 10.06 |
| H$_2$O | BL | BL | 1.05 |
| AC | 0.00 | 0.00 | 0.00 |
| Total | 100 | 100 | 100 |

Table 7 and Table 8 represent the distillation operation of feed liquid, the separation efficiency of PRC's and methyl iodide, and the energy efficiency.

TABLE 7

| | Number of distillation stages (stages) | Removal amount of AD (g/h) | Lost amount of MeI (g/h) | MeI/AD ratio | Reboiler Duty (kcal/h) | | | |
|---|---|---|---|---|---|---|---|---|
| | | | | | 2nd distillation column | 3rd distillation column | 4th distillation column | Total |
| Comparative Example 1 | 100 | 2.25 | 0.27 | 0.122 | 100.2 | 4.3 | — | 104.5 |
| Example 1 | 43 | 2.47 | 0.22 | 0.091 | 56.1 | — | — | 56.1 |
| Example 2 | 43 | 2.44 | 0.18 | 0.076 | 89.7 | — | — | 89.7 |
| Example 3 | 43 | 2.45 | 0.18 | 0.075 | 66.1 | — | — | 66.1 |
| Example 4 | 43 | 2.42 | 0.16 | 0.066 | 86.4 | 3.0 | 0.7 | 90.1 |

In Comparative Example 1, the removal amount of AD and the lost amount of MeI indicate the amount of AD and the amount of MeI in the aqueous extract 275 from the water extractive distillation column 207 in FIG. 4. In Examples, the removal amount of AD and the lost amount of MeI indicate the amount of AD and the amount of MeI in the aqueous phase 69 formed by a mixture from the second distillation column (5). In Comparative Example 1, the methyl iodide/acetaldehyde ratio (MeI/AD ratio) was calculated from the amount of AD and the amount of MeI in the aqueous extract 275. In Examples 1 to 4, the methyl iodide/acetaldehyde ratio (MeI/AD ratio) was calculated from the amount of AD and the amount of MeI in the aqueous phase 69.

TABLE 8

|  | Number of distillation stages (stages) | Removal amount of AD (g/h) | Lost amount of MeI (g/h) | MeI/AD ratio | Reboiler Duty (kcal/h) | | | |
|---|---|---|---|---|---|---|---|---|
|  |  |  |  |  | 2nd distillation column | 3rd distillation column | 4th distillation column | Total |
| Comparative Example 1 | 100 | 2.25 | 0.27 | 0.122 | 100.2 | 4.3 | — | 104.5 |
| Example 4 | 43 | 2.29 | 0.0055 | 0.0024 | 86.4 | 3.0 | 0.7 | 90.1 |
| Example 5 | 43 | 2.40 | 0.0078 | 0.0032 | 86.4 | — | 2.1 | 88.5 |

In Comparative Example 1, the removal amount of AD and the lost amount of MeI indicate the amount of AD and the amount of MeI in the distillate 284, which was obtained by further distilling, by the distillation column 208, the aqueous extract 275 from the water extractive distillation column 207 in FIG. 4. In Examples 4 and 5, the removal amount of AD and the lost amount of MeI indicate the amount of AD and the amount of MeI in the bottom stream 81 from the fourth distillation column (8). In Comparative Example 1, the methyl iodide/acetaldehyde ratio (MeI/AD ratio) was calculated from the amount of AD and the amount of MeI in the distillate 284. In Examples 4 and 5, the methyl iodide/acetaldehyde ratio (MeI/AD ratio) was calculated from the amount of AD and the amount of MeI in the bottom liquid 81.

The comparison between Comparative Example 1 and Examples 1 to 3 in Table 7 shows that the water extractive distillation by the second distillation column (acetaldehyde-removing column) (5) according to the present invention reduces the number of stages required for the distillation column from 100 to 43 and also reduces the required steam amount. The comparison of Example 1 with Example 2, and the comparison of Example 1 with Example 3 show that not only withdrawing the aqueous phase of the side-cut stream to the outside of the system but also recycling a portion of the aqueous phase to the distillation column or further feeding acetic acid to the second distillation column reduces the concentration of methyl acetate in the second distillation column (5) to decrease the outflow of methyl iodide to the outside of the system. The comparison of Examples 2 and 3 with Example 4 shows that combination of the recycling of the aqueous phase and the feeding of acetic acid further reduces the lost amount of methyl iodide compared with the recycling of the aqueous phase in the second distillation column (5) alone or the feeding of acetic acid alone.

Furthermore, as apparent from Table 8, the water extractive distillation by the fourth distillation column (8) reduces the lost amount of methyl iodide. The comparison between Example 4 and Example 5 shows that removal of methyl acetate by the third distillation column (AD-removing column) (7) previous to the water extractive distillation by the fourth distillation column (8) further reduces a loss of methyl iodide in the water extractive distillation.

Example 6

A second distillation column 5 having the actual number of stages of 30 [column top temperature of 21.2° C., column bottom temperature of 49.1° C., column top pressure of atmospheric pressure+10 mmH$_2$O (about 100 Pa)] was provided. A feed liquid (a line 44, temperature: 21° C.) was fed to the 7th plate from the bottom of the distillation column at a rate of 1282 g/h, and water (temperature: 20° C.) was fed to the 30th plate from the bottom of the distillation column at a rate of 6.7 g/h. An overhead (temperature: 21.2° C.) from a line 53 was cooled in condenser C3 to 7° C. and was refluxed at a reflux rate of 295 g/h for water extractive distillation in the column. The feed liquid was a methyl iodide solution having an AD concentration of 1840 ppm, a MeI concentration of 82.6% by weight, a MeOH concentration of 0.07% by weight, a MA concentration of 13.9% by weight, a water concentration of 0.69% by weight, and an AC concentration of 2.5% by weight. A chimney tray was installed instead of the third plate below the top of the column, and the whole amount of the falling liquid was withdrawn as a side-cut stream 63 (temperature: 37.6° C.). The side-cut stream was cooled in a cooling unit C4 to 6.8° C. and was then introduced into a hold tank 6c to form two phases of an aqueous phase and an organic phase. A first portion of the aqueous phase having an AD concentration of 22.2% by weight (temperature: 6.8° C.) was withdrawn at a rate of 9.4 g/h from the tank 6c via a line 69. A second portion of the aqueous phase (a line 69a) was withdrawn at a flow rate of 9.3 g/h from the tank 6c and mixed (or merged) with the whole amount (968 g/h) of the MeI phase (a line 68, temperature: 7° C.) withdrawn from the tank 6c, and the resulting mixture was recycled to the first plate below the chimney tray (the fourth plate below the top of the column). The rate withdrawn from the bottom stream (the line 52, temperature: 49.1° C.) of the second distillation column 5 was 1279 g/h.

According to the process, by withdrawing the aqueous phase (the line 69) formed by the side-cut stream from the second distillation column 5, AD and MeI were removed from the process at a flow rate of 2.09 g/h and a flow rate of 0.167 g/h, respectively. The second distillation column 5 required a reboiler heat quantity of 47.7 kcal/h.

The following Table shows the results of componential analysis in each line depicted in FIG. 3. The aqueous phase in the line 69 was fed to the fourth distillation column 8 without being fed to the third distillation column 7. Thus the composition of the aqueous phase in the line 69 is the same as the composition of the feed line 74 connected to the distillation column 8.

TABLE 9

| Composition in Line No. depicted in FIG. 3 (% by weight) | | | | | | |
|---|---|---|---|---|---|---|
| Line No. | 44 | 52 | 53/61 | C3 vent | 63 | 68 | 69/69a |
| DME | 0.002 | 0.000 | 0.31 | 15.8 | 0.03 | 0.03 | 0.042 |
| AD | 0.184 | 0.0036 | 44.1 | BL | 6.0 | 5.7 | 22.2 |
| MeI | BL | BL | BL | 36.8 | BL | BL | 1.8 |
| MeOH | 0.07 | 0.041 | 0.06 | 0.0 | 0.3 | 0.3 | 4.0 |

TABLE 9-continued

Composition in Line No. depicted in FIG. 3 (% by weight)

| Line No. | 44 | 52 | 53/61 | C3 vent | 63 | 68 | 69/69a |
|---|---|---|---|---|---|---|---|
| MA | 13.9 | 13.9 | 0.50 | 7.0 | 1.7 | 1.8 | 0.7 |
| H₂O | 0.69 | 0.69 | 0.10 | 0.0 | 1.4 | 0.1 | BL |
| AC | 2.5 | 2.5 | 0.00 | 0.0 | 0.00 | 0.00 | 0.00 |
| Total | 100 | 100 | 100 | 100 | 100 | 100 | 100 |

In Table 9, DME indicates dimethyl ether, and MeOH indicates methanol (the same applies hereinafter).

Example 7

A second distillation column 5 having the actual number of stages of 15 [column top temperature of 21.0° C., column bottom temperature of 45.1° C., column top pressure of atmospheric pressure+10 mmH₂O (about 100 Pa)] was provided. A feed liquid (a line 44, temperature: 21° C.) was fed to the 7th plate from the bottom of the distillation column at a rate of 1295 g/h, and water (temperature: 21° C.) was fed to the 15th plate from the bottom of the distillation column at a rate of 4.2 g/h. An overhead (temperature: 21.0° C.) from a line 53 was cooled in condenser C3 to 5.8° C. and was refluxed at a reflux rate of 298 g/h for water extractive distillation in the column. The feed liquid was a methyl iodide solution having an AD concentration of 1710 ppm, a MeI concentration of 83.1% by weight, a MeOH concentration of 0.08% by weight, a MA concentration of 14.0% by weight, a water concentration of 0.61% by weight, and an AC concentration of 2.0% by weight. A chimney tray was installed instead of the third plate below the top of the column, and the whole amount of the falling liquid was withdrawn as a side-cut stream 63 (temperature: 36.7° C.). The side-cut stream was cooled in a cooling unit C4 to 5.8° C. and was then introduced into a hold tank 6c to form two phases of an aqueous phase and an organic phase. A first portion of the aqueous phase having an AD concentration of 18.3% by weight (temperature: 7° C.) was withdrawn at a rate of 10.1 g/h from the tank 6c via a line 69. A second portion of the aqueous phase (a line 69a) was withdrawn at a flow rate of 3.0 g/h from the tank 6c and mixed (or merged) with the whole amount (971 g/h) of the MeI phase (a line 68, temperature: 5.8° C.) withdrawn from the tank 6c, and the resulting mixture was recycled to the first plate below the chimney tray (the fourth plate below the top of the column). The rate withdrawn from the bottom stream (the line 52, temperature: 45.1° C.) of the second distillation column 5 was 1289 g/h.

According to the process, by withdrawing the aqueous phase (the line 69) formed by the side-cut stream from the second distillation column 5, AD and MeI were removed from the process at a flow rate of 1.85 g/h and a flow rate of 0.17 g/h, respectively. The second distillation column 5 required a reboiler heat quantity of 42.7 kcal/h.

The following Table shows the results of componential analysis in each line depicted in FIG. 3. The aqueous phase in the line 69 was fed to the fourth distillation column 8 without being fed to the third distillation column 7. Thus the composition of the aqueous phase in the line 69 is the same as the composition of the feed line 74 connected to the distillation column 8.

TABLE 10

Composition in Line No. depicted in FIG. 3 (% by weight)

| Line No. | 44 | 52 | 53/61 | C3 vent | 63 | 68 | 69/69a |
|---|---|---|---|---|---|---|---|
| DME | 0.003 | 0.000 | 0.61 | 28.2 | 0.06 | 0.06 | 0.08 |
| AD | 0.171 | 0.011 | 45.8 | BL | 7.1 | 6.9 | 18.3 |
| MeI | BL | BL | BL | 12.8 | BL | BL | 1.7 |
| MeOH | 0.08 | 0.049 | 0.08 | 0.0 | 0.1 | 0.0 | 4.0 |
| MA | 14.0 | 14.0 | 0.5 | 2.6 | 3.7 | 3.7 | 1.6 |
| H₂O | 0.61 | 0.36 | 0.2 | 0.0 | 1.2 | 0.2 | BL |
| AC | 2.0 | 2.0 | 0.0 | 0.0 | 0.0 | 0.0 | 0.0 |
| Total | 100 | 100 | 100 | 100 | 100 | 100 | 100 |

Example 8

A second distillation column 5 having the actual number of stages of 10 [column top temperature of 21.1° C., column bottom temperature of 45.2° C., column top pressure of atmospheric pressure+10 mmH₂O (about 100 Pa)] was provided. A feed liquid (a line 44, temperature: 21° C.) was fed to the 3rd plate from the bottom of the distillation column at a rate of 1303 g/h, and water (temperature: 21° C.) was fed to the 10th plate from the bottom of the distillation column at a rate of 6.3 g/h. An overhead (temperature: 21.1° C.) from a line 53 was cooled in condenser C3 to 5.8° C. and was refluxed at a reflux rate of 300 g/h for water extractive distillation in the column. The feed liquid was a methyl iodide solution having an AD concentration of 1790 ppm, a MeI concentration of 83.2% by weight, a MeOH concentration of 0.09% by weight, a MA concentration of 13.9% by weight, a water concentration of 0.66% by weight, and an AC concentration of 1.95% by weight. A chimney tray was installed instead of the third plate below the top of the column, and the whole amount of the falling liquid was withdrawn as a side-cut stream 63 (temperature: 36.7° C.). The side-cut stream was cooled in a cooling unit C4 to 5.8° C. and was then introduced into a hold tank 6c to form two phases of an aqueous phase and an organic phase. A first portion of the aqueous phase having an AD concentration of 21.0% by weight (temperature: 5.8° C.) was withdrawn at a rate of 8.8 g/h from the tank 6c via a line 69. A second portion of the aqueous phase (a line 69a) was withdrawn at a flow rate of 9.5 g/h from the tank 6c and mixed (or merged) with the whole amount (971 g/h) of the MeI phase (a line 68, temperature: 5.8° C.) withdrawn from the tank 6c, and the resulting mixture was recycled to the first plate below the chimney tray (the fourth plate below the top of the column). The rate withdrawn from the bottom stream (the line 52, temperature: 45.2° C.) of the second distillation column 5 was 1300 g/h.

According to the process, by withdrawing the aqueous phase (the line 69) formed by the side-cut stream from the second distillation column 5, AD and MeI were removed from the process at a flow rate of 1.84 g/h and a flow rate of 0.145 g/h, respectively. The second distillation column 5 required a reboiler heat quantity of 44.1 kcal/h.

The following Table shows the results of componential analysis in each line depicted in FIG. 3. The aqueous phase in the line 69 was fed to the fourth distillation column 8 without being fed to the third distillation column 7. Thus the composition of the aqueous phase in the line 69 is the same as the composition of the feed line 74 connected to the distillation column 8.

TABLE 11

| Composition in Line No. depicted in FIG. 3 (% by weight) | | | | | | | |
|---|---|---|---|---|---|---|---|
| Line No. | 44 | 52 | 53/61 | C3 vent | 63 | 68 | 69/69a |
| DME | 0.003 | 0.000 | 0.55 | 26.7 | 0.05 | 0.05 | 0.08 |
| AD | 0.179 | 0.019 | 44.7 | BL | 6.4 | 6.1 | 21.0 |
| MeI | BL | BL | BL | 17.8 | BL | BL | 1.7 |
| MeOH | 0.09 | 0.063 | 0.07 | 0.0 | 0.1 | 0.0 | 4.0 |
| MA | 13.9 | 13.9 | 0.5 | 2.2 | 3.8 | 3.9 | 1.6 |
| $H_2O$ | 0.66 | 0.66 | 0.2 | 0.0 | 1.5 | 0.2 | BL |
| AC | 1.95 | 2.0 | 0.0 | 0.0 | 0.0 | 0.0 | 0.0 |
| Total | 100 | 100 | 100 | 100 | 100 | 100 | 100 |

Example 9

A second distillation column 5 having the actual number of stages of 13 [column top temperature of 21.4° C., column bottom temperature of 47.4° C., column top pressure of atmospheric pressure+10 mmH₂O (about 100 Pa)] was provided. A water-rich feed liquid (a line 43b, temperature: 21° C.) and a MeI-rich feed liquid (a line 44, temperature: 21° C.) were fed at 360 g/h and 639 g/h, respectively, to the 7th plate from the bottom of the distillation column, and water (temperature: 21° C.) was fed to the 13th plate from the bottom of the distillation column at rate of 3.8 g/h. An overhead (temperature: 21.4° C.) from a line 53 was cooled in condenser C3 to 7° C. and was refluxed at a reflux rate of 250 g/h for water extractive distillation in the column. The water-rich feed liquid had an AD concentration of 3840 ppm, a MeI concentration of 2.6% by weight, a MeOH concentration of 0.99% by weight, a MA concentration of 8.3% by weight, a water concentration of 63.7% by weight, and an AC concentration of 24.0% by weight. The MeI-rich feed liquid was a methyl iodide solution having an AD concentration of 1860 ppm, a MeI concentration of 82.0% by weight, a MeOH concentration of 0.084% by weight, a MA concentration of 13.6% by weight, a water concentration of 0.85% by weight, and an AC concentration of 3.3% by weight. A chimney tray was installed instead of the third plate below the top of the column, and the whole amount of the falling liquid was withdrawn as a side-cut stream 63 (temperature: 37.2° C.). The side-cut stream was cooled in a cooling unit C4 to 7.1° C. and was then introduced into a hold tank 6c to form two phases of an aqueous phase and an organic phase. A first portion of the aqueous phase having an AD concentration of 23.7% by weight (temperature: 7.1° C.) was withdrawn at a rate of 8.7 g/h from the tank 6c via a line 69. A second portion of the aqueous phase (a line 69a) was withdrawn at a flow rate of 3.9 g/h from the tank 6c and mixed with the whole amount (746 g/h) of the MeI phase (a line 68, temperature: 7.1° C.) withdrawn from the tank 6c, and the resulting mixture was recycled to the first plate below the chimney tray (the fourth plate below the top of the column). The bottom stream (the line 52, temperature: 47.4° C.) of the second distillation column 5 was withdrawn at a rate of 994 g/h in total with the aqueous phase and the MeI phase supplied.

According to the process, by withdrawing the aqueous phase (the line 69) formed by the side-cut stream from the second distillation column 5, AD and MeI were removed from the process at a flow rate of 2.06 g/h and a flow rate of 0.156 g/h, respectively. The second distillation column 5 required a reboiler heat quantity of 43.5 kcal/h.

The following Table shows the results of componential analysis in each line depicted in FIG. 3. The aqueous phase in the line 69 was fed to the fourth distillation column 8 without being fed to the third distillation column 7. Thus the composition of the aqueous phase in the line 69 is the same as the composition of the feed line 74 connected to the distillation column 8.

TABLE 12

| Composition in Line No. depicted in FIG. 3 (% by weight) | | | | | | | | |
|---|---|---|---|---|---|---|---|---|
| Line No. | 43b | 44 | 52 | 53/61 | C3 vent | 63 | 68 | 69/69a |
| DME | 0.0036 | 0.0046 | 0.000 | 0.72 | 21.7 | 0.09 | 0.086 | 0.10 |
| AD | 0.384 | 0.186 | 0.021 | 42.8 | BL | 6.5 | 6.2 | 23.7 |
| MeI | 2.6 | BL | BL | BL | 18.3 | BL | BL | 1.8 |
| MeOH | 0.99 | 0.084 | 0.387 | 0.0 | 1.7 | 0.3 | 0.3 | 2.8 |
| MA | 8.3 | 13.6 | 11.7 | 0.5 | 8.3 | 3.8 | 3.8 | 1.4 |
| $H_2O$ | BL | 0.85 | 23.4 | 0.3 | 0.0 | 1.3 | 0.1 | BL |
| AC | 24.0 | 3.30 | 10.8 | 0.0 | 0.0 | 0.0 | 0.0 | 0.0 |
| Total | 100 | 100 | 100 | 100 | 100 | 100 | 100 | 100 |

Example 10

A second distillation column 5 having the actual number of stages of 13 [column top temperature of 21.4° C., column bottom temperature of 47.9° C., column top pressure of atmospheric pressure+10 mmH₂O (about 100 Pa)] was provided. A water-rich feed liquid (a line 43b, temperature: 21° C.) and a MeI-rich feed liquid (a line 44, temperature: 21° C.) were fed at 932 g/h and 105 g/h, respectively, to the 7th plate from the bottom of the distillation column, and water (temperature: 20° C.) was fed to the 13th plate from the bottom of the distillation column at 6.5 g/h. An overhead (temperature: 21.4° C.) from a line 53 was cooled in condenser C3 to 6.9° C. and was refluxed at a reflux rate of 259 g/h for water extractive distillation in the column. The water-rich feed liquid had an AD concentration of 3840 ppm, a MeI concentration of 2.4% by weight, a MeOH concentration of 0.99% by weight, a MA concentration of 8.3% by weight, a water concentration of 63.2% by weight, and an AC concentration of 24.5% by weight. The MeI-rich feed liquid was a methyl iodide solution having an AD concentration of 1860 ppm, a MeI concentration of 81.9% by weight, a MeOH concentration of 0.10% by weight, a MA concentration of 13.7% by weight, a water concentration of 0.85% by weight, and an AC concentration of 3.3% by weight. A chimney tray was installed instead of the third plate below the top of the column, and the whole amount of the falling liquid was withdrawn as a side-cut stream 63 (temperature: 37.1° C.) The side-cut stream was cooled in a cooling unit C4 to 6.9° C. and was then introduced into a hold tank 6c to form two phases of an aqueous phase and an organic phase. A first portion of the aqueous phase having an AD concentration of 22.0% by weight (temperature: 6.9° C.) was withdrawn at 10.4 g/h from the tank 6c via a line 69. A second portion of the aqueous phase (a line 69a) was withdrawn at a flow rate of 6.2 g/h from the tank 6c and mixed (or merged) with the whole amount (746 g/h) of the MeI phase (a line 68, temperature: 6.9° C.) withdrawn from the tank 6c, and the resulting mixture was recycled to the first plate below the chimney tray (the fourth plate below the top of the column). The bottom stream (the line 52, temperature: 47.9° C.) of the second distillation column 5 was withdrawn at a rate of 1033 g/h in total with the aqueous phase and the MeI phase supplied.

According to the process, by withdrawing the aqueous phase (the line 69) formed by the side-cut stream from the second distillation column 5, AD and MeI were removed from the process at a flow rate of 2.28 g/h and a flow rate of 0.183 g/h, respectively. The second distillation column 5 required a reboiler heat quantity of 39.2 kcal/h.

The following Table shows the results of componential analysis in each line depicted in FIG. 3. The aqueous phase in the line 69 was fed to the fourth distillation column 8 without being fed to the third distillation column 7. Thus the composition of the aqueous phase in the line 69 is the same as the composition of the feed line 74 connected to the distillation column 8.

Example 11

The water extraction was carried out in the same manner as the above Examples with different numbers of stages of the second distillation column 5 (10 stages to 43 stages), different amounts of the water-rich feed liquid (the line 43b) to the second distillation column 5 (0 to 1000 g/h), different amounts of the MeI-rich feed liquid (the line 44) (0 to 1000 g/h), different ratios of the water-rich feed liquid relative to the MeI-rich feed liquid (the former/the latter (weight ratio)=5/95 to 100/0), different feed amounts of water to the top of the column (0 to 8 g/h), and different recycle amounts of the aqueous phase in the line 69a (0 to 8 g/h). The correlation between the AD concentration in the aqueous extract (the line 69) and the methyl iodide/acetaldehyde ratio (MeI/AD ratio) was examined. The results are shown in FIG. 5. The curve in FIG. 5 is a polynomial approximation curve prepared by a software "Excel".

Table 14 and FIG. 5 show the fact that the AD concentration in the aqueous extract has an optimal value and too low or high an AD concentration increases the discharge of MeI to outside of the system.

In Comparative Example 1, the removal amount of AD and the lost amount of MeI indicate the amount of AD and the amount of MeI in the aqueous extract 275 from the water extractive distillation column 207 in FIG. 4. In Examples,

TABLE 13

Composition in Line No. depicted in FIG. 3 (% by weight)

| Line No. | 43b | 44 | 52 | 53/61 | C3 vent | 63 | 68 | 69/69a |
|---|---|---|---|---|---|---|---|---|
| DME | 0.004 | 0.004 | 0.000 | 0.65 | 22.1 | 0.14 | 0.14 | 0.10 |
| AD | 0.384 | 0.186 | 0.112 | 42.1 | BL | 6.6 | 6.2 | 22.0 |
| MeI | 2.6 | BL | 10.7 | BL | 13.6 | BL | BL | 1.8 |
| MeOH | 0.99 | 0.103 | 0.872 | 0.0 | 1.2 | 0.3 | 0.3 | 3.1 |
| MA | 8.3 | 13.7 | 8.9 | 0.5 | 5.1 | 3.2 | 3.3 | 1.3 |
| $H_2O$ | BL | 0.85 | BL | 0.3 | 0.0 | 1.7 | 0.2 | BL |
| AC | 24.54 | 3.31 | 22.5 | 0.0 | 0.0 | 0.0 | 0.0 | 0.0 |
| Total | 100 | 100 | 100 | 100 | 100 | 100 | 100 | 100 |

Table 14 shows the results obtained in Examples 1 to 10. Table 14 also shows the number of distillation stages, the separation efficiency of PRC's and methyl iodide, and the energy efficiency.

TABLE 14

| | Number of distillation stages (stages) | Removal amount of AD (g/h) | Lost amount of MeI (g/h) | MeI/ AD ratio | Reboiler Duty | |
|---|---|---|---|---|---|---|
| | | | | | 2nd distillation column (kcal/h) | Energy required for removing unit AD (Kcal/g-AD) |
| Comparative Example 1 | 100 | 2.25 | 0.27 | 0.122 | 100.2 | 44.5 |
| Example 1 | 43 | 2.47 | 0.22 | 0.091 | 56.1 | 22.7 |
| Example 2 | 43 | 2.44 | 0.18 | 0.076 | 89.7 | 36.8 |
| Example 3 | 43 | 2.45 | 0.18 | 0.075 | 66.1 | 27 |
| Example 4 | 43 | 2.42 | 0.16 | 0.066 | 86.4 | 35.7 |
| Example 6 | 30 | 2.09 | 0.167 | 0.081 | 47.7 | 22.8 |
| Example 7 | 15 | 1.85 | 0.17 | 0.092 | 42.7 | 23.1 |
| Example 8 | 10 | 1.84 | 0.145 | 0.081 | 44.1 | 24.0 |
| Example 9 | 13 | 2.06 | 0.156 | 0.076 | 43.5 | 21.1 |
| Example 10 | 13 | 2.28 | 0.183 | 0.082 | 39.2 | 17.2 | the removal amount of AD and the lost amount of MeI indicate the amount of AD and the amount of MeI in the aqueous phase 69 formed by the side-cut stream from the second distillation column 5. In Comparative Example 1, the methyl iodide/acetaldehyde ratio (MeI/AD ratio) was calculated from the amount of AD and the amount of MeI in the aqueous extract 275. In Examples 1 to 10, the methyl iodide/acetaldehyde ratio (MeI/AD ratio) was calculated from the amount of AD and the amount of MeI in the aqueous phase 69.

[Consideration]

The comparison between Comparative Example 1 and Examples 1 to 8, in each case where the MeI-rich feed liquid (the line 44) was fed, shows that AD is condensed by the distillation column having 100 stages and separated by water extraction in Comparative Example, while AD is efficiently separable with a small number of stages according to water extractive distillation conditions of Examples. Among these Examples, according to Example 8, AD is sufficiently separable at only 10 stages, and the steam amount (energy) required per unit AD removal is only 24 kcal/g-AD against 44.5 kcal/g-AD for Comparative Example 1. Thus the amount of steam consumption is significantly reducible.

Further, from the comparison of Comparative Example 1 with Example 10, the vapor amount (energy) required per unit AD removal is only 17.2 kcal/g-AD for Example 10, in which the water-rich feed liquid (the line 43b) was fed, against 44.5 kcal/g-AD for Comparative Example 1. Thus AD is removable with 39% of the energy required in the conventional art. This reason is probably that the feed liquid rich in the aqueous phase, which has a higher AD concentration compared with the feed liquid rich in methyl iodide, allows efficient AD removal. Moreover, compared with Comparative Example 1, all Examples have a lower MeI/AD ratio and also reduce the discharge of MeI to outside of the system.

In a case where the water-rich feed liquid (the line 43b) and the MeI-rich feed liquid (the line 44) are fed to the second distillation column 5, AD is effectively separable with a decreased energy even by a small number of stages along with the increase of the ratio of the water-rich feed liquid (Example 9: the weight ratio of the water-rich feed liquid (aqueous phase) relative to the MeI-rich feed liquid (MeI phase)=36/64; Example 10: the weight ratio of the aqueous phase relative to the MeI phase=90/10). The reason why is probably as follows: the presence of methyl iodide throughout the whole area from the bottom to the top of the distillation column 5 improves the AD separation efficiency, and the AD concentration in the water-rich feed liquid is higher than that in the MeI-rich feed liquid.

INDUSTRIAL APPLICABILITY

According to the present invention, PRC's (e.g., acetaldehyde) can efficiently be separated and removed from a process stream, and a process significantly useful for stably producing high-quality acetic acid can be provided.

REFERENCE SIGNS LIST

1 . . . Reactor
2 . . . Flasher (Evaporator)
3 . . . Splitter column (First distillation column)
4 . . . Decanter
5 . . . Second distillation column (Column for separating PRC's such as acetaldehyde)
6a . . . Separation unit
6b . . . Hold tank and Decanter
6c . . . Decanter
7 . . . Third distillation column
8 . . . Fourth distillation column (Extractive distillation column)

The invention claimed is:

1. A process for producing acetic acid, comprising the steps of:
   distilling a mixed composition containing at least a permanganate reducing compound (PRC), methyl iodide, methyl acetate, and acetic acid to separate the mixed composition into an overhead and an acetic acid stream, the overhead containing at least a PRC and methyl iodide, and the acetic acid stream containing product acetic acid, and
   subjecting at least a portion of the overhead to a second distillation step to form an overhead stream, a side-cut stream, and a lower stream;
   wherein the process further comprises the steps of:
   adding an extractant extracting a PRC preferentially to methyl iodide to the concentration zone of a PRC and methyl iodide in the distillation column of the second distillation step, and
   withdrawing an extraction mixture falling from the concentration zone as the side-cut stream to biphasically separate the extraction mixture into an upper aqueous phase and a lower organic phase.

2. A process according to claim 1, comprising:
   a reaction step of continuously carbonylating methanol in the presence of a catalyst system comprising a metal catalyst, a metal halide, and methyl iodide;
   a flash evaporation step of continuously separating the reaction mixture into a volatile phase and a less-volatile phase, the volatile phase containing product acetic acid and methyl iodide, and the less-volatile phase containing the metal catalyst and the metal halide;
   a first distillation step of continuously separating the volatile phase into the overhead containing methyl iodide and by-product acetaldehyde, and the stream containing acetic acid; and
   the second distillation step of distilling at least a portion of the overhead to form the overhead stream, the side-cut stream, and the lower stream.

3. A process according to claim 1, wherein the mixed composition contains methyl iodide in a concentration of not less than 1.5% by weight.

4. A process according to claim 1, wherein the mixed composition is biphasically separable, and comprises at least a portion of an organic phase, at least a portion of an aqueous phase, or a mixed composition containing the organic phase and the aqueous phase.

5. A process according to claim 1, wherein the extraction mixture or the side-cut stream satisfies the following conditions (i), (ii), and/or (iii):
   (i) the PRC concentration in the extraction mixture or the side-cut stream is higher than the PRC concentration in each of the mixed composition and the lower stream,
   (ii) the extraction mixture or the side-cut stream has a PRC concentration of 0.1 to 45% by weight,
   (iii) the ratio of the PRC relative to methyl iodide in the extraction mixture or the side-cut stream is larger than the ratio of the PRC relative to methyl iodide in each of the mixed composition and the lower stream.

6. A process according to claim 1, wherein the mixed composition comprises, in addition to acetaldehyde and methyl iodide, (a) methyl acetate and/or (b) at least one component selected from the group consisting of acetic acid, methanol, water, dimethyl ether, and an acetaldehyde derivative.

7. A process according to claim 1, wherein the weight ratio of the flow rate of the extractant relative to the flow rate of the mixed composition is 0.0001/100 to 100/100 in the former/the latter in terms of liquid matter.

8. A process according to claim 1, wherein the distillation column of the second distillation step is provided with a receiver, the receiver being disposed at a lower position than the addition port for the extractant, permitting a vapor or evaporation fraction of the mixed composition to ascend to the concentration zone, and being capable of receiving the extraction mixture falling from the concentration zone;
   the extractant is added to the concentration zone formed above the receiver, the extractant being separable from methyl iodide to form an extract phase; and
   the extraction mixture is withdrawn as the side-cut stream from the withdrawing port communicating with the receiver.

9. A process according to claim 1, wherein the distillation column of the second distillation step is provided with at least one chimney tray;
   the extractant is added to the concentration zone, the extractant being an aqueous extractant, the concentration zone being formed above or over an uppermost chimney tray and containing a vapor or evaporation fraction of the mixed composition;

the extraction mixture falling from the concentration zone is received in a tray section or area of the chimney tray; and the extraction mixture retained in the tray is withdrawn as the side-cut stream.

10. A process according to claim 1, wherein the extractant comprises at least one aqueous solvent selected from the group consisting of (i) water, (ii) an aqueous process stream produced in the process, and (iii) an aqueous mixture produced by water absorption treatment of an off-gas from the process, and the extraction mixture is separable into an upper phase and a lower phase.

11. A process according to claim 1, which further comprises recycling an organic phase containing at least methyl iodide to the second distillation step by the following method (a), (b), or (c):

(a) biphasically separating the extraction mixture withdrawn from the distillation column of the second distillation step into an aqueous phase containing at least acetaldehyde and an organic phase containing at least methyl iodide, separating the aqueous phase, and recycling the organic phase to the distillation column of the second distillation step, (b) biphasically separating the extraction mixture withdrawn from the distillation column of the second distillation step into an aqueous phase containing at least acetaldehyde and an organic phase containing at least methyl iodide, and recycling a portion of the aqueous phase and the organic phase to the distillation column of the second distillation step, (c) biphasically separating the extraction mixture and optionally the overhead stream into an aqueous phase and an organic phase containing at least methyl iodide, subjecting at least a portion of the aqueous phase to distillation and/or water extractive distillation in a succeeding distillation step, and directly or indirectly recycling the organic phase to the distillation column of the second distillation step from a lower position than the withdrawing port for withdrawing the side-cut stream.

12. A process according to claim 1, which further comprises the steps of:

biphasically separating the extraction mixture and optionally the overhead stream to form an aqueous phase and an organic phase, distilling the aqueous phase in a succeeding distillation step to form another overhead stream containing acetaldehyde and methyl iodide, and a liquid stream containing the extractant, and utilizing the liquid stream containing the extractant as an extractant for obtaining the extraction mixture in the second distillation step.

13. A process according to claim 1, which further comprises the steps of:

biphasically separating the extraction mixture and optionally the overhead stream into an aqueous phase and an organic phase, distilling at least a portion of the aqueous phase in a succeeding distillation step, directly or indirectly recycling the organic phase to the second distillation step from a lower position than the withdrawing port for the side-cut stream, and directly or indirectly feeding a miscible solvent to the second distillation step from a lower position than the withdrawing port for the side-cut stream, the miscible solvent being miscible with the organic phase separated from the extraction mixture and comprising at least one component selected from the group consisting of water, acetic acid, methyl iodide, and methanol.

14. A process according to claim 1, which further comprises:

a reaction step of continuously carbonylating methanol in the presence of a catalyst system comprising a metal catalyst, a metal halide, and methyl iodide;

a flash evaporation step of continuously separating the reaction mixture into a volatile phase and a less-volatile phase, the volatile phase containing product acetic acid and methyl iodide, and the less-volatile phase containing the metal catalyst and the metal halide;

a first distillation step of continuously separating the volatile phase into the overhead containing methyl iodide and by-product acetaldehyde, and the stream containing acetic acid; and a step of condensing a gaseous phase to form an organic phase and an aqueous phase, the gaseous phase being produced from at least one step selected from the group consisting of these steps and containing at least acetaldehyde and methyl iodide, wherein at least a portion of the organic phase and/or at least a portion of the aqueous phase is subjected to the second distillation step, and water or at least a portion of the aqueous phase is fed as the extractant to said second distillation step to form the overhead stream, the side-cut stream, and the lower stream.

* * * * *